United States Patent
Looper et al.

(10) Patent No.: US 11,339,140 B2
(45) Date of Patent: May 24, 2022

(54) COMPOSITIONS AND METHODS COMPRISING SUBSTITUTED 2-AMINOIMIDAZOLES

(71) Applicants: Curza Global, LLC, Provo, UT (US); University of Utah Research Foundation, Salt Lake City, UT (US)

(72) Inventors: Ryan E. Looper, Salt Lake City, UT (US); Justin M. Salvant, Salt Lake City, UT (US); Emily K. Kirkeby, Salt Lake City, UT (US); Wenxing Guo, Salt Lake City, UT (US); Katrin P. Guillen, Salt Lake City, UT (US); Bryan E. Welm, Salt Lake City, UT (US)

(73) Assignees: Curza Global, LLC, Provo, UT (US); The University of Utah, Salt Lake City, UT (US)

( * ) Notice: Subject to any disclaimer, the term of this patent is extended or adjusted under 35 U.S.C. 154(b) by 0 days.

(21) Appl. No.: 16/586,667

(22) Filed: Sep. 27, 2019

(65) Prior Publication Data
US 2020/0024251 A1    Jan. 23, 2020

Related U.S. Application Data

(63) Continuation of application No. PCT/US2018/025730, filed on Apr. 2, 2018.

(60) Provisional application No. 62/480,173, filed on Mar. 31, 2017.

(51) Int. Cl.
| C07D 401/04 | (2006.01) |
| C07D 233/88 | (2006.01) |
| C07D 405/04 | (2006.01) |
| C07D 487/04 | (2006.01) |

(52) U.S. Cl.
CPC ......... *C07D 401/04* (2013.01); *C07D 233/88* (2013.01); *C07D 405/04* (2013.01); *C07D 487/04* (2013.01)

(58) Field of Classification Search
CPC .. C07D 233/88; C07D 401/04; C07D 405/04; C07D 487/04
See application file for complete search history.

(56) References Cited

U.S. PATENT DOCUMENTS

| 5,574,057 A | 11/1996 | Ireland et al. |
| 2003/0055263 A1 | 3/2003 | Priepke et al. |
| 2005/0070588 A1 | 3/2005 | Weinstein et al. |
| 2013/0190363 A1* | 7/2013 | Ikeda ............ A61P 25/28 514/341 |
| 2017/0100375 A1 | 4/2017 | Looper et al. |

FOREIGN PATENT DOCUMENTS

| JP | 4730693 A | 11/1972 |
| WO | 02/14311 A2 | 2/2002 |
| WO | 03/006443 A2 | 1/2003 |
| WO | 2005/012263 A1 | 2/2005 |
| WO | 2010/036821 A1 | 4/2010 |
| WO | 2011/080132 A2 | 7/2011 |
| WO | 2012014699 A1 | 2/2012 |
| WO | 2012/161965 A1 | 11/2012 |
| WO | 2016/118951 A2 | 7/2016 |
| WO | 2016161361 A1 | 10/2016 |
| WO | 2015/143240 A2 | 10/2018 |
| WO | 2018/184019 A1 | 10/2018 |

OTHER PUBLICATIONS

Guo et al. (J. Agric. Food Chem. 2016, 64, 4264-4274).*
Bain et al., "The selectivity of protein kinase inhibitors: a further update." Biochem. J. 2007, 408, pp. 297-315.
Copp et al., "Naamidine A is an antagonist of the epidermal growth factor receptor and an in vivo active antitumor agent", J. Med. Chem., vol. 41, No. 20, Sep. 1, 1998, pp. 3909-3911.
Database PubChem Substance, "PubChem Open Chemistry database", Jan. 9, 2014, 37 pages.
Ermolat'ev et al., "Concise and Diversity-Oriented Route toward Polysubstituted 2-Aminoimidazole Alkaloids and Their Analogues," Angew. Chem., 2010, vol. 122, pp. 9655-9658.
Guo et al., "First Discovery of Polycarpine, Polycarpaurines A and C, and Their Derivatives as Novel Antiviral and Antiphytopathogenic Fungus Agents," J, Agric. Food Chem., 2016, vol. 64, pp. 4264-4272.
PCT/US2015/021602 , "International Search Report and Written Opinion", dated Sep. 22, 2015, 19 pages.
PCT/US2018/025730, International Search Report dated Jun. 14, 2018, 2 pages.
Zhang et al., "4,5-Di-substituted benzyl-imidazol-2-substituted amines as the structure template for the design and synthesis of reversal agents against P-gp-mediated multidrug resistance breast cancer cells.", European Journal of Medicinal Chemistry, vol. 83, Jun. 10, 2014, pp. 74-83.
Japanese International Application No. JP2019-553461, "Office Action", dated Jan. 18, 2022, 10 pages.

* cited by examiner

*Primary Examiner* — Valerie Rodriguez-Garcia
(74) *Attorney, Agent, or Firm* — Kilpatrick Townsend & Stockton LLP

(57) ABSTRACT

The present invention presents 2-(acylamino)imidazoles with therapeutic activity, including selective activity against cancer cells, and compositions comprising them. Methods of using and preparing the 2-(acylamino)imidazoles are also presented.

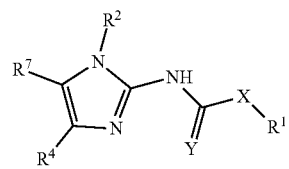

14 Claims, 11 Drawing Sheets

COMPOSITIONS AND METHODS COMPRISING SUBSTITUTED 2-AMINOIMIDAZOLES

CROSS-REFERENCES TO RELATED APPLICATIONS

The present application is a continuation of International Patent Application No. PCT/US2018/025730, filed Apr. 2, 2018, which claims the priority of U.S. Provisional Patent Application No. 62/480,173 (filed Mar. 31, 2017), the disclosures of which are herein incorporated by reference in their entirety for all purposes.

STATEMENT AS TO RIGHTS TO INVENTIONS MADE UNDER FEDERALLY SPONSORED RESEARCH AND DEVELOPMENT

Part of the work leading to this invention was carried out with U.S. Government support provided by the National Institute of Health (NIH Grant Nos. 2R01-RGM090082-A1 and R01 CA140296). The U.S. Government therefore has certain rights in this invention.

FIELD OF THE INVENTION

In some embodiments, the present invention is directed to compositions and methods comprising 2-(acylamino)imidazoles, including their regioselective preparation and medical uses.

BACKGROUND OF THE INVENTION

Tuberculosis is a world-wide health threat. Agents that can effectively kill this bacterium while maintaining moderate cytotoxicity hold promise to treat this disease in humans. Given the advent of both multi-drug resistant (MDR) and completely drug resistant (XDR) strains of this pathogen, development of a "next-generation" series of small molecules to treat this disease could provide great benefits.

Naamidine A, a natural product isolated from the marine sponge *Leucetta chagosensis*, displays anti-proliferative activity against both *Mycobacterium tuberculosis* ($IC_{50}$=0.94 µM or 0.41 µg/mL) and *Candida albicans* ($MIC_{100}$=0.78 µM). The related natural products kealiinines B and C also display anti-tubercular activity ($IC_{50}$=8.9 µM and 42 µM respectively). Naamidine A has been shown to be relatively well tolerated in vivo for mouse models, with a maximum tolerated dose of 25 mg/Kg (see Ireland et al., *J. Med. Chem.* 1998, 41, 3909). Further, in CEM-TART cells, the $IC_{50}$=34.8 µM, which indicates a selectivity ratio of 37.

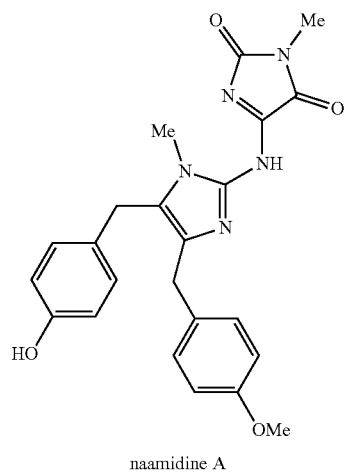

naamidine A

Naamidine A also displays selective anti-cancer activity of therapeutic interest. See, e.g., U.S. Pat. No. 5,574,057. Many cancer drugs are nearly indiscriminate in their cytotoxicity and affect healthy and tumor cells comparably. The resulting narrow therapeutic treatment windows limit both the amount of drug that can be administered to patients and the duration of treatment, reducing the overall efficacy of the therapy. Additionally, the adverse side effects arising from low therapeutic indices can necessitate additional palliative care efforts and further burden patient recovery. In contrast, naamidine A selectively inhibits proliferation of cancerous cells, thereby providing a potential advantage over less selective agents.

Naamidine A's activity may partially arise from its ability to coordinate zinc. Zinc is an essential trace metal; it is estimated that 10% of the proteome may bind zinc, with 40% of these proteins functioning as transcription factors and the remaining 60% operating in an enzymatic or an ion transport capacity. Andreini et al. *J Proteome Res* 2005; 5(1):196-201. Perturbations in zinc homeostasis are correlated with various disease states, and in the case of breast cancer, increased zinc levels have been observed in malignant breast tissue compared to nonmalignant tissue. Margalioth et al. Cancer 1983; 52(5):868-72; Geraki et al. Phys Med Biol 2004; 49(1):99. As such, exploiting differences in zinc homeostasis between healthy and diseased tissue may provide new avenues for the development of anti-cancer therapeutics.

Despite naamidine A's promise as a therapeutic agent, its 1H-imidazole-2,5-dione substituent complicates its preparation and evaluation as a possible drug. Simpler, easier-to-make analogs of naamidine A possessing therapeutically interesting activity, especially anti-tubercular or anti-cancer activity, would present advantages over naamidine A itself, especially if the analogs were available by an efficient synthetic route.

The present invention's 2-aminoimidazole compositions and methods present embodiments with these and other advantages.

BRIEF SUMMARY OF THE INVENTION

In a first embodiment, the invention presents a 2-(acylamino)imidazole compound of structure I:

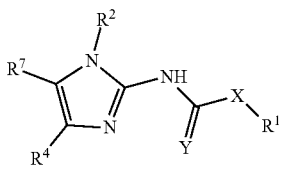

or a salt thereof;
wherein:
R$^1$ is a member selected from the group including alkyl, alkenyl, alkynyl, aryl, arylalkyl, heteroaryl, and heteroarylalkyl;

X is a member selected from the group including a bond, O, and NR$^{5a}$;

Y is a member selected from the group including O, S, or NR$^{5b}$; or, when X is O or a bond, Y is O;

R$^2$ is a member independently selected from the group including alkyl, alkenyl, alkynyl, and arylalkyl; or, alternatively, R$^2$ and R$^7$ join to form an additional heterocyclyl fused ring;

R$^4$ is a member independently selected from the group including aryl and heteroaryl, wherein R$^4$ is unsubstituted or has from one to five R$^{6a}$ substituents;

R$^{5a}$ and R$^{5b}$ are each a member independently selected from the group including hydrogen, alkyl, fluoroalkyl, alkenyl, alkynyl, cycloalkyl, cycloalkylalkyl, arylalkyl, and heteroarylalkyl;

each of the R$^{6n}$ members is independently selected from the group including alkyl, hydroxy, alkoxy, aminoalkoxy, alkylamino, alkylaminoalkoxy, alkenyl, alkynyl, aryl, aryloxy, arylamino, cycloalkyl, cycloalkylalkyl, cycloalkoxy, cycloalkylalkoxy, cycloalkylamino, cycloalkylalkylamino, heterocyclyl, heterocycyloxy, heterocycylalkyloxy, heterocycylamino, heterocycylalkylamino, halo, haloalkyl, fluoroalkyloxy, arylalkyl, arylalkyloxy, arylalkylamino, heteroaryl, heteroaryloxy, heteroarylamino, heteroarylalkyl, heteroarylalkyloxy, and heteroarylalkylamino; or, alternatively, a pair of adjacent R$^{6n}$ members join to form an additional fused ring that is selected from the group including cycloalkyl, aryl, heterocyclyl, and heterocycloaryl; and R$^7$ is a member independently selected from the group including hydrogen, halo, trifluoromethyl, and alkyl; or, alternatively, R$^2$ and R$^7$ join to form an additional heterocyclyl fused ring. In some preferred aspects of the first embodiment, the 2-(acylamido)imidazole compound is not a natural product.

In some embodiments, the invention presents a composition for therapeutic use, the composition including a 2-(acylamino)imidazole of one of the aspects herein. In some aspects, the composition further includes a pharmaceutically acceptable excipient.

In a second embodiment, the invention presents a method of killing bacteria in vitro, the method including treating the bacteria with a composition set forth in the first embodiment or one of its aspects.

In a third embodiment, the invention presents a method of killing bacteria in vivo, the method including administering a composition set forth in the first embodiment or one of its aspects to a patient.

In a fourth embodiment, the invention presents a method of treating cancer, the method including administering a composition set forth in the first embodiment or one of its aspects to a patient with cancer, thereby treating the patient.

In a fifth embodiment, the invention presents a method of selectively preparing a 4-substituted imidazole, the method including the steps:
cyclizing an α-alkylamino ketone and an acyl cyanamide to form a 2-N-acyl imidazolidin-2-imine product; and
converting the 2-N-acyl imidazolidin-2-imine to a 2-acylaminoimidazole product; wherein the 2-acylamino product is substantially free from 1-acyl and 3-acyl regioisomers (e.g., <2% or <1% of such products). In some aspects, the cycling step comprises an acid catalyst. In some preferred aspects, the 2-acylamino product is substantially free from N$^2$,N$^2$-diacyl products (e.g., <2% or <1% of such products).

In a sixth embodiment, the invention presents a method of selectively preparing a 2-acylamino 4-substituted imidazole, the method comprising the steps:
monoalkylating an α-amino acid, ester, or amide at the α-amino group;
converting the α-alkylamino acid, ester, or amide to an α-alkylamino ketone;
cyclizing the α-alkylamino ketone and an acyl cyanamide to form a 2-N-acyl imidazolidin-2-imine product; and
converting the 2-N-acyl imidazolidin-2-imine to a 2-acylaminoimidazole product; wherein the 2-acylamino product is substantially free from 1-acyl and 3-acyl regioisomers (e.g., <2% or <1% of such products). In some aspects, the cycling step comprises an acid catalyst. In some preferred aspects, the 2-acylamino product is substantially free from N$^2$,N$^2$-diacyl products (e.g., <2% or <1% of such products).

In a seventh embodiment, the invention presents a method of inducing metal ion dyshomeostasis, the method including the steps of:
causing the composition of the first embodiment or one of its aspects to contact a metal ion, thereby forming a chelated complex, wherein the chelated complex forms outside a lysosome;
allowing the chelated complex to enter the lysosome;
allowing the chelated complex to dissociate within the lysosome, thereby increasing the internal concentration of the metal ion. In some aspects, the metal ion is Zn$^{2+}$.
In some aspects, the dyshomeostasis causes cell death.

Additional embodiments of the present invention are apparent from the Detailed Description, Examples, and claims.

DETAILED DESCRIPTION OF THE INVENTION

Definitions

Figure 1:
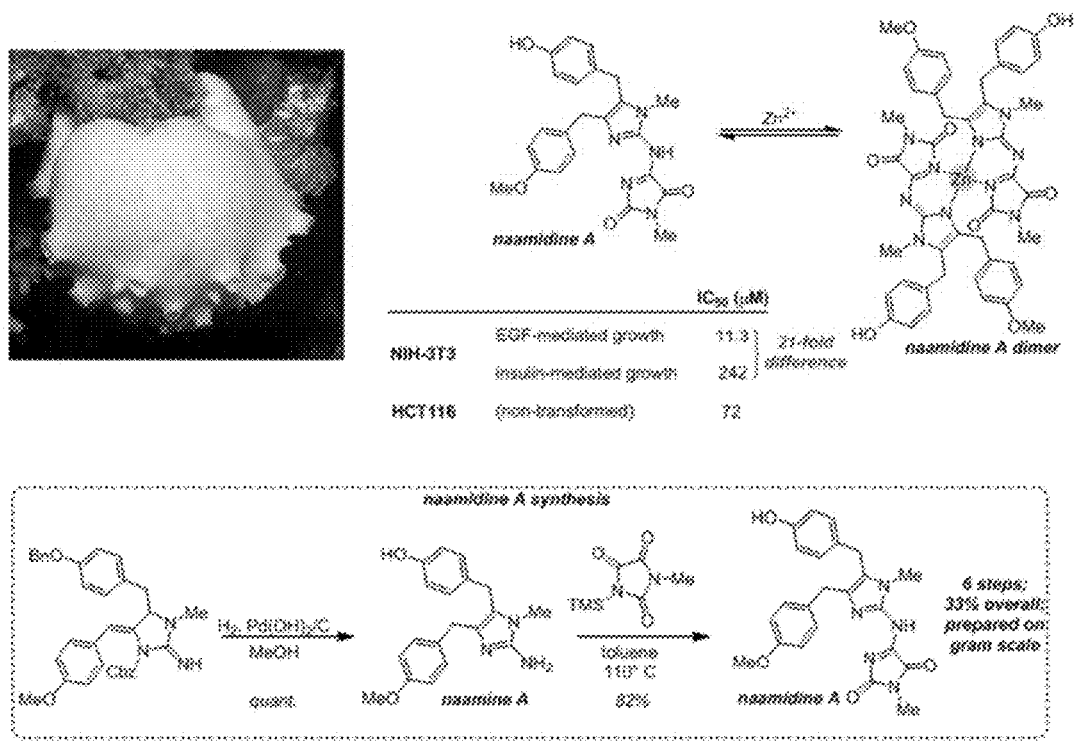
FIG. 1 shows the structure of naamidine A, its biological source, and a successful approach to its synthesis.
Figure 2:
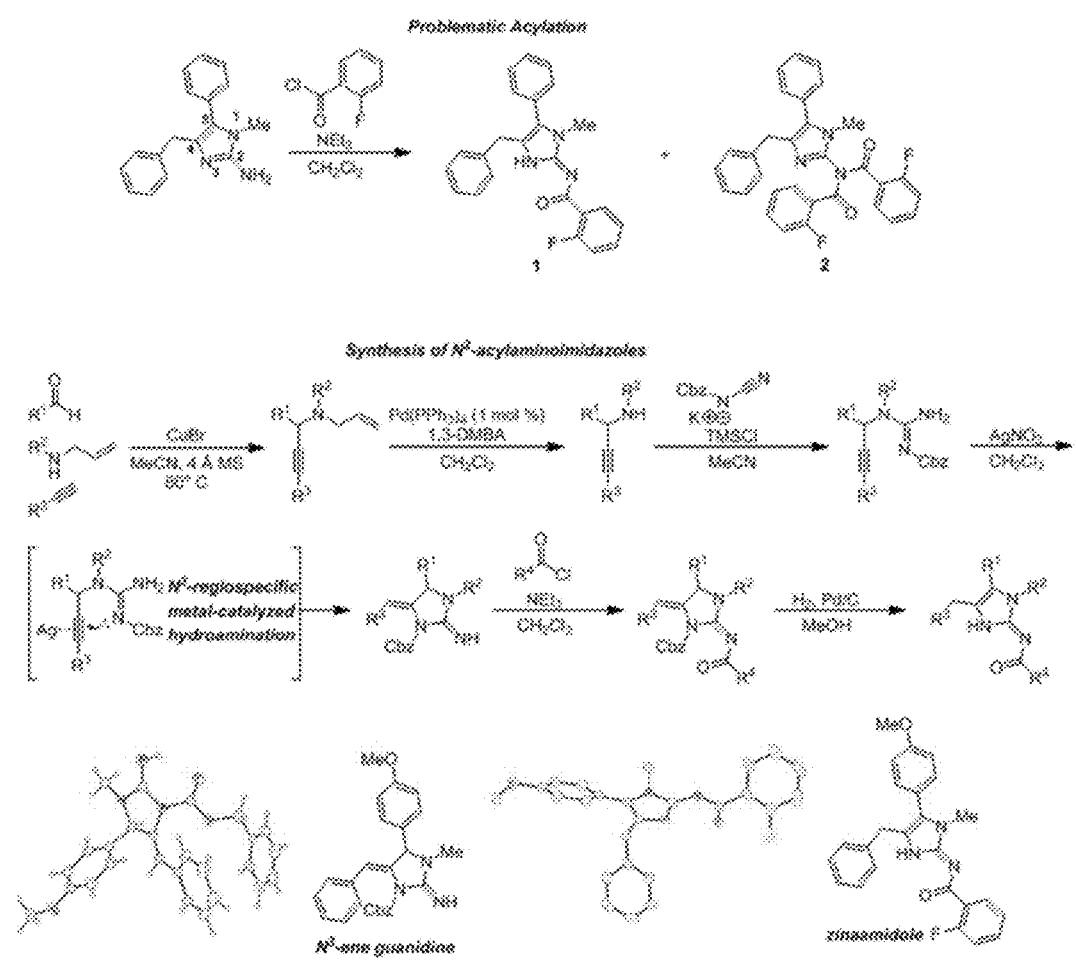
FIG. 2 shows a route to synthesis of naamidine A analogs.
Figure 3:
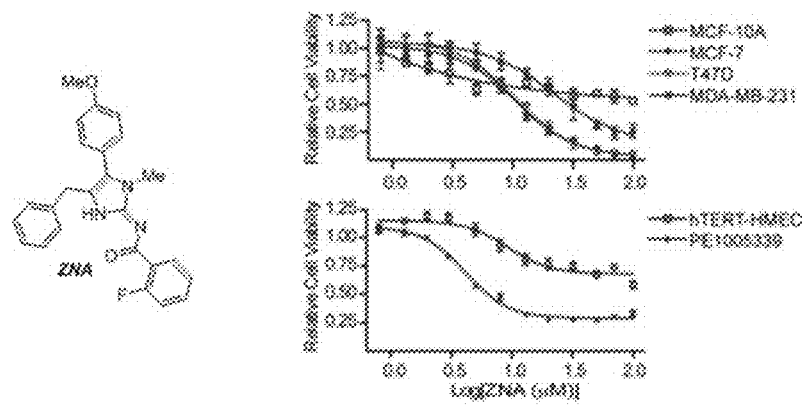
FIG. 3 shows the structure and anticancer activity of ZNA. ZNA's performance is rated on growth inhibition of chemoresistant breast cancer patient pleural effusion cells (PE1007070) versus non-transformed mammary tissue (hTERT-HMEC).
Figure 4:
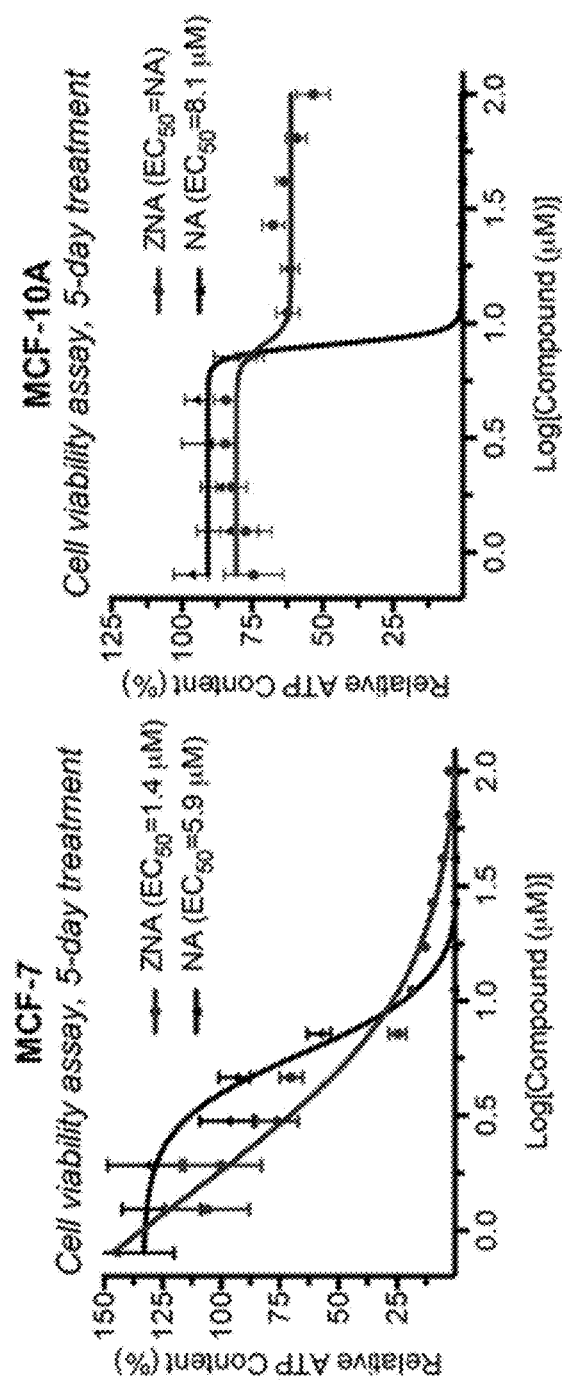
FIG. 4 shows a comparison of the effects of ZNA and naamidine A on cell viability.
Figure 4:
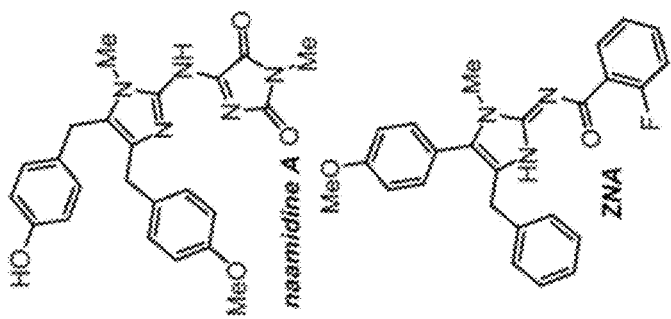
Figure 5:
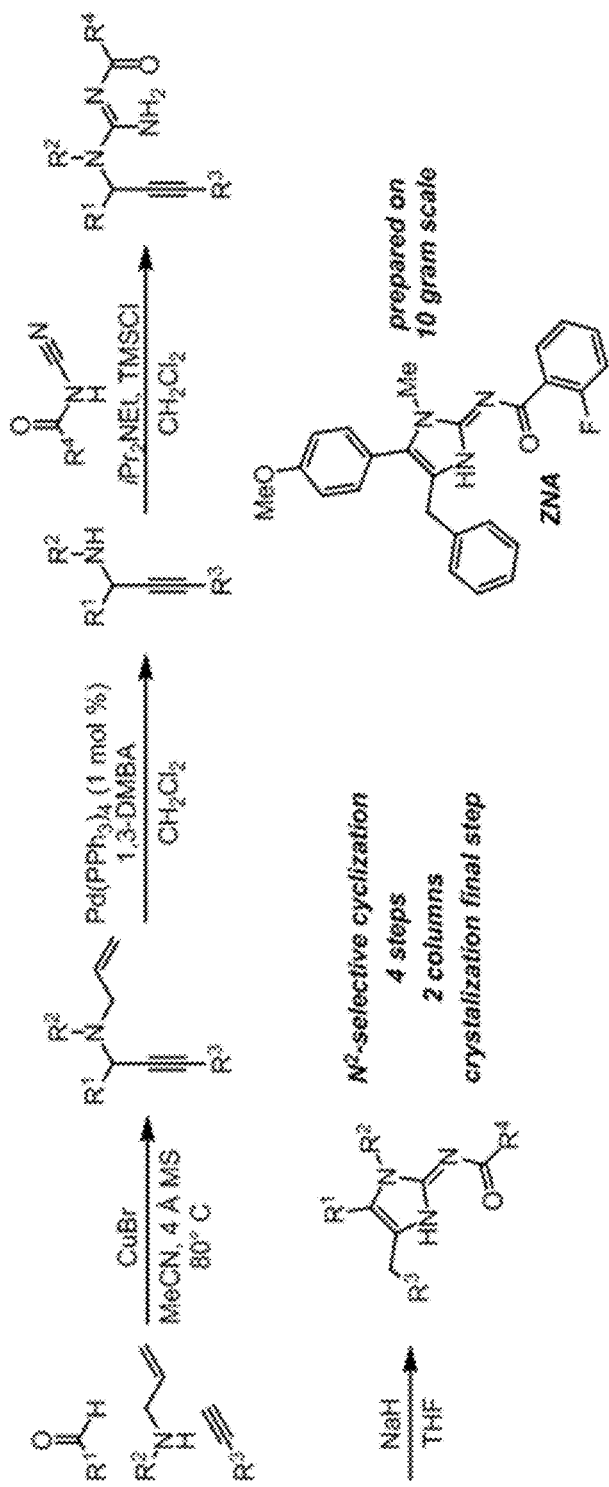
FIG. 5 shows a route to synthesis of naamidine A analogs.
Figure 6:
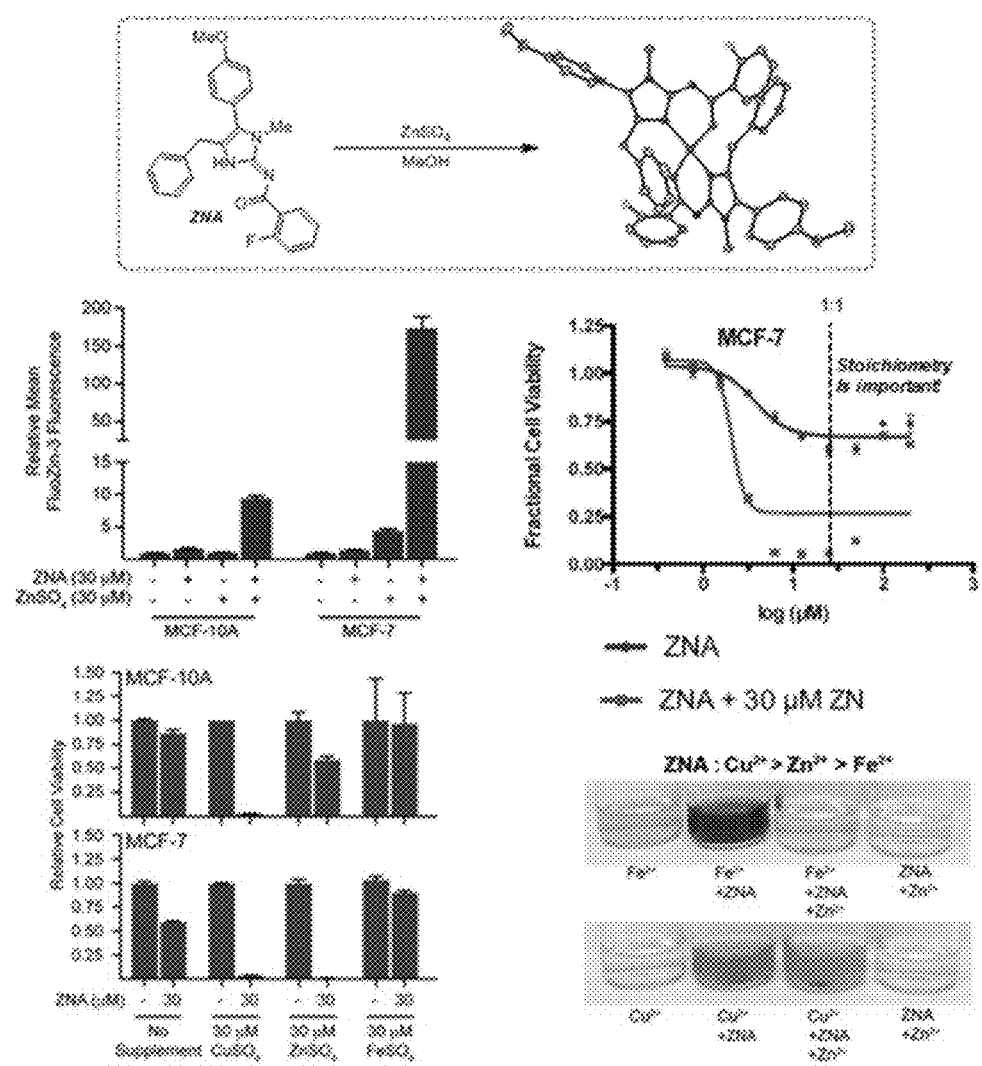
FIG. 6 shows the zinc affinity of ZNA.
Figure 7:
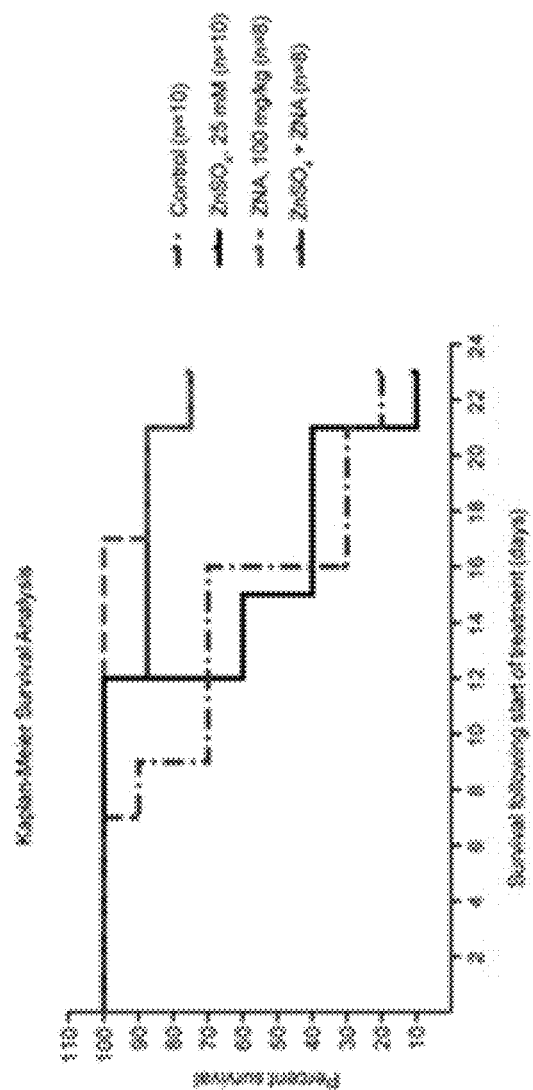
FIG. 7 shows the results of an in vivo study of the effects of ZNA on induced tumors in mice. EF1α-PyMT tumors were induced in mice and incubated for 21 days. They were treated with ZNA (100 mg/kg), ZnSO$_4$, and ZNA+ZnSO$_4$.
Figure 8:
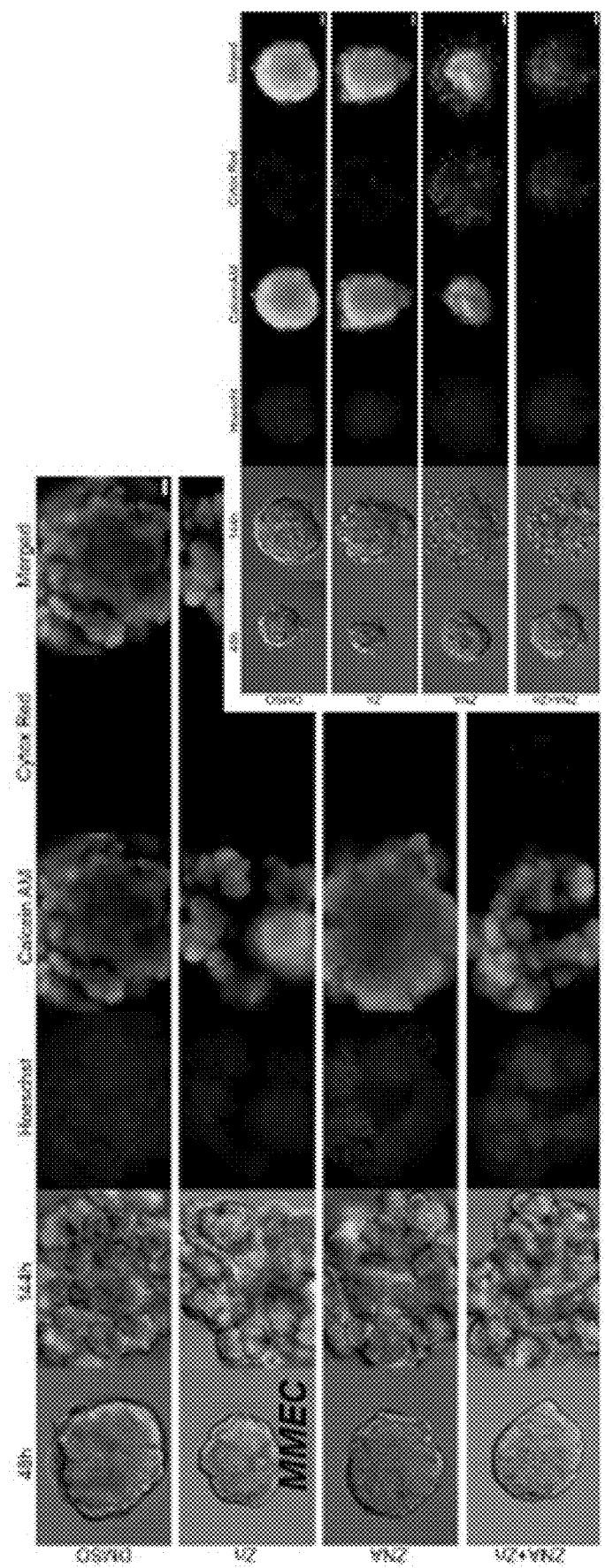
FIG. 8 shows the results of a mammary branching assay.
Figure 9:
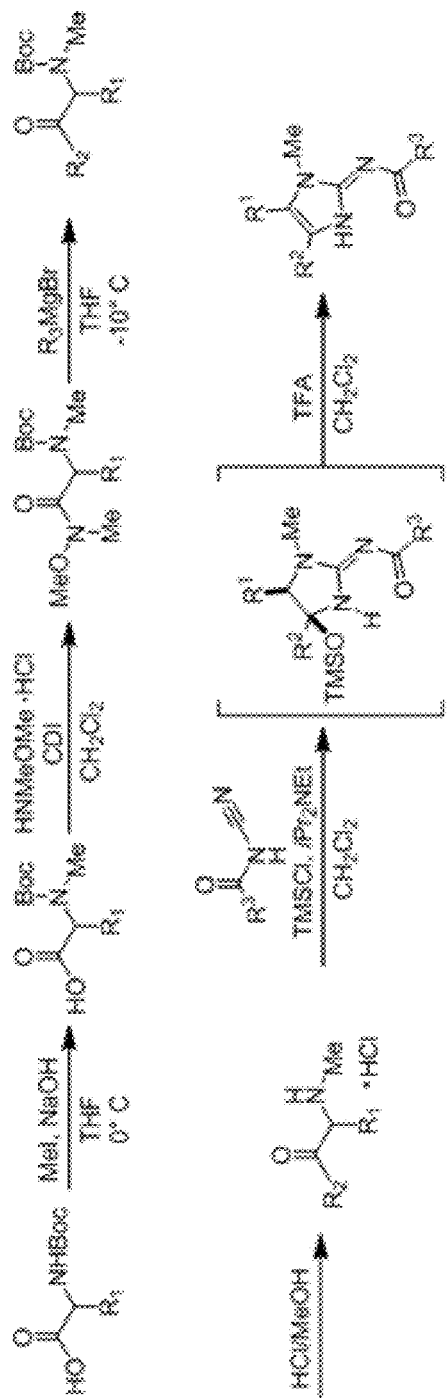
FIG. 9 shows a synthetic route toward 2-N-acyl-4-arylimidazoles (i.e., C$^4$-aryl-N$^2$-acylaminoimidazoles).
Figure 9:
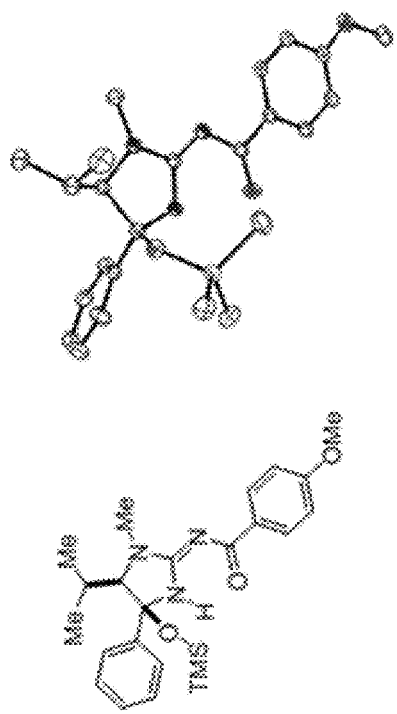
Figure 10:
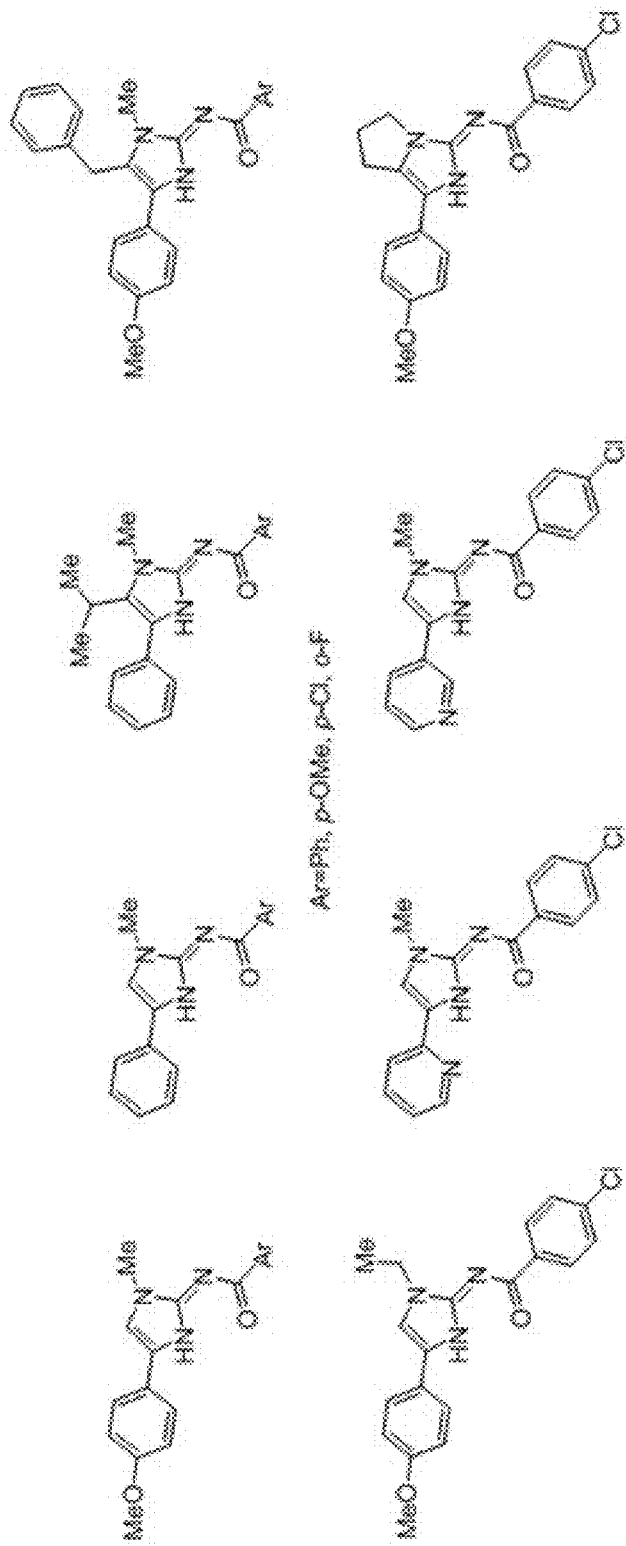
FIG. 10 shows the structures of some analogs.
Figure 11:
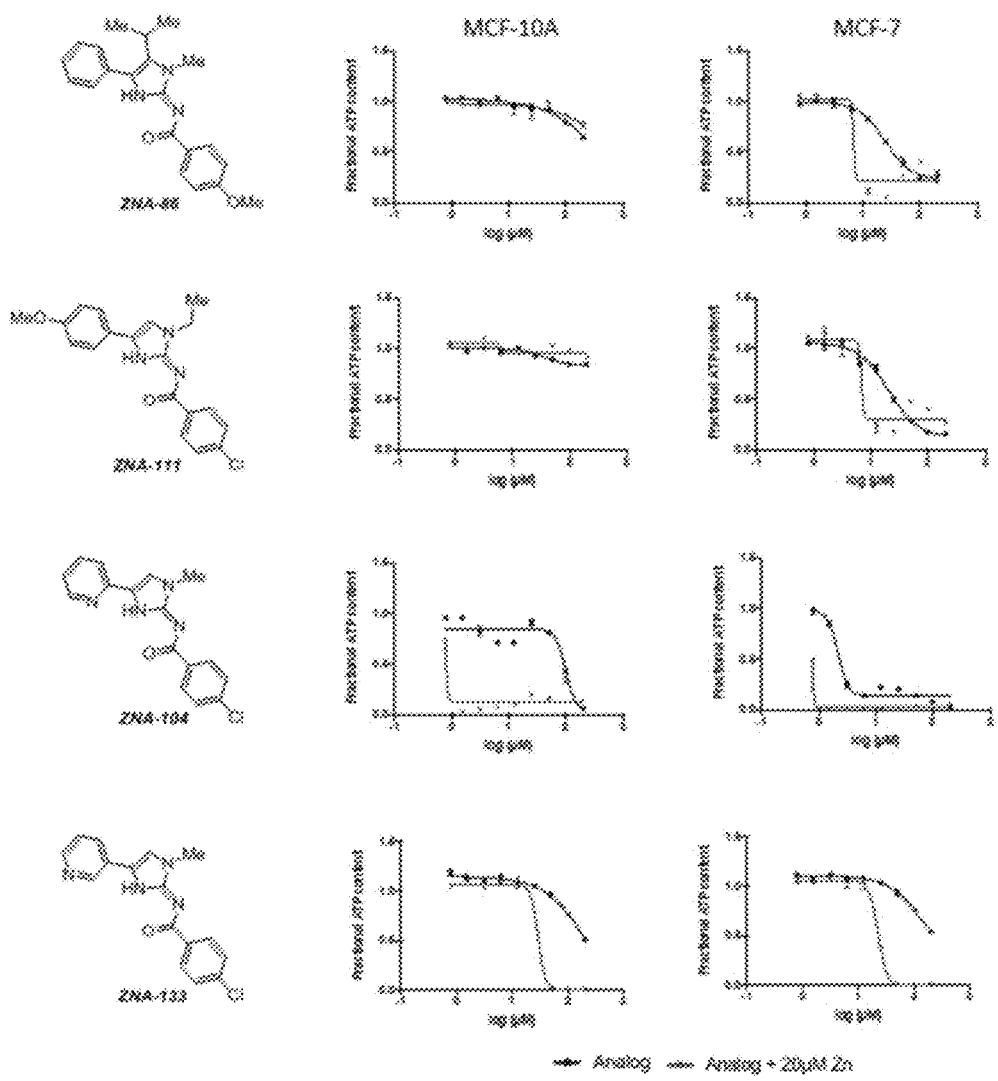
FIG. 11 shows a comparison of the solubility of several ZNA analogs with and without zinc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety, including the U.S. Provisional Appl. No. 62/051,837 and U.S. Pat. Appl. Publ. No. 2013/0197049. In case of conflict, the present specification, including these definitions, will control.

The terms "a," "an," or "the" as used herein not only includes aspects with one member, but also includes aspects with more than one member. For example, an embodiment including "a 2-(acylamino)imidazole and an excipient" should be understood to present certain aspects with at least a second 2-(acylamino)imidazole, at least a second excipient, or both.

The term "about" as used herein to modify a numerical value indicates a defined range around that value. If "X" were the value, "about X" would generally indicate a value from 0.90X to 1.10X. Any reference to "about X" specifically indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to teach and provide written description support for a claim limitation of, e.g., "0.98X." When the quantity "X" only includes whole-integer values (e.g., "X carbons"), "about X" indicates from (X−1) to (X+1). In this case, "about X" as used herein specifically indicates at least the values X, X−1, and X+1.

When the term "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11%" is equivalent to "about 7%, about 9%, or about 11%." However, when the modifier "about" is applied to describe only the end of a range or only a later value in a set of values, it applies only to that value or that end of the range. Thus, the range "about 2 to 10" is the same as "about 2 to about 10," but the range "2 to about 10" is not.

The term "acyl" as used herein includes an alkanoyl, aroyl, heterocycloyl, or heteroaroyl group as defined herein. Examples of acyl groups include, but are not limited to, acetyl, benzoyl, and nicotinoyl.

The term "agent" as used herein includes a compound or mixture of compounds that, when added to a composition, tend to produce a particular effect on the composition's properties. For example, a composition comprising a thickening agent is likely to be more viscous than an otherwise identical comparative composition that lacks the thickening agent.

The term "alkanoyl" as used herein includes an alkyl-C(O)— group wherein the alkyl group is as defined herein. Examples of alkanoyl groups include, but are not limited to, acetyl and propanoyl.

The term "alkenyl" as used herein includes a straight or branched chain hydrocarbon containing at least one carbon-carbon double bond. The chain may contain an indicated number of carbon atoms. For example, "$C_1$-$C_{12}$ alkenyl" indicates that the group may have from 1 to 12 (inclusive) carbon atoms and at least one carbon-carbon double bond. When the indicated number of carbon atoms is 1, then the $C_1$ alkenyl is double bonded to a carbon (i.e., a carbon analog to an oxo group). In certain aspects, the chain includes 1 to 12, about 2 to 15, about 2 to 12, about 2 to 8, or about 2 to 6 carbon atoms. Examples of an alkenyl group may include, but are not limited to, ethenyl (i.e., vinyl), allyl, propenyl, butenyl, crotyl, pentenyl, hexenyl, heptenyl, octenyl, nonenyl, decenyl, dodecenyl, cyclopentenyl, cyclohexenyl, 2-isopentenyl, allenyl, butadienyl, pentadienyl, 3-(1,4-pentadienyl), and hexadienyl.

In some preferred aspects, an alkenyl group is unsubstituted. In some aspects, an alkenyl group is optionally substituted. When optionally substituted, one or more hydrogen atoms of the alkenyl group (e.g., from 1 to 4, from 1 to 2, or 1) may be replaced with a moiety independently selected from the group including fluoro, hydroxy, alkoxy, amino, alkylamino, acylamino, thio, and alkylthio, with the proviso that no hydrogen atom substituent on the carbon-carbon double bond is replaced by a hydroxy, amino, or thio group.

As used herein, the term "alkoxy" refers to a straight or branched chain saturated or unsaturated hydrocarbon containing at least one oxygen atom in an ether group (e.g., EtO—). The chain may contain an indicated number of carbon atoms. For example, "$C_1$-$C_{12}$ alkoxy" indicates that the group may have from 1 to 12 (inclusive) carbon atoms and at least one oxygen atom. Examples of $C_1$-$C_{12}$ alkoxy groups include, but are not limited to, methoxy, ethoxy, isopropoxy, butoxy, n-pentoxy, isopentoxy, neopentoxy, and hexoxy.

An alkoxy group can be unsubstituted or optionally substituted. When optionally substituted, one or more hydrogen atoms of the alkoxy group (e.g., from 1 to 4, from 1 to 2, or 1) may be replaced with one or more moieties independently selected from the group including fluoro, hydroxy, alkoxy, amino, alkylamino, acylamino, thio, and alkylthio, with the proviso that any hydrogen atom alpha to the ether oxygen, if replaced, may only be replaced by fluoro or alkoxy.

The term "alkyl" as used herein includes an aliphatic hydrocarbon chain that may be straight chain or branched. The chain may contain an indicated number of carbon atoms: For example, $C_1$-$C_{12}$ indicates that the group may have from 1 to 12 (inclusive) carbon atoms in it. If not otherwise indicated, an alkyl group about 1 to about 20 carbon atoms. In some aspects, alkyl groups have 1 to about 12 carbon atoms in the chain. In some aspects, alkyl groups ("lower alkyl") have 1 to about 6 carbon atoms in the chain. In some aspects, alkyl groups have 1 to about 4, 3, or 2 carbon atoms in the chain. Examples may include, but are not limited to, methyl, ethyl, propyl, isopropyl (iPr), 1-butyl, 2-butyl, isobutyl (iBu), tert-butyl, pentyl, 2-methylbutyl, 1,1-dimethylpropyl, hexyl, heptyl, octyl, nonyl, decyl, docecyl, cyclopentyl, or cyclohexyl. In some aspects, an alkyl group can exclude methyl (e.g., 2 to 6 carbon atoms in the chain). In some aspects, an alkyl group can be methyl.

An alkyl group can be unsubstituted or optionally substituted. When optionally substituted, one or more hydrogen atoms of the alkyl group (e.g., from 1 to 4, from 1 to 2, or 1) may be replaced with a moiety independently selected from the group including fluoro, hydroxy, alkoxy, amino, alkylamino, acylamino, thio, and alkylthio.

The term "alkynyl" as used herein includes a straight, branched, or cyclic hydrocarbon containing at least one carbon-carbon triple bond. Examples may include, but are not limited to, ethynyl, propargyl, propynyl, butynyl, pentynyl, hexynyl, heptynyl, octynyl, nonynyl, decynyl, or decynyl.

An alkynyl group can be unsubstituted or optionally substituted. When optionally substituted, one or more hydrogen atoms of the alkynyl group (e.g., from 1 to 4, from 1 to 2, or 1) may be replaced with a moiety independently selected from the group including fluoro, hydroxy, alkoxy, amino, alkylamino, acylamino, thio, and alkylthio, with the proviso that no sp hydrogen atom substituent is replaced by a hydroxy, amino, or thio group.

As used herein, the term "2-aminoimidazole" refers to a compound having the general ring formula:

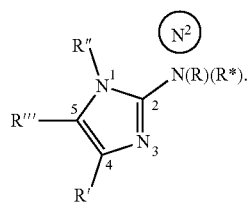

In this formula, "N²" or "N2" references the 2-amino substituent, which is a site for possible reaction (e.g., acylation or diacylation). In some embodiments, a 2-aminoimidazole may be a tautomeric form of general ring formula:

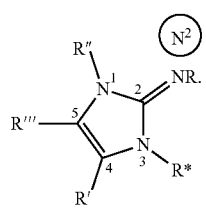

In some aspects of the present application's invention, the ring substituents are as otherwise defined herein (e.g., one of the R groups is acyl; claim 1; and the like).

The term "aroyl" as used herein includes an aryl-CO— group wherein aryl is as defined herein. Examples include, but are not limited to, benzoyl, naphth-1-oyl and naphth-2-oyl.

The term "aryl" as used herein includes cyclic aromatic carbon ring systems containing from 6 to 18 carbons. Examples of an aryl group include, but are not limited to, phenyl, naphthyl, anthracenyl, tetracenyl, biphenyl and phenanthrenyl.

An aryl group can be unsubstituted or optionally substituted. When optionally substituted, one or more hydrogen atoms of the aryl group (e.g., from 1 to 5, from 1 to 2, or 1) may be replaced with a moiety independently selected from the group including alkyl, cyano, acyl, halo, hydroxy, alkoxy, amino, alkylamino, acylamino, thio, and alkylthio.

As used herein, the terms "arylalkyl" and "aralkyl," which are used interchangeably, include an alkyl group as defined herein where at least one hydrogen substituent has been replaced with an aryl group as defined herein. Examples include, but are not limited to, benzyl, 1-phenylethyl, 4-methylbenzyl, and 1,1,-dimethyl-1-phenylmethyl.

As used herein, the term "catalyst" refers to a substance that participates in a chemical reaction so as to increase the rate of the reaction, but that is itself not consumed in the reaction. Examples of catalysts include, but are not limited to, metals, metal oxides, metal complexes, acids, and bases.

A group can be unsubstituted or optionally substituted as per its component parts. For example, but without limitation, the aryl group of an arylalkyl group can be substituted, such as in the arylalkyl group 4-methylbenzyl. In some preferred embodiments, a group includes at most three independently selected optional substituents, and these substituents do no include further optional substituents. In some embodiments, a group includes at most three independently selected optional substituents, but these substituents include further optional substituents.

The linking term "comprising" or "comprise" as used herein is not closed. For example, "a composition comprising A" must include at least the component A, but it may also include one or more other components (e.g., B; B and C; B, C, and D; and the like).

The term "cycloalkyl" as used herein includes a cyclic hydrocarbon group that may contain an indicated number of carbon atoms: For example, $C_3$-$C_{12}$ indicates that the group may have from 3 to 12 (inclusive) carbon atoms in it. If not otherwise indicated, a cycloalkyl group includes about 3 to about 20 carbon atoms. In some aspects, cyclo alkyl groups have 3 to about 12 carbon atoms in the group. In other aspects, cycloalkyl groups have 3 to about 7 carbon atoms in the group. Examples may include, but are not limited to, cyclopropyl, cyclobutyl, cyclopentyl, cyclohexyl, 4,4-dimethylcyclohexyl, and cycloheptyl.

A cycloalkyl group can be unsubstituted or optionally substituted. When optionally substituted, one or more hydrogen atoms of the cycloalkyl group (e.g., from 1 to 4, from 1 to 2, or 1) may be replaced with a moiety independently selected from the group including fluoro, hydroxy, alkoxy, amino, alkylamino, acylamino, thio, and alkylthio. In some aspects, a substituted cycloalkyl group can incorporate an exo- or endocyclic alkene (e.g., cyclohex-2-en-1-yl).

The terms "disorder," "disease," and "condition" are used herein interchangeably for a condition in a subject. A disorder is a disturbance or derangement that affects the normal function of the body of a subject. A disease is a pathological condition of an organ, a body part, or a system resulting from various causes, such as infection, genetic defect, or environmental stress that is characterized by an identifiable group of symptoms.

The term "effective amount" or "effective dose" as used herein includes an amount sufficient to achieve the desired result and accordingly will depend on the ingredient and its desired result. Nonetheless, once the desired effect is identified, determining the effective amount is within the skill of a person skilled in the art.

As used herein, "fluoroalkyl" includes an alkyl group wherein the alkyl group includes one or more fluoro-substituents. Examples include, but are not limited to, trifluoromethyl.

As used herein, "geminal" substitution includes two or more substituents that are directly attached to the same atom. An example is 3,3-dimethyl substitution on a cyclohexyl or spirocyclohexyl ring.

As used herein, "halo" or "halogen" includes fluoro, chloro, bromo, or iodo. In some aspects, "halo" includes fluoro or chloro.

The term "heteroaryl" includes mono and bicyclic aromatic groups of about 4 to about 14 ring atoms (e.g., 4 to 10 or 5 to 10 atoms) containing at least one heteroatom. Heteroatom as used in the term heteroaryl refers to oxygen, sulfur and nitrogen. A nitrogen atom of a heteroaryl is optionally oxidized to the corresponding N-oxide. Examples include, but are not limited to, pyrazinyl, furanyl, thienyl, pyridyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridine, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl.

A heteroaryl group can be unsubstituted or optionally substituted. In some aspects, when optionally substituted, one or more hydrogen atoms of the heteroaryl group (e.g., from 1 to 5, from 1 to 2, or 1) may be replaced with a moiety independently selected from the group including alkyl, cyano, acyl, halo, hydroxy, alkoxy, amino, alkylamino, acylamino, thio, and alkylthio.

The term "heteroaroyl" as used herein includes a heteroaryl-C(O)— group wherein heteroaryl is as defined herein. Heteroaroyl groups include, but are not limited to, thiophenoyl, nicotinoyl, pyrrol-2-ylcarbonyl, and pyridinoyl.

The term "heterocycloyl" as used herein includes a heterocyclyl-C(O)— group wherein heterocyclyl is as defined herein. Examples include, but are not limited to, N-methyl prolinoyl and tetrahydrofuranoyl.

As used herein, "heterocyclyl" includes a non-aromatic saturated monocyclic or multicyclic ring system of about 4 to about 10 ring atoms (e.g., 5 to about 8 ring atoms, or 5 to about 6 ring atoms), in which one or more of the atoms in the ring system is an element or elements other than carbon, e.g., nitrogen, oxygen or sulfur. A heterocyclyl group optionally comprises at least one $sp^2$-hybridized atom (e.g., a ring incorporating an carbonyl, endocyclic olefin, or exocyclic olefin). In some embodiments, a nitrogen or sulfur atom of the heterocyclyl is optionally oxidized to the corresponding N-oxide, S-oxide or S,S-dioxide. Examples of monocyclic heterocyclyl rings include, but are not limited to, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, and tetrahydrothiopyranyl.

A heterocycyl group can be unsubstituted or optionally substituted. When optionally substituted, one or more hydrogen atoms of the group (e.g., from 1 to 4, from 1 to 2, or 1) may be replaced with a moiety independently selected from the group including fluoro, hydroxy, alkoxy, amino, alkylamino, acylamino, thio, and alkylthio. In some aspects, a substituted heterocycyl group can incorporate an exo- or endocyclic alkene.

The term "hydrophobic moiety" or "hydrophobic group" as used herein includes a moiety or a functional group that repels water. Examples may include, but are not limited to, a non-polar moiety, such as an unsubstituted alkyl group having more than five carbons, phenyl group and an anthracenyl group.

As used herein, the terms "hydrophilic moiety" or "hydrophilic group" includes a moiety or a functional group that has a strong affinity to water. Examples may include, but are not limited to, a charged moiety, such as cationic moiety and anionic moiety, or a polar uncharged moiety, such as an alkoxy group and amine group.

As used herein, the term "hydroxyalkyl" includes an alkyl group where at least one hydrogen substituent has been replaced with an alcohol (—OH) group. In certain aspects, the hydroxyalkyl group has one alcohol group. In certain aspects, the hydroxyalkyl group has one or two alcohol groups, each on a different carbon atom. In certain aspects, the hydroxyalkyl group has 1, 2, 3, 4, 5, or 6 alcohol groups. Examples may include, but are not limited to, hydroxymethyl, 2-hydroxyethyl, and 1-hydroxyethyl.

When any two substituent groups or any two instances of the same substituent group are "independently selected" from a list of alternatives, the groups may be the same or different. For example, if $R^a$ and $R^b$ are independently selected from the group including alkyl, fluoro, amino, and hydroxyalkyl, then a molecule with two $R^a$ groups and two $R^b$ groups could have all groups be alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different).

As used herein, "or" should in general be construed non-exclusionarily. For example, an embodiment of "a composition comprising A or B" would typically present one or more aspects with a composition comprising both A and B. "Or" should, however, be construed to exclude those aspects presented that cannot be combined without contradiction (e.g., a composition pH that is between 9 and 10 or between 7 and 8).

As used herein, the term "salt" refers to acid or base salts of a compound, e.g., ZNA or another 2-(acylamino)imidazole. Illustrative examples of pharmaceutically acceptable salts are cationic salts such as alkali and alkaline earth metal (such as sodium, lithium, potassium, calcium, and magnesium) salts, ammonium (ammonium, trimethyl ammonium, diethylammonium, and tris-(hydroxymethyl)-methyl-ammonium) salts, mineral acid (hydrochloric acid, hydrobromic acid, phosphoric acid, and the like) salts, organic carboxylic acid (acetic acid, propionic acid, glutamic acid, citric acid, and the like) salts, organic sulfonic acid (methanesulfonic acid) salts, and quaternary ammonium (methyl iodide, ethyl iodide, and the like) salts. Additional information on suitable pharmaceutically acceptable salts can be found in Remington's, Pharmaceutical Sciences (current edition), Mack Publishing Co., Easton, Pa., which is incorporated herein by reference.

The terms "a salt thereof," "salt thereof," or "salts thereof" can be applied to any preceding member of an associated Markush group. For example, a group consisting of A, B, C, and salts thereof would include within its scope embodiments that were a salt of A, embodiments that were a salt of B, and embodiments that were a salt of C.

As used herein, "spirocycloalkyl" as used herein includes a cycloalkyl in which geminal substituents on a carbon atom are replaced to join in forming a 1,1-substituted ring. For example, but without limitation, for a —C($R^1$)($R^2$)— group that was part of a longer carbon chain, if $R^1$ and $R^2$ joined to form a cyclopropyl ring incorporating the carbon to which $R^1$ and $R^2$ were bonded, this would be a spirocycloalkyl group (i.e., spirocyclopropyl).

As used herein, "spiroheterocyclyl" as used herein includes a heterocycloalkyl in which geminal substituents on a carbon atom are replaced to join in forming a 1,1-substituted ring. For example, but without limitation, for a —C($R^1$)($R^2$)— group that was part of a longer carbon chain, if $R^1$ and $R^2$ joined to form a pyrrolidine ring incorporating the carbon to which $R^1$ and $R^2$ were bonded, this would be a spiroheterocyclyl group.

As used herein, the term "treat," "treating," or "treatment" includes administering or applying a composition (e.g., a composition described herein) in an amount, manner (e.g., schedule of administration), and mode (e.g., route of administration) that is effective to improve a disorder or a symptom thereof, or to prevent, to retard, or to slow the progression of a disorder or a symptom thereof. Such improvements can include, but are not limited to, alleviation or amelioration of one or more symptoms or conditions, diminishment of the extent of a disease, stabilizing (i.e., not worsening) the state of disease, prevention of a disease's transmission or spread, delaying or slowing of disease progression, amelioration or palliation of the disease state, diminishment of the reoccurrence of disease, and remission, whether partial or total and whether detectable or undetectable.

"Treating" and "treatment" as used herein also include prophylactic treatment. In certain embodiments, treatment methods comprise administering to a subject a therapeutically effective amount of an active agent. The administering step may consist of a single administration or may comprise a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some aspects, chronic administration may be required. For example, the compositions are administered to the subject in an amount, and for a duration, sufficient to treat the patient.

In the Summary of the Invention above, Detailed Description, and the claims below, reference is made to particular features and aspects of the invention, including method steps. The disclosure of the invention in this specification includes all possible combinations of such particular features within the embodiments of the invention disclosed, at least to the extent that such combinations are non-contradictory. For example, if the Detailed Description presents aspects A, B, and C of an embodiment, it is understood that this also discloses particular embodiments including both aspects A and B, both aspects B and C, and both aspects A and C, as well as an embodiment with aspects A, B, and C.

Compositions

In a first embodiment, the invention presents a 2-(acylamino)imidazole compound selected from the group including:

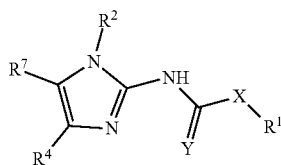

I or a salt thereof;
wherein:
$R^1$ is a member selected from the group consisting of alkyl, alkenyl, alkynyl, aryl, arylalkyl, heteroaryl, and heteroarylalkyl;
X is a member selected from the group consisting of a bond, O, and $NR^{5a}$;
Y is a member selected from the group consisting of O, S, or $NR^{5b}$; or, when X is O or a bond, Y is O;
$R^2$ is a member independently selected from the group consisting of alkyl, alkenyl, alkynyl, and arylalkyl; or, alternatively, $R^2$ and $R^7$ join to form an additional heterocyclyl fused ring;
$R^4$ is a member independently selected from the group consisting of aryl and heteroaryl, wherein $R^4$ has from one to five $R^{6a}$ substituents;
$R^{5a}$ and $R^{5b}$ are each a member independently selected from the group consisting of hydrogen, alkyl, fluoroalkyl, alkenyl, alkynyl, cycloalkyl, cycloalkylalkyl, arylalkyl, and heteroarylalkyl;
each of the $R^{6n}$ members is independently selected from the group consisting of hydrogen, alkyl, hydroxy, alkoxy, aminoalkoxy, alkylamino, alkylaminoalkoxy, alkenyl, alkynyl, aryl, aryloxy, arylamino, cycloalkyl, cycloalkylalkyl, cycloalkoxy, cycloalkylalkoxy, cycloalkylamino, cycloalkylalkylamino, heterocyclyl, heterocycyloxy, heterocycyalkyloxy, heterocycyamino, heterocycyalkylamino, halo, haloalkyl, fluoroalkyloxy, arylalkyl, arylalkyloxy, arylalkylamino, heteroaryl, heteroaryloxy, heteroarylamino, heteroarylalkyl, heteroarylalkyloxy, and heteroarylalkylamino; or, alternatively, a pair of adjacent $R^{6n}$ members join to form an additional fused ring that is selected from the group consisting of cycloalkyl, aryl, heterocyclyl, and heterocycloaryl; and
$R^7$ is a member independently selected from the group consisting of hydrogen, halo, trifluoromethyl, and alkyl; or, alternatively, $R^2$ and $R^7$ join to form an additional heterocyclyl fused ring;
wherein the 2-(acylamino)imidazole compound is not a natural product.

In some aspects, if $R^1$ is aryl, arylalkyl, heteroaryl, or heteroarylalkyl, then $R^1$ is unsubstituted or optionally substituted with from one to five substituents independently selected from the group consisting of alkyl, cyano, acyl, halo, hydroxy, alkoxy, amino, alkylamino, acylamino, thio, and alkylthio. In certain aspects, $R^1$ is unsubstituted.

In some aspects, the invention sets forth the composition described above, wherein $R^4$ is heteroaryl. In some more specific aspects, the $R^4$ heteroaryl ring incorporates at least one hydrogen bond acceptor selected from the group including N, O, and S.

In some more specific aspects, the hydrogen bond acceptor is O. In some aspects, $R^4$ is furanyl substituted with three independently selected $R^{6n}$ (e.g., H). In some aspects, $R^4$ is oxazolyl substituted with two independently selected $R^{6n}$ (e.g., H).

In some more specific aspects, the hydrogen bond acceptor is S. In some aspects, $R^4$ is thiophenyl substituted with three independently selected $R^{6n}$ (e.g., H). In some aspects, $R^4$ is thiazolyl substituted with two independently selected $R^{6n}$ (e.g., H).

In some preferred more specific aspects, the hydrogen bond acceptor is N. In some aspects, $R^4$ is unsubstituted. In some aspects, $R^4$ is pyridyl substituted with four independently selected $R^{6n}$. In some aspects, $R^4$ is pyrazinyl substituted with three independently selected $R^{6n}$. In some aspects, $R^4$ is pyrimidinyl substituted with three independently selected $R^{6n}$. In some aspects, $R^4$ is imidazolyl substituted with three independently selected $R^{6n}$. In some aspects, $R^4$ is pyrazolyl substituted with three independently selected $R^{6n}$. In some aspects, $R^4$ is oxazolyl substituted with two independently selected $R^{6n}$. In some aspects, $R^4$ is thiazolyl substituted with two independently selected $R^{6n}$.

In some more specific aspects, $R^4$ is selected from the group including

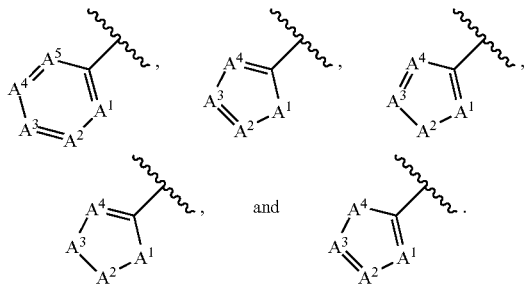

In some more specific aspects, $A^1$ is a hydrogen bond acceptor selected from the group including N, O, and S.

In some more specific aspects, $A^1$ is a hydrogen bond acceptor N. In some more specific aspects, $A^1$ is a hydrogen bond acceptor O. In some more specific aspects, $A^1$ is a hydrogen bond acceptor S. As would be apparent to the skilled artisan, a hydrogen bond acceptor has at least one electron pair that is suitable for forming a hydrogen bond. In some preferred aspects, the hydrogen bond acceptor is a Lewis base that is suitable for coordinating a metal ion (e.g., a zinc cation).

In some more specific aspects, $A^2$, $A^3$, $A^4$, and $A^5$ are each independently selected from the group including N, O, S, CH, and $CR^{6n}$; with the proviso that $R^4$ does not have a formal charge (e.g., when $A^2$ in the structure above is O, it can be $A^3$-$O^0$-$A^1$, but not $A^3$=$O^{+1}$-$A^1$ or $A^3$-$O^{+1}$=$A^1$). In some aspects, $A^2$, $A^3$, $A^4$, and $A^5$ are each an independently selected CH or $CR^{6n}$. In some aspects, one of $A^2$, $A^3$, $A^4$, and $A^5$ is selected from the group including N, O, and S, and the remaining A groups are each an independently selected CH or $CR^{6n}$.

In some more specific aspects, $R^4$ is selected from the group consisting of pyridyl, pyrazinyl, imidazolyl, pyrazinyl, and oxazoyl. In certain aspects, $R^4$ is unsubstituted. In certain aspects, $R^4$ has from one to four $R^{6n}$ substituents.

In some aspects, the 2-aminoimidazole compound is substantially free from an impurity selected from the group including

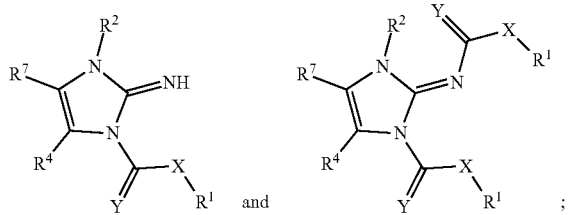

or a salt thereof.

In preferred aspects, "substantially free" denotes <2% of the impurity; more preferably, <1% of the impurity; and still more preferably, <0.2% of the impurity.

In some aspects, $R^1$ is a member selected from the group including alkyl, aryl, arylalkyl, and heteroaryl. In some preferred aspects, if $R^1$ is aryl, arylalkyl, heteroaryl, or heteroarylalkyl, then $R^1$ is unsubstituted or optionally substituted with from one to five substituents independently selected from the group consisting of alkyl, cyano, acyl, halo, hydroxy, alkoxy, amino, alkylamino, acylamino, thio, and alkylthio. In some more specific aspects, $R^1$ is a member selected from the group including isopropyl, sec-butyl, phenyl, 2-bromophenyl, 4-chlorophenyl, 2,4-dichlorophenyl, 2,5-dichlorophenyl, 2-fluorophenyl, 4-fluorophenyl, 4-methoxyphenyl, 3,4-methylenedioxyphenyl, 3-trifluoromethylphenyl, and 2-thiazolyisopropyl. In some more specific aspects, $R^1$ is a member selected from the group including sec-butyl, phenyl, 2-fluorophenyl, 2,4-dichlorophenyl, and 2-thiazolyl. In some more specific aspects, $R^1$ is a member selected from the group including phenyl, 2-fluorophenyl, 3-trifluoromethylphenyl, 4-chlorophenyl, 4-methoxyphenyl, and cyclopropyl.

In some aspects, $R^1$ is alkyl. In some more specific aspects, $R^1$ is methyl, ethyl, isopropyl, sec-butyl, or tert-butyl. In some more specific aspects, $R^1$ is isopropyl or sec-butyl. In some more specific aspects, $R^1$ is tert-butyl.

In some aspects, $R^1$ is alkenyl. In some more specific aspects, $R^1$ is allyl or methallyl.

In some aspects, $R^1$ is alkynyl. In some more specific aspects, $R^1$ is propargyl.

In some aspects, $R^1$ is aryl. In some more specific aspects, $R^1$ is phenyl. In some alternative aspects, $R^1$ is haloaryl (e.g., halophenyl). In some more specific aspects, $R^1$ is 2-fluorophenyl or 2,4-dichlorophenyl. In some more specific aspects, $R^1$ is 4-halophenyl (e.g., 4-chlorophenyl).

In some aspects, $R^1$ is arylalkyl. In some more specific aspects, $R^1$ is benzyl.

In some aspects, $R^1$ is heteroaryl. In some more specific aspects, $R^1$ is 4-, 3-, or 2-pyridyl.

In some aspects, $R^1$ is heteroarylalkyl. In some more specific aspects, $R^1$ is 4-, 3-, or 2-pyridylmethyl.

In some preferred aspects, X is a bond. In some alternative aspects, X is O. In some alternative aspects, X is $NR^{5a}$.

In some aspects, Y is O. In some alternative aspects, Y is $NR^{5b}$.

In some aspects, $R^7$ is a member independently selected from the group including hydrogen, halo, trifluoromethyl, and alkyl; or, alternatively, $R^2$ and $R^7$ join to form an additional heterocyclyl fused ring.

In some aspects, $R^2$ is a member selected from the group including alkyl, alkenyl, and arylalkyl. In some aspects, $R^2$ is alkyl. In some more specific aspects, $R^2$ is methyl. In some more specific aspects, $R^2$ is ethyl. In some aspects, $R^2$ is allyl.

In some aspects, $R^2$ and $R^7$ join to form an additional heterocyclyl fused ring. In some aspects, R2 and R7 are linked by —$(CR^{3a}R^{3b})_n$—, wherein n is an integer from 2 to 4 (preferably, 2 or 3); and wherein each $R^{3a}$ and $R^{3b}$ is independently selected from the group consisting of hydrogen, lower alkyl, lower fluoroalkyl, alkenyl, alkynyl, and fluoro; or, alternatively, a geminal $R^{3a}$ and $R^{3b}$ combine to form an oxo-group.

In some aspects, $R^{5a}$ and $R^{5b}$ are each a member independently selected from the group including hydrogen, alkyl, fluoroalkyl, alkenyl, alkynyl, cycloalkyl, cycloalkylalkyl, arylalkyl, and heteroarylalkyl.

In some aspects, $A^1$, $A^2$, $A^3$, $A^4$, and $A^5$ are each an independently selected CH or $CR^{6n}$. In some alternative aspects, only one of $A^1$, $A^2$, $A^3$, $A^4$, and $A^5$ is N. In some alternative aspects, only two members selected from the group including $A^1$, $A^2$, $A^3$, $A^4$, and $A^5$ are N. In some alternative aspects, only three members selected from the group including $A^1$, $A^2$, $A^3$, $A^4$, and $A^5$ are N.

In some aspects, each of the $R^{6a}$ members is independently selected from the group including alkyl, hydroxy, alkoxy, aryl, aryloxy, cycloalkyl, cycloalkoxy, cycloalkylalkoxy, heterocyclyl, heterocycyloxy, heterocycylalkyloxy, halo, fluoroalkyl, fluoroalkyloxy, heteroaryl, heteroaryloxy, arylalkyl, arylalkyloxy, arylalkylamino, and heteroarylalkyloxy. In some aspects, each of the $R^{6n}$ members is independently selected from the group including alkyl, hydroxy, alkoxy, cycloalkylalkoxy, halo, fluoroalkyl, fluoroalkyloxy, and arylalkyloxy. In some aspects, $R^4$ is unsubstituted (i.e., hydrogen substitution).

In some aspects, each of the $R^{6n}$ members is independently selected from the group including alkyl, hydroxy, alkoxy, aryl, aryloxy, cycloalkyl, cycloalkoxy, cycloalkylalkoxy, heterocyclyl, heterocycyloxy, halo, fluoroalkyl, fluoroalkyloxy, heteroaryl, heteroaryloxy, arylalkyl, arylalkyloxy, arylalkylamino, and heteroarylalkyloxy. In some aspects, each of the $R^{6n}$ members is independently selected from the group including alkyl, hydroxy, alkoxy, cycloalkylalkoxy, halo, fluoroalkyl, fluoroalkyloxy, and arylalkyloxy. In some aspects, each of the $R^{6n}$ members is independently selected from the group including alkyl, hydroxy, and alkoxy. In some aspects, $R^4$ is unsubstituted (i.e., hydrogen substitution).

In some aspects,

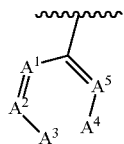

has from one to three hydroxyl or alkyoxy substituents.

In some aspects, $A^3$ is C(OH) or C(OMe). In some alternative aspects, $A^3$ is CH, CCl, C(OMe), or

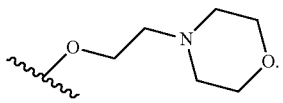 [SMILES: *OCCN1CCOCC1]

In some aspects, the $R^4$ group has one $R^{6n}$ substitutent. In some more specific aspects, the $R^4$ group is bicyclic (e.g., naphthyl; indolyl). In some still more specific aspects, at least six of the $R^4$ substituents are hydrogen. In some still more specific aspects, at least eight of the $R^4$ substituents are hydrogen.

In some aspects, $R^7$ is a member independently selected from the group including hydrogen, halo, trifluoromethyl, and alkyl; or, alternatively, $R^2$ and $R^7$ join to form an additional heterocyclyl fused ring.

In some aspects, $R^7$ is alkyl or hydrogen. In some aspects, $R^7$ is hydrogen. In some aspects, $R^7$ is alkyl (e.g., $C_1$-$C_4$ alkyl or $C_1$-$C_3$ alkyl). In some aspects, $R^7$ is methyl. In some aspects, $R^7$ is isopropyl.

In some aspects, $R^7$ is aminoalkyl or alkylaminoalkyl. In some more specific aspects, $R^7$ is morpholinylmethyl.

In some more specific aspects, the invention sets forth the composition comprising a 2-(acylamino)imidazole compound

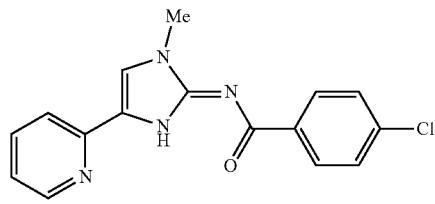 [SMILES: Cn1cc(-c2ccccn2)[nH]/c1=N\C(=O)c1ccc(Cl)cc1]

or a salt thereof.

In some aspects,

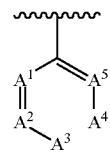

is a phenol. In some more specific aspects,

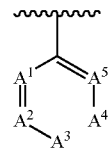

is a p-phenol (e.g., 4-hydroxyphenyl).

In some aspects,

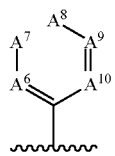

is a phenol. In some more specific aspects,

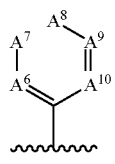

is a p-phenol (e.g., 4-hydroxyphenyl).

In some aspects, the invention sets forth a compound selected from those in Table I and salts thereof.

From a structural standpoint, the N-Me-hydantoin derived headgroup of naamidine A or a similar compound might well serve as a canonical 2-point kinase binder (analogous to a 2-aminopyridine). See Yoon et al. *Invest. Ophthalmol. Vis. Sci.* 2010; Enzenmuller et al. *Anticancer drugs* 2013, 24 (1), 14-9; Xue et al. *PLoS One* 2014, 9 (10), e109180/1-e109180/6, 6 pp. The hydantoin headgroup might also serve as a highly promiscuous binder (similar to the rhodanines and other hydantoins) contributing to significant "off-target" effects. See Ding et al. *Cancer Res.* 2005, 65 (8), 3389-3395; Lind et al. *Transl. Res.* 2009, 154 (3), 153-159; Yu et al. *Biochem. J* 2009, 417 (1), 133-139; Takeda et al. *PLoS One* 2011, 6 (12), e28615; Jiang et al. *Cancer Lett.* 2011, 312 (1), 11-17; Park et al. *Neurobiol. Dis.* 2011, 42 (3), 242-51; Cao et al. *Sci Rep* 2014, 4. Advantageously, these effects should be minimized or avoided in the structurally simpler series of $N^2$-acyl-2-aminoimidazoles of the claimed invention.

Methods of Treatment

In a second embodiment, the invention presents a method of killing bacteria in vitro, the method comprising treating the bacteria with a composition set forth in the first embodiment or one of its aspects. In some alternative aspects of those presented, the invention presents a compound or composition for use in such a method.

In a third embodiment, the invention presents a method of killing bacteria in vivo, the method comprising administering a composition set forth in the first embodiment or one of its aspects to a patient. In some alternative aspects of those presented, the invention presents a compound or composition for use in such a method.

In a fourth embodiment, the invention presents a method of treating cancer, the method comprising administering a composition set forth in the first embodiment or one of its aspects to a patient with cancer, thereby treating the patient. In some alternative aspects of those presented, the invention presents a compound or composition for use in such a method.

Without intending to be bound by theory, the method of action for the inventive compounds and compositions may include modulation of zinc metabolism. Zinc is an essential trace metal. Bioinformatic studies have estimated that 10% of the proteome may bind zinc, 40% of these proteins functioning as transcription factors and the remaining 60% functioning in an enzymatic or an ion transport capacity (15). Considering the ubiquitous nature of the ion and the necessity of zinc for proper cellular function, it is not surprising then that perturbations in zinc homeostasis are correlated with varying disease states: Zinc accumulation has been found to occur in conjunction with the formation of Alzheimer's disease-associated extracellular plaques and increased zinc levels have been observed in malignant breast tissue compared to nonmalignant tissue (16-18). Exploiting the differences in zinc homeostasis between healthy and diseased tissue could provide a beneficial treatment window for therapeutics.

In some aspects, the methods of treating cancer comprise the compound ZNA. As the Examples show, ZNA synergizes strongly with $Zn^{2+}$ to induce cancer-selective cell death via a caspase-independent mechanism. ZNA was found to be effective against primary metastatic cells derived from breast cancer patients treated with multiple frontline chemotherapeutics, and the small molecule's in vivo efficacy was established using a mouse mammary tumor model. Taken together, the Examples suggest that destabilizing $Zn^{2+}$ trafficking pathways and inducing intracellular $Zn^{2+}$ dyshomeostasis are viable mechanisms by which to selectively target breast cancer. Furthermore, ZNA's activity against chemoresistant patient-derived tumor cells, which model the molecular and genomic characteristics of breast cancer following patient treatment initiation, suggests that the affected pathways are clinically relevant in vivo.

In some embodiments, the invention presents a composition for therapeutic use, the composition including a 2-(acylamino)imidazole of one of the aspects herein. In some aspects, the composition further includes a pharmaceutically acceptable excipient.

In instances where the 2-(acylamino)imidazole compound is to be administered to a subject, the compounds can be incorporated into pharmaceutical compositions. The 2-(acylamino)imidazole compound can be incorporated into pharmaceutical compositions as pharmaceutically acceptable salts or derivatives. Some pharmaceutically acceptable derivatives of the 2-(acylamino)imidazole compounds of the present invention may include a chemical group that increases aqueous solubility. As used herein, a "pharmaceutically acceptable carrier" means a substance that can be administered to a subject together with a 2-(acylamino) imidazole compound or salt thereof (i.e., as a carrier), or a combination of a 2-(acylamino)imidazole compound (or salt thereof) with another compound, and that does not destroy the pharmacological activity thereof. Pharmaceutically acceptable carriers include, for example, solvents, binders, dispersion media, coatings, preservatives, colorants, isotonic and absorption delaying agents, and the like that are compatible with pharmaceutical administration. Supplementary active compounds can also be incorporated into the compositions.

Non-limiting examples of pharmaceutically acceptable carriers that can be used include poly(ethylene-co-vinyl acetate), PVA, partially hydrolyzed poly(ethylene-co-vinyl acetate), poly(ethylene-co-vinyl acetate-co-vinyl alcohol), a cross-linked poly(ethylene-co-vinyl acetate), a cross-linked partially hydrolyzed poly(ethylene-co-vinyl acetate), a cross-linked poly(ethylene-co-vinyl acetate-co-vinyl alcohol), poly-D,L-lactic acid, poly-L-lactic acid, polyglycolic acid, PGA, copolymers of lactic acid and glycolic acid (PLGA), polycaprolactone, polyvalerolactone, poly(anhydrides), copolymers of polycaprolactone with polyethylene glycol, copolymers of polylactic acid with polyethylene glycol, polyethylene glycol; and combinations and blends thereof.

Other carriers include, e.g., an aqueous gelatin, an aqueous protein, a polymeric carrier, a cross-linking agent, or a combination thereof. In other instances, the carrier is a matrix. In yet another instances, the carrier includes water, a pharmaceutically acceptable buffer salt, a pharmaceutically acceptable buffer solution, a pharmaceutically acceptable antioxidant, ascorbic acid, one or more low molecular weight pharmaceutically acceptable polypeptides, a peptide comprising about 2 to about 10 amino acid residues, one or more pharmaceutically acceptable proteins, one or more pharmaceutically acceptable amino acids, an essential-to-human amino acid, one or more pharmaceutically acceptable carbohydrates, one or more pharmaceutically acceptable carbohydrate-derived materials, a non-reducing sugar, glucose, sucrose, sorbitol, trehalose, mannitol, maltodextrin, dextrins, cyclodextrin, a pharmaceutically acceptable chelating agent, EDTA, DTP A, a chelating agent for a divalent metal ion, a chelating agent for a trivalent metal ion, glutathione, pharmaceutically acceptable nonspecific serum albumin, or combinations thereof.

The route of administration of a therapeutic agent (e.g., a therapeutically active 2-(acylamino)imidazole or a salt thereof) can be oral, intraperitoneal, transdermal, subcutaneous, by intravenous or intramuscular injection, by inhalation, topical, intralesional, infusion; liposome-mediated delivery; topical, intrathecal, gingival pocket, rectal, intrabronchial, nasal, transmucosal, intestinal, ocular or otic delivery, or any other methods known in the art. In some aspects, the 2-(acylamino)imidazole therapeutic agent or a salt thereof is administered orally, intravenously, or intraperitoneally.

In some aspects, the 2-(acylamino)imidazole therapeutic agent or a salt thereof is administered at a therapeutically effective amount or dose. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied according to several factors, including the chosen route of administration, the formulation of the composition, patient response, the severity of the condition, the subject's weight, and the judgment of the prescribing physician. The dosage can be increased or decreased over time, as required by an individual patient. In certain instances, a patient initially is given a low dose, which is then increased to an efficacious dosage tolerable to the patient. Determination of an effective amount is well within the capability of those skilled in the art.

In some aspects, 2-(acylamino)imidazole therapeutic agent or a salt thereof is administered in combination with a second therapeutic agent. In some aspects, the second therapeutic agent is a chemotherapeutic agent. In some aspects, the chemotherapeutic agent is an alkylating agent (e.g., cyclophosphamide, ifosfamide, chlorambucil, busulfan, melphalan, mechlorethamine, uramustine, thiotepa, nitrosoureas, or temozolomide), an anthracycline (e.g., doxorubicin, adriamycin, daunorubicin, epirubicin, or mitoxantrone), a cytoskeletal disruptor (e.g., paclitaxel or docetaxel), a histone deacetylase inhibitor (e.g., vorinostat or romidepsin), an inhibitor of topoisomerase (e.g., irinotecan, topotecan, amsacrine, etoposide, or teniposide), a kinase inhibitor (e.g., bortezomib, erlotinib, gefitinib, imatinib, vemurafenib, or vismodegib), a nucleoside analog or precursor analog (e.g., azacitidine, azathioprine, capecitabine, cytarabine, fluorouracil, gemcitabine, hydroxyurea, mercaptopurine, methotrexate, or thioguanine), a peptide antibiotic (e.g., actinomycin or bleomycin), a platinum-based agent (e.g., cisplatin, oxaloplatin, or carboplatin), or a plant alkaloid (e.g., vincristine, vinblastine, vinorelbine, vindesine, podophyllotoxin, paclitaxel, or docetaxel). In some aspects, the chemotherapeutic agent is gemcitabine.

Co-administered therapeutic agents (e.g., a 2-(acylamino) imidazole therapeutic agent or a salt thereof, and a second therapeutic agent as described herein) can be administered together or separately, simultaneously or at different times. When administered, the therapeutic agents independently can be administered once, twice, three, or four times daily, or more or less often, as needed. In some aspects, the administered therapeutic agents are administered once daily. In some aspects, the administered therapeutic agents are administered at the same time or times, for instance as an admixture. In some aspects, one or more of the therapeutic agents is administered in a sustained-release formulation.

In some aspects, an 2-(acylamino)imidazole therapeutic agent or a salt thereof, and a second therapeutic agent are administered concurrently. In some aspects, the 2-(acylamino)imidazole therapeutic agent or salt thereof is administered first, for example for about 1, 2, 3, 4, 5, 6, 7, 8, 9, 10, 15, 20, 25, 30, 40, 50, 60, 70, 80, 90, 100 days or more prior to administering the second therapeutic agent (e.g., chemotherapeutic agent). In some aspects, the second therapeutic agent (e.g., chemotherapeutic agent) is administered first, for example for about 1, 2, 3, 4, 5, 6, 7, 8, 9, 10, 15, 20, 25, 30, 40, 50, 60, 70, 80, 90, 100 days or more prior to administering the 2-(acylamino)imidazole therapeutic agent or salt thereof.

In some aspects, a 2-(acylamino)imidazole therapeutic agent or a salt thereof (and optionally a second therapeutic agent, e.g., a chemotherapeutic agent as described herein) is administered to the subject over an extended period of time, e.g., for at least 30, 40, 50, 60, 70, 80, 90, 100, 150, 200, 250, 300, 350 days or longer.

In other aspects, compositions and kits for use in treating or preventing a cancer in a subject are provided.

In some aspects, compositions and kits for treating a cancer are provided. In some embodiments, the composition or kit comprises:

a composition set forth in the first embodiment or one of its aspects.

In some aspects, pharmaceutical compositions comprising a 2-(acylamino)imidazole therapeutic agent or a salt thereof, for use in administering to a subject having a cancer are provided. In some aspects, the 2-(acylamino)imidazole therapeutic agent or salt thereof is as described above. In some aspects, a 2-(acylamino)imidazole therapeutic agent or a salt thereof, and a second therapeutic agent (e.g., a chemotherapeutic agent as described herein) are formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols.

Guidance for preparing formulations for use in the present invention is found in, for example, in *Remington: The Science and Practice of Pharmacy*, 21$^{st}$ Ed., 2006, supra; *Martindale: The Complete Drug Reference*, Sweetman, 2005, London: Pharmaceutical Press; Niazi, *Handbook of Pharmaceutical Manufacturing Formulations*, 2004, CRC Press; and Gibson, *Pharmaceutical Preformulation and Formulation: A Practical Guide from Candidate Drug Selection to Commercial Dosage Form*, 2001, Interpharm Press, which are hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In some aspects, a 2-(acylamino)imidazole therapeutic agent or a salt thereof (and optionally a second therapeutic agent, e.g, a chemotherapeutic agent as described herein) is prepared for delivery in a sustained-release, controlled release, extended-release, timed-release or delayed-release formulation, for example, in semi-permeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

For oral administration, a 2-(acylamino)imidazole therapeutic agent or a salt thereof (and optionally a second therapeutic agent, e.g, a chemotherapeutic agent as described herein) can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

The 2-(acylamino)imidazole therapeutic agent or salt thereof (and optionally a second therapeutic agent, e.g., a chemotherapeutic agent as described herein) can be formulated for parenteral administration by injection, e.g., by bolus injection or continuous infusion. For injection, the compound or compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. In some aspects, compounds can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

The 2-(acylamino)imidazole therapeutic agent or salt thereof (and optionally a second therapeutic agent, e.g., a chemotherapeutic agent as described herein) can be administered systemically by transmucosal or transdermal means. For transmucosal or transdermal administration, penetrants appropriate to the barrier to be permeated are used in the formulation. For topical administration, the agents are formulated into ointments, creams, salves, powders and gels. In some aspects, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplary transdermal delivery formulations include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

In some aspects, a pharmaceutical composition comprises an acceptable carrier and/or excipients. A pharmaceutically acceptable carrier includes any solvents, dispersion media, or coatings that are physiologically compatible and that preferably do not interfere with or otherwise inhibit the activity of the therapeutic agent. In some aspects, the carrier is suitable for intravenous, intramuscular, oral, intraperitoneal, transdermal, topical, or subcutaneous administration. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of the active agents, or excipients or other stabilizers and/or buffers. Other pharmaceutically acceptable carriers and their formulations are well-known and generally described in, for example, *Remington: The Science and Practice of Pharmacy*, 21st Edition, Philadelphia, Pa. Lippincott Williams & Wilkins, 2005. Various pharmaceutically acceptable excipients are well-known in the art and can be found in, for example, Handbook of Pharmaceutical Excipients ($5^{th}$ ed., Ed. Rowe et al., Pharmaceutical Press, Washington, D.C.).

In some aspects, kits for use in administering to a subject having a cancer are provided. In some aspects, the kit comprises:

a 2-(acylamino)imidazole therapeutic agent or a salt thereof; and a second therapeutic agent.

In some aspects, the 2-(acylamino)imidazole therapeutic agent or salt thereof is as described above. In some aspects, the second therapeutic agent is a chemotherapeutic agent. In some aspects, the chemotherapeutic agent is an alkylating agent, an anthracycline, a cytoskeletal disruptor, a histone deacetylase inhibitor, an inhibitor of topoisomerase, a kinase inhibitor, a nucleoside analog or precursor analog, a peptide antibiotic, a platinum-based agent, or a plant alkaloid. In some aspects, the chemotherapeutic agent is a nucleoside analog.

In some aspects, the kits can further comprise instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

For biological methods, specific immunological binding of an antibody to a protein can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the protein marker is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously. In some aspects, the amount of signal can be quantified using an automated high-content imaging system. High-content imaging systems are commercially available (e.g., ImageXpress, Molecular Devices Inc., Sunnyvale, Calif.).

Antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Analysis of nucleic acid expression levels or genotype can be achieved using routine techniques such as Southern analysis, reverse-transcriptase polymerase chain reaction (RT-PCR), or any other methods based on hybridization to a nucleic acid sequence that is complementary to a portion of the coding sequence of interest (e.g., slot blot hybridization) are also within the scope of the present invention. Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of nucleic acid expression levels or genotype can also be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell Biol.*, 3:39-42 (1992)), sequencing with mass spectrometry such as matrix-assisted laser desorption/ionization time-of-flight mass spectrometry (MALDI-TOF/MS; Fu et al., *Nat. Biotechnol.*, 16:381-384 (1998)), pyrosequencing (Ronaghi et al., *Science*, 281:363-365 (1998)), and sequencing by hybridization. Chee et al., *Science*, 274:610-614 (1996); Drmanac et al., *Science*, 260:1649-1652 (1993); Drmanac et al., *Nat. Biotechnol.*, 16:54-58 (1998). Non-limiting examples of electrophoretic analysis include slab gel electrophoresis such as agarose or polyacrylamide gel electrophoresis, capillary electrophoresis, and denaturing gradient gel electrophoresis. In some aspects, methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SN-UPE), and pyrosequencing.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

The analysis can be carried out in a variety of physical formats. For example, the use of microtiter plates or automation could be used to facilitate the processing of large numbers of test samples.

Alternatively, for detecting the level of protein or nucleic acid expression, antibody or nucleic acid probes can be applied to subject samples immobilized on microscope slides. The resulting antibody staining or in situ hybridization pattern can be visualized using any one of a variety of light or fluorescent microscopic methods known in the art.

Analysis of the protein or nucleic acid can also be achieved, for example, by high pressure liquid chromatography (HPLC), alone or in combination with mass spectrometry (e.g., MALDI/MS, MALDI-TOF/MS, tandem MS, etc.).

Methods of Synthesis

In a fifth embodiment, the invention presents a method of selectively preparing a 4-substituted imidazole, the method including the steps:

cyclizing an α-alkylamino ketone and an acyl cyanamide to form a 2-N-acyl imidazolidin-2-imine product; and converting the 2-N-acyl imidazolidin-2-imine to a 2-acylaminoimidazole product; wherein the 2-acylamino product is substantially free from 1-acyl and 3-acyl regioisomers (e.g., <2% or <1% of such products). In some aspects, the cyclization step comprises an acid catalyst. In some aspects, the conversion to the 2-acylaminoimidazole comprises elimination of water with an acid catalyst (e.g., trifluoacetic acid in ethanol). In some preferred aspects, the 2-acylamino product is substantially free from $N^2,N^2$-diacyl products (e.g., <2% or <1% of such products).

In a sixth embodiment, the invention presents a method of selectively preparing a 2-acylamino 4-substituted imidazole, the method comprising the steps:

monoalkylating an α-amino acid, ester, or amide at the α-amino group;

converting the α-alkylamino acid, ester, or amide to an α-alkylamino ketone;

cyclizing the α-alkylamino ketone and an acyl cyanamide to form a 2-N-acyl imidazolidin-2-imine product; and converting the 2-N-acyl imidazolidin-2-imine to a 2-acylaminoimidazole product; wherein the 2-acylamino product is substantially free from 1-acyl and 3-acyl regioisomers (e.g., <2% or <1% of such products). In some aspects, the cycling step comprises an acid catalyst. In some preferred aspects, the 2-acylamino product is substantially free from $N^2,N^2$-diacyl products (e.g., <2% or <1% of such products).

In some aspects of the fifth or sixth embodiment, the α-amino group is protected. In some more specific aspects, the α-amino protecting group is a carbamate protecting group. In some more specific aspects, the 3-N-protecting group is a tert-butyloxycarbonyl (BOC) group. In some more specific aspects, the 3-N-protecting group is a Cbz group.

In some aspects of the fifth or sixth embodiments, the method further comprises the step of deprotecting the α-amino group (e.g., before cyclization). In some more specific aspects, the method comprises the step of removing a tert-butyloxycarbonyl (BOC) group with acid (e.g., trifluoroacetic acid).

In some aspects of the fifth or sixth embodiment, the 2-acylamino imidazole product is a compound of the first embodiment or any of its aspects.

The cyclization reaction in the methods of the invention can be conducted at any suitable temperature. In general, reactions are conducted at temperatures ranging between about 10° C. and about 200° C. A reaction can be conducted, for example, at from about 10° C. to about 100° C., or from about 10° C. to about 40° C., or from about 15° C. to about 150° C., or from about 15° C. to about 35° C., or from about 15° C. to about 25° C. A reaction can be conducted at temperature less than about 20, 25, 30, 35, 40, 45, 50, 55, 60, 65, 70, 75, 80, 85, 90, 95, 100, 105, 110, 115, 120, 125, 130, 135, 140, 145, 150, or 155° C. Other reaction temperatures can be used in the methods of the invention, depending in part on the particular compound used for the cyclization reaction.

Any suitable solvent or combination of solvents can be used in the methods of the invention. Suitable solvents include, but are not limited to, ethanol, methanol, diethyl ether, diisopropyl ether, ethyl acetate, benzene, toluene, chloroform, dichloromethane, carbon tetrachloride, 1,2-dichloroethane, 1,1-dichloroethane, N,N-dimethylformamide, N,N-dimethylacetamide, dimethylsulfoxide, N-methyl 2-pyrrolidone, methyl ethyl ketone, methyl isobutylketone, acetonitrile, propionitrile, 1,4-dioxane, sulfolane, 1,2-dimethyoxyethane, and combinations thereof. In some embodiments, the reaction mixture comprises ethanol.

In some embodiments, the reaction mixture comprises an acid catalyst. Suitable acid catalysts include trifluoroacetic acid, hydrochloric acid, hydrobromic acid, trichloroacetic acid, and the like.

Any suitable reaction time can be used in the methods of the invention. In general, reactions are allowed to run for a time sufficient for consumption of the starting material and conversion to the desired product, or until conversion of the starting material comes to a stop. Reactions are typically allowed to run for any amount of time ranging from a few minutes to several hours. Reactions can be run, for example, for anywhere between 5 minutes and 48 hours. Reactions can be run for about 20 minutes, or about 40 minutes, or about 60 minutes. Reactions can be run for about 1.5, 2, 2.5, 3, 3.5, 4, 4.5, 5, 5.5, 6, 6.5, 7, 7.5, 8, 8.5, 9, 9.5, 10, 11, 12, 14, 16, 18, 20, 22, 24, 30, 36, 42, or 48 hours. In some embodiments, reactions are run for less than 24 hours. In some embodiments, reactions are run for less than 12 hours. In some embodiments, reactions are run for less than 10 hours. Other reaction times can be used in the methods of the invention, depending on the particular catalysts or reactants that are used.

While simple in design, it is very difficult to selectively acylate 2-aminoimidazoles. Zhang et al. *Eur J Med Chem* 2014, 83, 74-83. Predominance of the imino-tautomer initiates $N^2$-acylation over the expected $N^3$-acylation, and with a product acidified by the acyl group, the second acylation event is facile leading to the diacylated products. In some aspects of the present invention, a regioselective cyclization was employed to achieve selectivity.

The compounds in the tables below were made using the methods set forth herein:

TABLE I

Selected 2-(Acylamino)imidazoles

| Compound | Chemical Structure |
| --- | --- |
| ZNA (for reference) | 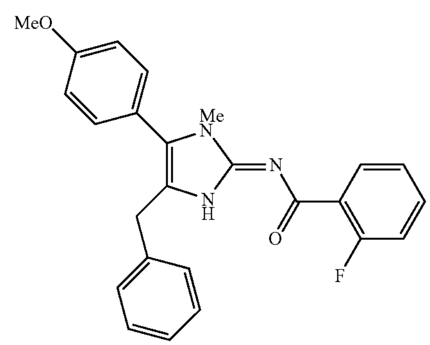 [SMILES: COc1ccc(-c2c(Cc3ccccc3)[nH]/c(=N\C(=O)c3ccccc3F)n2C)cc1] |
| 63 | 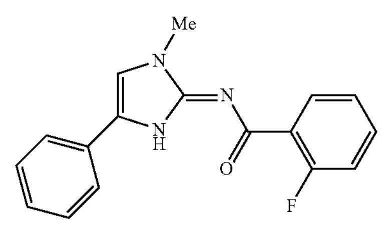 [SMILES: Cn1cc(-c2ccccc2)[nH]/c1=N\C(=O)c1ccccc1F] |
| 64 | 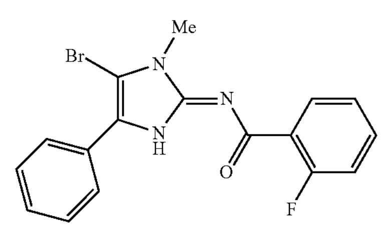 [SMILES: Cn1c(Br)c(-c2ccccc2)[nH]/c1=N\C(=O)c1ccccc1F] |
| 65 | 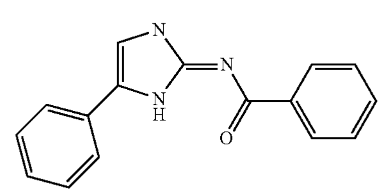 [SMILES: O=C(/N=c1/[nH]cc(-c2ccccc2)[nH]1)c1ccccc1] |

TABLE I-continued

Selected 2-(Acylamino)imidazoles

| Compound | Chemical Structure |
|---|---|
| 67 | 1-Me, 4-phenyl-imidazol-2-yl N-(4-chlorobenzoyl)imine · TFA |
| 78 | 1-Me, 4-phenyl-imidazol-2-yl N-(4-chlorobenzoyl)imine |
| 79 | 1-Me, 4-phenyl-imidazol-2-yl N-benzoylimine |
| 80 | 1-Me, 4-(4-methoxyphenyl)-imidazol-2-yl N-(2-fluorobenzoyl)imine |
| 81 | 1-Me, 4-(4-methoxyphenyl)-imidazol-2-yl N-(4-methoxybenzoyl)imine |
| 82 | 1-Me, 4-(4-methoxyphenyl)-imidazol-2-yl N-(4-chlorobenzoyl)imine |
| 83 | 1-Me, 4-(4-methoxyphenyl)-imidazol-2-yl N-benzoylimine |
| 84 | 1-Me, 4-phenyl-5-isopropyl-imidazol-2-yl N-(2-fluorobenzoyl)imine |
| 85 | 1-Me, 4-phenyl-5-isopropyl-imidazol-2-yl N-(4-methoxybenzoyl)imine |
| 86 | 1-Me, 4-phenyl-5-isopropyl-imidazol-2-yl N-(4-chlorobenzoyl)imine |
| 87 | 1-Me, 4-phenyl-5-isopropyl-imidazol-2-yl N-benzoylimine |
| 96 | 1-Me, 4-(4-methoxyphenyl)-imidazol-2-yl N-(4-fluorobenzoyl)imine |

TABLE I-continued

Selected 2-(Acylamino)imidazoles

| Compound | Chemical Structure |
|---|---|
| 97 | 1-methyl-4-phenyl-imidazole with N=C(NH)-C(=O)-(4-fluorophenyl) |
| 98 | 1-methyl-4-(4-methoxyphenyl)-imidazole with N=C(NH)-C(=O)-(2,4-dichlorophenyl) |
| 99 | 1-methyl-4-(benzo[1,3]dioxol-5-yl)-imidazole with N=C(NH)-C(=O)-(4-chlorophenyl) |
| 100 | 1-methyl-4-(benzo[1,3]dioxol-5-yl)-imidazole with N=C(NH)-C(=O)-(2-fluorophenyl) |
| 103 | 1-methyl-4-(pyridin-2-yl)-imidazole with N=C(NH)-C(=O)-(4-chlorophenyl) |
| 104 | 1-methyl-4-(2-methylphenyl)-imidazole with N=C(NH)-C(=O)-(4-chlorophenyl) |
| 105 | 1-methyl-4-(2-methylphenyl)-imidazole with N=C(NH)-C(=O)-(2-fluorophenyl) |
| 109 | 1-ethyl-4-(4-methoxyphenyl)-imidazole with N=C(NH)-C(=O)-(2-fluorophenyl) |
| 110 | 1-ethyl-4-(4-methoxyphenyl)-imidazole with N=C(NH)-C(=O)-(4-chlorophenyl) |
| 111 | 1-ethyl-4-phenyl-imidazole with N=C(NH)-C(=O)-(4-chlorophenyl) |
| 114 | 1,5-dimethyl-4-phenyl-imidazole with N=C(NH)-C(=O)-(2-fluorophenyl) |
| 119 | 1-benzyl-4-methyl-imidazole with N=C(NH)-C(=O)-phenyl |

TABLE I-continued
Selected 2-(Acylamino)imidazoles
| Compound | Chemical Structure |
|---|---|
| 120 | 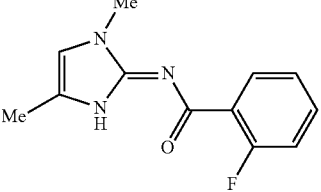 |
| 124 | 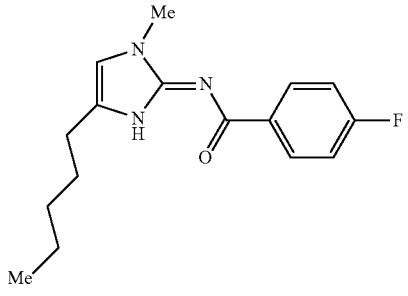 [SMILES: CCCCCc1cn(C)/c(=N/C(=O)c2ccc(F)cc2)[nH]1] |
| 128 | 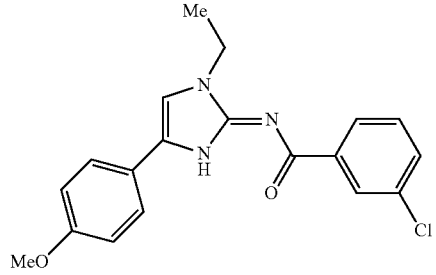 [SMILES: CCn1cc(-c2ccc(OC)cc2)[nH]/c1=N\C(=O)c1cccc(Cl)c1] |
| 129 | 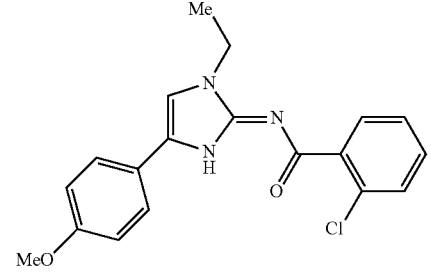 [SMILES: CCn1cc(-c2ccc(OC)cc2)[nH]/c1=N\C(=O)c1ccccc1Cl] |
| 132 | 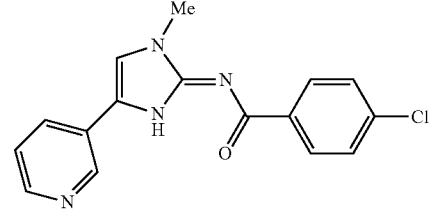 [SMILES: Cn1cc(-c2cccnc2)[nH]/c1=N\C(=O)c1ccc(Cl)cc1] |
| 133 | 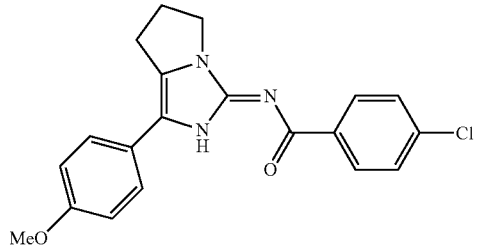 [SMILES: COc1ccc(-c2[nH]/c(=N\C(=O)c3ccc(Cl)cc3)n3c2CCC3)cc1] |
| 136 | 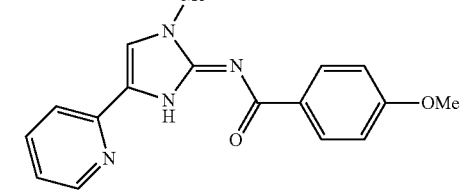 |
| 137 | 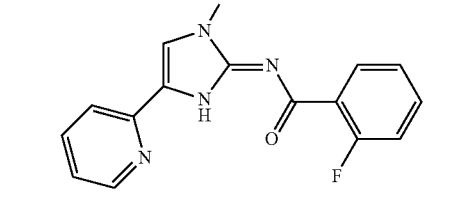 |
| 138 | 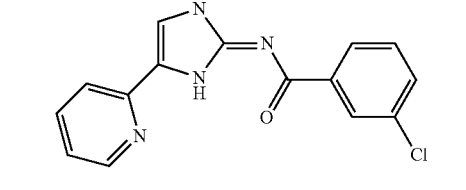 |
| 139 | 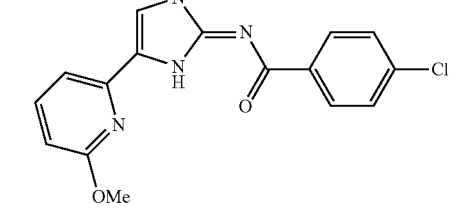 |
| 140 | 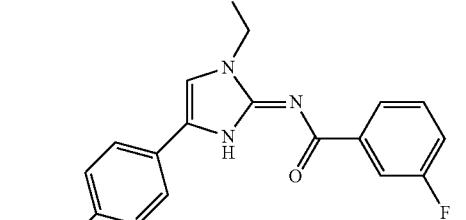 |

TABLE I-continued

Selected 2-(Acylamino)imidazoles

| Compound | Chemical Structure |
|---|---|
| 141 | 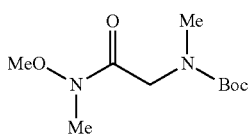 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1: Preparation of Weinreb Amides

General Procedure A: Preparation of Weinreb Amides tert-Butyl (2-(methoxy(methyl)amino)-2-oxoethyl)(methyl)carbamate (1a)

In a 250 mL round bottom flask containing a magnetic stir bar were added Boc-sarcosine (4.35 g, 22.99 mmol) and $CH_2Cl_2$ (80 mL) at room temperature. Carbonyl diimidazole (4.10 g, 25.29 mmol) was then added in portions over 15 minutes. After 1.5 h, N,O-dimethylhydroxylamine hydrochloride (2.47 g, 25.29 mmol) was added in one portion and the reaction mixture was allowed to stir for an additional 16 h. The mixture was then diluted with EtOAc (200 mL), and washed consecutively with 1M HCl (100 mL), saturated $NaHCO_3$(100 mL), and brine (100 mL). The organic extract was dried over $Na_2SO_4$, filtered, and then evaporated under reduced pressure to yield a colorless oil (4.59 g, 86%). $R_f$=0.33 (6:4 hexanes/EtOAc). $^1$H NMR (CDCl$_3$, 500 MHz): δ 4.15 (s, 1.2H, rotamer 1), 4.07 (s, 0.8H, rotamer 2), 3.71-3.69 (2s, 3H, rotamer 1 and 2), 3.19-3.18 (2s, 3H, rotamer 1 and 2), 2.93-2.92 (2s, 3H, rotamer 1 and 2), 1.47 (s, 5.4H, rotamer 1), 1.43 (s, 3.6H, rotamer 2). $^{13}$C NMR (125 MHz, CDCl$_3$, mixture of rotamers) δ 170.0, 156.3, 155.7, 79.7, 79.6, 61.2, 61.2, 50.1, 49.6, 35.8, 35.6, 32.1, 28.3, 28.2, 28.1 ppm. IR (thin film) 2976, 2249, 1676, 1479, 1447, 1388, 1366, 1322, 1241, 1175, 1148, 1057, 999, 963, 911, 882, 772, 727 cm$^{-1}$. HRMS (ESI-TOF) m/z: [M+Na]+ Calcd for $C_{10}H_{20}N_2O_4Na$ 255.1318; Found 255.1336.

tert-Butyl (1-(methoxy(methyl)amino)-1-oxo-3-phenylpropan-2-yl)(methyl)carbamate (1b)

Prepared according to general procedure A from N-(tert-butoxycarbonyl)-N-methylphenylalanine (2.0 g, 7.16 mmol), carbonyldiimidazole (1.23 g, 7.88 mmol), and dimethylhydroxylamine hydrochloride (768 mg, 7.88 mmol) as a colorless oil (2.13 g, 92%). $R_f$=0.47 (6:4 hexanes/EtOAc). $^1$H NMR (500 MHz, CDCl$_3$, mixture of rotamers) δ 7.31-7.07 (m, 5H, rotamers 1 & 2), 5.52 (s, 0.44H, rotamer 1), 5.15 (s, 0.66H, rotamer 2), 3.61-3.58 (m, 3H, rotamers 1 & 2), 3.16-3.13 (m, 3H, rotamers 1&2), 3.04-2.87 (m, 2H, rotamers 1 & 2), 2.83-2.82 (m, 3H, rotamers 1 & 2), 1.32 (s, 4.3H, rotamer 1), 1.21 (s, 4.7H, rotamer 2) ppm. $^{13}$C NMR (125 MHz, CDCl$_3$, mixture of rotamers) δ 171.9, 171.4, 155.6, 154.9, 1380, 137.4, 129.3, 129.2, 128.4, 128.2, 126.4, 126.3, 79.8, 79.6, 61.3, 57.1, 54.7, 34.9, 32.3, 30.2, 29.7, 28.2, 28.0 ppm. IR (thin film) 2975, 2935, 2245, 1667, 1477, 1454, 1392, 1366, 1322, 1254, 1168, 1141, 1076, 991, 958, 909, 865, 721 cm$^{-1}$. HRMS (ESI-TOF) m/z: [M+Na]+ Calcd for $C_{17}H_{26}N_2O_4Na$ 345.1790; Found 345.1790.

tert-Butyl (1-(methoxy(methyl)amino)-3-methyl-1-oxobutan-2-yl)(methyl)carbamate (1c)

Prepared according to general procedure A from N-(tert-butoxycarbonyl)-N-methylvaline (7.89 g, 34.1 mmol), carbonyldiimidazole (6.08 g, 37.51 mmol), and dimethylhydroxylamine hydrochloride (3.66 g, 37.51 mmol) as a colorless oil (7.95 g, 85%).

tert-Butyl ethyl(2-(methoxy(methyl)amino)-2-oxoethyl)carbamate (1d)

Prepared according to general procedure A from N-(tert-butoxycarbonyl)-N-ethylglycine (0.60 g, 3.00 mmol), carbonyldiimidazole (0.53 g, 3.30 mmol), and dimethylhydroxylamine hydrochloride (0.32 g, 3.30 mmol) as a pale yellow oil (0.69 g, 90%); $^1$H NMR (500 MHz, CDCl$_3$, mixture of rotamers): δ 4.14 (s, 2H, rotamer 1), 4.05 (s, 1H, rotamer 2), 3.74-3.69 (m, 3H, rotamers 1 & 2), 3.35-3.26 (m, 2H, rotamers 1 & 2), 3.18 (s, 3H, rotamers 1 & 2), 1.48 (s, 6H, rotamer 1), 1.43 (s, 3H, rotamer 2), 1.12-1.10 (m, 3H, rotamers 1 &2) ppm. $^{13}$C NMR (125 MHz, CDCl$_3$) δ 166.4, 152.1, 151.3, 75.7, 57.4, 43.8, 43.5, 39.4, 38.9, 28.6, 24.5, 24.4, 9.6, 9.3 ppm. IR (thin film) 2973, 1681, 1400, 1250, 1146, 998, 982, 771 cm$^{-1}$. HRMS (ESI-TOF) m/z: [M+Na]+ Calcd for C$_{11}$H$_{22}$N$_2$O$_4$Na 269.1477; Found 269.1499.

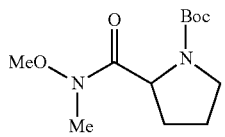

1e tert-Butyl 2-(methoxy(methyl)carbamoyl)pyrrolidine-1-carboxylate (1e)

Prepared according to general procedure A from Boc-proline (5.0 g, 23.2 mmol), carbonyldiimidazole (4.14 g, 25.5 mmol), and dimethylhydroxylamine hydrochloride (2.48 g, 25.5 mmol) as a colorless oil (5.16 g, 86%). R$_f$=0.24 (6:4 hexanes/EtOAc). $^1$H NMR (500 MHz, CDCl$_3$, mixture of rotamers) δ 4.75-4.64 (m, 0.45H, rotamer 1), 4.61-4.58 (m, 0.55H, rotamer 2), 3.78 (s, 1.4H, rotamer 1), 3.71 (s, 1.6H, rotamer 2), 3.65-3.51 (m, 1H, rotamers 1 & 2), 3.48-3.39 (m, 1H, rotamers 1 &2), 3.19 (s, 3H), 2.32-2.07 (m, 1H, rotamers 1 & 2), 2.04-1.77 (m, 2H, rotamers 1 & 2), 1.45 (s, 4.4H, rotamer 1), 1.41 (s, 4.6H, rotamer 2) ppm. $^{13}$C NMR (125 MHz, CD$_3$OD, mixture of rotamers) δ 191.9, 165.2, 131.3, 125.3, 114.1, 62.8, 54.9 (2), 46.0, 29.8, 23.8 ppm. IR (thin film) 2974, 1694, 1389, 1160, 1119, 998, 773 cm$^{-1}$. HRMS (ESI-TOF) m/z: [M+Na]+ Calcd for C$_{12}$H$_{22}$N$_2$O$_4$Na 281.1477; Found 281.1502.

Example 2: General Procedure B1 (Synthesis of α-Aminoketones)

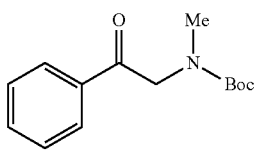

2a tert-Butyl methyl(2-oxo-2-phenylethyl)carbamate (2a)

To a cooled solution of (1a) (500 mg, 2.15 mmol) in THF (15 mL) at −10° C. in an oven-dried 50 mL round-bottom flask was added a solution of 3M PhMgBr in ether (1.00 mL, 3.01 mmol). After 1 h the reaction mixture was quenched by dropwise addition of saturated NH$_4$Cl (5 mL). EtOAc (20 mL) was then added to the solution, and the organic layer was partitioned, dried over Na$_2$SO$_4$, filtered, and concentrated under reduced pressure. The crude material was purified by column chromatography, eluting with 8:2 hexanes/EtOAc to yield a colorless oil (700 mg, 65%). R$_f$=0.52 (6:4 hexanes/EtOAc).). $^1$H NMR (CDCl$_3$, 500 MHz): δ 7.95-7.91 (m, 2H, rotamer 1 & 2), 7.61-7.55 (m, 1H, rotamer 1 & 2), 7.50-7.44 (m, 2H, rotamer 1 & 2), 4.67 (s, 1. H, rotamer 1), 4.58 (s, 0.9H, rotamer 2), 2.97 (s, 1.4H, rotamer 2), 2.94 (s, 1.6H, rotamer 1), 1.48 (s, 4.8H, rotamer 1), 1.37 (s, 4.2H, rotamer 2). $^{13}$C NMR (125 MHz, CHCl$_3$, mixture of rotamers) δ 191.2, 190.9, 131.3, 129.6, 129.5, 129.5, 126.2, 124.9, 124.8, 124.7, 124.5, 124.0, 124.0 (2), 123.8, 120.6, 76.2, 51.7, 51.1, 31.7, 25.8, 24.4, 24.3 ppm. IIR (thin film) 2975, 2930, 1686, 1597, 1479, 1449, 1390, 1365, 1302, 1224, 1145, 987, 882, 752 cm$^{-1}$. HRMS (ESI-TOF) m/z: [M+Na]+ Calcd for C$_{15}$H$_{21}$NO$_4$Na 302.1368; Found 302.1374.

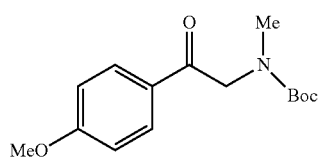

2b tert-Butyl (2-(4-methoxyphenyl)-2-oxoethyl)(methyl)carbamate (2b)

Prepared according to general procedure B1 from 4-methoxylphenylmagnesium bromide (1M in THF, 17.25 mL, 17.25 mmol) and 1a (3.34 g, 14.4 mmol) as a colorless oil (2.63 g, 55%). R$_f$=0.47 (6:4 hexanes/EtOAc). $^1$H NMR (CDCl$_3$, 500 MHz, mixture of rotamers): δ 7.96-7.87 (m, 2H, rotamers 1&2), 6.96-6.92 (m, 2H, rotamers 1&2), 4.63 (s, 1.1H, rotamer 1), 4.53 (s, 0.9H, rotamer 2), 3.88-3.86 (m, 3H, rotamers 1&2), 2.96-2.93 (m, 2H, rotamers 1&2), 1.48 (s, 5H, rotamer 1), 1.37 (s, 4H, rotamer 2). $^{13}$C NMR (125 MHz, CDCl$_3$) δ 193.6, 193.2, 163.7, 156.3, 130.2, 130.0, 128.3, 113.9, 113.8, 80.0, 79.9, 55.5, 55.3, 54.7, 53.4, 35.6, 28.4, 28.2 ppm. IR (thin film) 2974, 2932, 1681, 1600, 1576, 1512, 1480, 1455, 1390, 1365, 1308, 1231, 1170, 1141, 1029, 986, 883, 834 cm$^{-1}$. HRMS (ESI-TOF) m/z: [M+Na]+ Calcd for C$_{15}$H$_{21}$NO$_4$Na 302.1368; Found 302.1374.

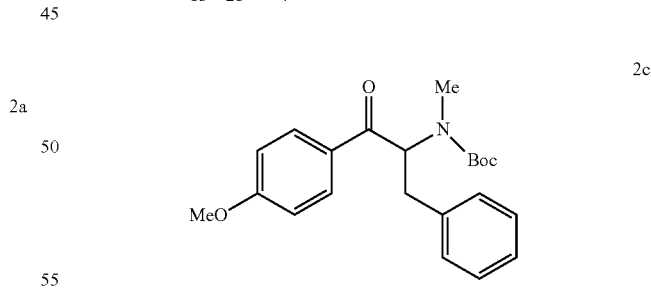

2c tert-Butyl (1-(4-methoxyphenyl)-1-oxo-3-phenylpropan-2-yl)(methyl)carbamate (2c)

Prepared according to general procedure B1 from 4-methoxylphenylmagnesium bromide (1M in THF, 14.5 mL, 14.5 mmol) and 1b (3.90 g, 12.1 mmol) as a colorless oil (3.37 g, 75%). R$_f$=0.63 (6:4 hexanes/EtOAc). $^1$H NMR (500 MHz, CDCl$_3$, mixture of rotamers) δ 8.03 (d, J=9.0 Hz, 1H, rotamer 1), 7.93 (d, J=9.0 Hz, 1H, rotamer 2), 7.36-7.08 (m, 5H, rotamers 1 &2), 6.90-6.88 (m, 2H, rotamers 1 & 2), 5.88 (dd, J=8.8, 6.3 Hz, 0.5H, rotamer 1), 5.43 (dd, J=9.9, 4.7 Hz, 0.5H, rotamer 2), 3.84 (d, J=5.1 Hz, 3H, rotamers 1 &2), 3.26-2.93 (m, 2H, rotamers 1 & 2), 2.64 (dd, J=17.2, 1.6 Hz, 3H, rotamers 1 &2), 1.30 (dd, J=23.8, 1.7 Hz, 9H, rotamers 1 &2) ppm. $^{13}$C NMR (125 MHz, CDCl$_3$) δ 196.7, 196.3, 163.7, 163.7, 155.3, 154.4, 138.3, 137.7, 131.0, 130.6, 129.5, 129.4, 129.3, 128.5, 128.5, 128.4, 128.2, 126.4, 126.4, 126.3, 126.3, 113.8, 113.8, 113.7, 80.4, 80.1, 61.9, 59.0, 55.5, 55.4, 55.2, 34.0, 33.9, 29.9, 29.7, 28.4, 28.2, 28.2, 28.1 ppm. IR (thin film): 1676, 1599, 1512, 1454, 1287, 1366, 1309, 1252, 1165, 1137, 1027 cm$^{-1}$. HRMS (ESI-TOF) m/z: [M+Na]+ Calcd for C$_{22}$H$_{27}$NO$_4$Na 392.1838; Found 392.1837.

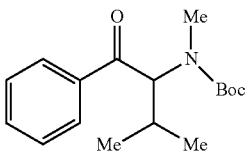

tert-Butyl methyl(3-methyl-1-oxo-1-phenylbutan-2-yl)carbamate (2d)

Prepared according to general procedure B1 from phenylmagnesium bromide (3M in Et$_2$O, 4.0 mL, 12.0 mmol) and 1c (2.76 g, 10.0 mmol) as a colorless oil (1.25 g, 43%). R$_f$=0.75 (6:4 hexanes/EtOAc). $^1$H NMR (500 MHz, CDCl$_3$, mixture of rotamers) δ 8.18-8.11 (m, 1.2H, rotamer 1), 8.08-8.00 (m, 0.8H, rotamer 2), 7.63-7.54 (m, 1H, rotamers 1 & 2), 7.49-7.45 (m, 2H, rotamers 1 & 2), 5.32 (d, J=10.6 Hz, 0.6H, rotamer 1), 5.06 (d, J=10.4 Hz, 0.4H, rotamer 2), 2.67 (s, 1.2H, rotamer 2), 2.62 (s, 1.8H, rotamer 1), 2.49-2.39 (m, 1H, rotamers 1 & 2), 1.55 (s, 3H, rotamer 2), 1.45 (s, 5H, rotamer 1), 0.98-0.89 (m, 6H, rotamers 1 & 2). $^{13}$C NMR (126 MHz, CDCl$_3$, mixture of rotamers) δ 198.1, 197.3, 155.9, 155.0, 136.5, 136.2, 133.4, 133.3, 128.7, 128.6, 128.5, 128.5, 127.2, 127.2, 80.6, 80.1, 64.0, 62.5, 29.2, 28.5, 28.3, 26.0, 25.8, 20.1, 19.9, 18.6, 18.2. IR (thin film) 2970, 2685, 1738, 1677, 1358, 1233, 979, 762 cm$^{-1}$. HRMS (ESI-TOF) m/z: [M+Na]+ Calcd for C$_{17}$H$_{25}$NO$_3$Na 314.1732; Found 314.1735.

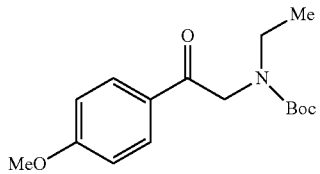

tert-Butyl ethyl(2-(4-methoxyphenyl)-2-oxoethyl)carbamate (2e)

Prepared according to general procedure B1 with 1d (0.17 g, 0.69 mmol), 4-methoxylphenylmagnesium bromide (1M in THF, 1.38 mL, 1.38 mmol) and anhydrous diethyl ether as solvent. The product was isolated as a yellow oil (0.19 g, quant.). R$_f$=0.5 (3:1 hexanes/EtOAc). $^1$H NMR (300 MHz, CDCl$_3$, mixture of rotamers) δ 7.93 (d, J=8.7 Hz, 2H, rotamer 1), 7.28-7.26 (m, 0.4H, rotamer 2), 6.93 (t, J=9.3 Hz, 2H, rotamer 1), 6.87-6.84 (m, 0.4H, rotamer 2), 6.79-6.71 (m, 0.8H, rotamer 2), 4.61 (s, 1H, rotamer 1), 4.51 (s, 1H, rotamer 2), 3.86 (s, 3H, rotamer 1), 3.79-3.73 (m, 1H, rotamer 2), 3.42-3.27 (m, 2H, rotamer 1 & 2), 1.49 (s, 5H, rotamer 1), 1.36 (s, 4H, rotamer 2). 1.12-1.09 (m, 3H). $^{13}$C NMR (125 MHz, CDCl$_3$) δ $^{13}$C NMR (CDCl$_3$, 75 MHz): δ 193.9, 163.9, 150.5, 130.5, 128.6, 116.2, 114.0, 80.1, 56.0, 53.1, 43.3, 28.7, 13.8. IR (thin film): 2976, 2934, 2917, 2849, 1701, 1683, 1602, 1576, 1512, 1480, 1455, 1423, 1402, 1366, 1318, 1265, 1233, 1172, 1146, 1113, 832, 779, 733 cm$^{-1}$.

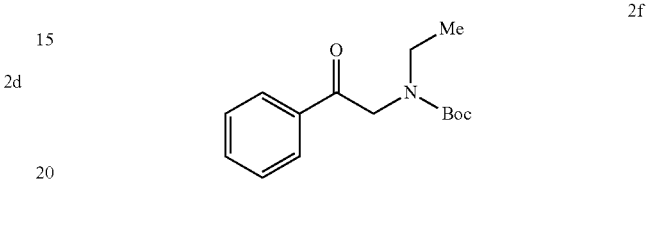

tert-Butyl ethyl(2-oxo-2-phenylethyl)carbamate (2f)

Prepared according to general procedure B1 with 1d (0.3 g, 1.21 mmol), phenylmagnesium bromide (3M in Et$_2$O, 0.81 mL, 2.43 mmol) and anhydrous diethyl ether as solvent. The product was isolated as a yellow oil (0.28 g, 88%). R$_f$=0.55 (3:1 hexanes/EtOAc). R$_f$=0.55 (3:1 hexanes/EtOAc); $^1$H NMR (300 MHz, CDCl$_3$, mixture of rotamers) δ 7.88-7.87 (m, 2H, rotamer 1 & 2), 7.52-7.48 (m, 1H, rotamer 1&2), 7.42-7.35 (m, 2H, rotamer 1 & 2), 4.60 (s, 1H, rotamer 1), 4.50 (s, 1H, rotamer 2), 3.34 (q, J=7.0 Hz, 1H, rotamer 1), 3.25 (q, J=7.0 Hz, 1H, rotamer 2), 1.43-1.30 (m, 9H, rotamer 1 & 2), 1.06 (t, J=7.0 Hz, 3H). $^{13}$C NMR (CDCl$_3$, 125 MHz): δ 195.2, 156.9, 135.3, 133.4, 128.7, 125.3, 119.4, 115.4, 79.8, 53.3, 43.2, 28.3, 13.5.

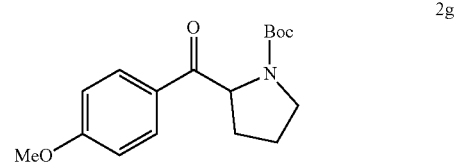 [SMILES: COc1ccc(C(=O)C2CCCN2C(=O)OC(C)(C)C)cc1]

tert-Butyl 2-(4-methoxybenzoyl)pyrrolidine-1-carboxylate (2g)

Prepared according to general procedure B1 from 1e (2.5 g, 9.68 mmol) and 4-methoxyphenylmagnesium bromide (2.0 M in THF, 6.8 mL, 13.54 mmol) as an off-yellow solid (850 mg, 29%). R$_f$=0.44 (6:4 hexanes/EtOAc). $^1$H NMR (500 MHz, CDCl$_3$, mixture of rotamers) δ 7.97-7.92 (m, 2H, rotamer 1 & 2), 6.95-6.90 (m, 2H, rotamer 1 & 2), 5.29 (dd, J=9.4, 3.0 Hz, 0.4H, rotamer 1), 5.14 (dd, J=8.8, 3.8 Hz, 0.6H, rotamer 2), 3.86 (s, 1.75H, rotamer 2), 3.84 (s, 1.25H, rotamer 1), 3.69-3.41 (m, 2H, rotamers 1 & 2), 2.36-2.20 (m, 1H, rotamers 1 & 2), 1.97-1.84 (m, 3H, rotamers 1 & 2), 1.45 (s, 4H, rotamer 1), 1.24 (s, 5H, rotamer 2). $^{13}$C NMR (125 MHz, CDCl$_3$, mixture of rotamers) δ 197.4, 196.8, 163.5, 154.4, 153.9, 130.8, 130.4, 128.2, 128.0, 113.8, 113.7, 79.6, 79.5, 61.0, 60.7, 55.5, 55.4, 46.8, 46.6, 31.0, 30.0, 28.5, 28.2, 24.2, 23.6. IR (thin film) 1682, 1599, 1575, 1511, 1393, 1365, 1308, 1255, 1230, 1160, 1117, 1027, 990, 839 cm$^{-1}$. HRMS (ESI-TOF) m/z: [M+Na]+ Calcd for $C_{17}H_{23}NO_4Na$ 328.1525; Found 328.1542.

Example 3: General Procedure B2 (Synthesis of α-Aminoketones)

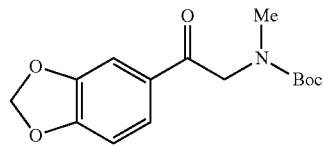

tert-Butyl (2-(benzo[d][1,3]dioxol-5-yl)-2-oxoethyl)(methyl)carbamate (2h)

To a flame dried 100 mL round-bottom flask under a $N_2$ atmosphere equipped with a magnetic stir bar was added 4-bromo-1-2-methlyenedioxybenzene (1.81 mL, 15 mmol) and freshly distilled tert-butyl methyl ether (25 mL). The solution was cooled to 0° C., followed by the dropwise addition of 2.5M n-BuLi in hexanes (12 mL, 30 mmol) over the period of 15 minutes. The reaction was allowed to proceed for 1 hour at 0° C., and then was cooled to −78° C. A solution of 1a (3.16 g, 13.6 mmol) dissolved in tert-butyl methyl ether (25 mL) was then added dropwise. The reaction was allowed to warm to room temperature overnight, and then was quenched with saturated $NH_4Cl$ (25 mL). The suspension was extracted with diethyl ether (2×25 mL), and the organics were combined, dried over $Na_2SO_4$, and evaporated under reduced pressure. The crude residue was purified via column chromatography, eluting with a gradient of 9:1 hexanes/EtOAc to 4:1 hexanes/EtOAc to yield a colorless liquid (1.3 g, 33%). $R_f$=0.62 (6:4 hexanes/EtOAc). $^1$H NMR (500 MHz, CDCl$_3$, mixture of rotamers) δ 7.60-7.48 (m, 1H, rotamer 1 & 2), 7.42 (s, 0.8H, rotamer 1), 7.27 (s, 0.2H, rotamer 2), 6.93-6.65 (m, 1H, rotamer 1 & 2), 6.06-6.05 (m, 1H, rotamer 1 & 2), 4.60 (s, 1H rotamer 1), 4.51 (s, 1H, rotamer 2), 2.96-2.93 (m, 2H, rotamer 1 & 2), 1.50 (s, 5H, rotamer 1), 1.39 (s, 4H, rotamer 2) ppm. $^{13}$C NMR (125 MHz, CDCl$_3$, mixture of rotamers) δ 193.2, 192.8, 156.3, 155.8, 152.1, 152.0, 148.3, 148.2, 144.0, 130.0, 124.1, 123.8, 120.7, 115.2, 108.1, 108.0, 107.8, 107.6, 101.9, 101.8, 80.1, 80.0, 55.4, 54.8, 35.7, 35.6, 28.4, 28.2 ppm. HRMS (ESI-TOF) m/z: [M+Na]+ Calcd for $C_{15}H_{19}NO_5Na$ 316.1161; Found 316.1184.

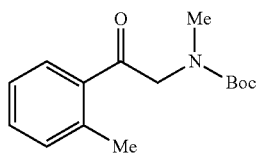

tert-Butyl methyl(2-oxo-2-(o-tolyl)ethyl)carbamate (2i)

Prepared according to general procedure B2 from iodotoluene (1.91 mL, 15.0 mmol), nBuLi (2.5M in hexanes, 12 mL, 30.0 mmol), and 1a (3.17 g, 13.6 mmol) as a yellow oil (750 mg, 21%). $R_f$=0.54 (6:4 hexanes/EtOAc). $^1$H NMR (500 MHz, CDCl$_3$, mixture of rotamers) δ 7.67 (d, J=7.8 Hz, 0.55H, rotamer 1), 7.57 (d, J=7.6 Hz, 0.45H, rotamer 2), 7.43-7.38 (m, 1H, rotamer 1 & 2), 7.34-7.19 (m, 2H, rotamer 1 & 2), 4.54 (s, 1H, rotamer 1), 4.45 (s, 1H, rotamer 2), 2.98 (s, 1.4H, rotamer 1), 2.95 (s, 1.6H, rotamer 2), 2.52-2.51 (m, 3H, rotamer 1 & 2), 1.49 (s, 4.2H rotamer 1), 1.42 (s, 5.8H rotamer 2) ppm. $^{13}$C NMR (125 MHz, CDCl$_3$, mixture of rotamers) δ 199.3, 198.8, 156.2, 155.7, 138.6, 138.2, 135.9, 135.7, 132.1, 132.0, 131.7, 128.2, 127.7, 125.7, 125.6, 78.0, 57.7, 57.1, 35.8, 35.7, 28.4, 28.3, 21.1, 20.9, 13.8 ppm.

Example 4: General Procedure B3 (Synthesis of α-Aminoketones)

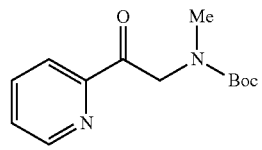

tert-Butyl methyl(2-oxo-2-(pyridin-2-yl)ethyl)carbamate (2j)

A solution of 2-bromopyridine (3.81 mL, 40.0 mmol) in 15 mL THF was added dropwise to a stirring solution of iPrMgCl (2.0 M in THF, 20.0 mL, 40.0 mmol) in an oven-dried round bottom flask equipped with a magnetic stir bar under $N_2$ atmosphere at room temperature. The resulting solution was allowed to stir overnight. The solution was then cooled to −40° C., followed by the dropwise addition of 1a (7.3 g, 31.4 mmol) dissolved in 15 mL THF. The reaction was then allowed to warm to 0° C., then quenched upon the addition of saturated $NH_4Cl$ (25 mL). The suspension was extracted with EtOAc (3×75 mL), and the organics were collected, dried over $Na_2SO_4$, filtered, and evaporated under reduced pressure. The resulting crude material was purified via column chromatography, eluting with a gradient of 4:1 hexanes/EtOAc to 100% EtOAc to yield and off-yellow solid (4.93 g, 63%). $R_f$=0.58 (6:4 hexanes/EtOAc). $^1$H NMR (500 MHz, CDCl$_3$, mixture of rotamers) δ 8.62 (dd, J=11.3, 4.8 Hz, 1H, rotamers 1 & 2), 7.99 (dd, J=13.5, 7.8 Hz, 1H, rotamers 1 &2), 7.88-7.70 (m, 1H, rotamers 1 &2), 7.50-7.36 (m, 1H, rotamers 1 &2), 4.89 (s, 0.9H, rotamer 1), 4.83 (s, 1.1H, rotamer 2), 2.93 (d, J=2.2 Hz, 3H, rotamers 1 & 2), 1.46 (s, 4.5H, rotamer 1), 1.33 (s, 5.5H, rotamer 2). $^{13}$C NMR (125 MHz, CDCl$_3$, mixture of rotamers) δ 196.3, 196.1, 156.3, 155.9, 152.4, 152.3, 140.0, 148.9, 137.0, 136.8, 127.6, 127.4, 121.8, 121.7, 79.7, 79.6, 55.6, 55.3, 35.8, 35.6, 28.4, 28.2 ppm. IR (thin film) 2977, 1714, 1688, 1588, 1224, 1170, 1142, 996 cm$^{-1}$.

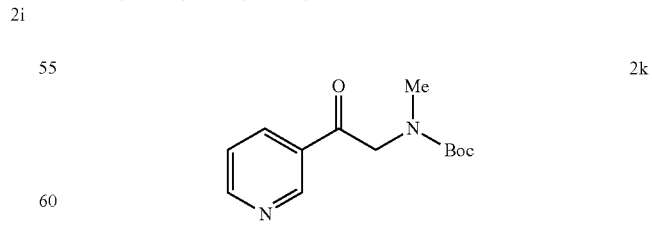

tert-Butyl methyl(2-oxo-2-(pyridin-3-yl)ethyl)carbamate (2k)

Prepared according to general procedure B3 from 3-bromopyridine (3.26 mL, 33.8 mmol), iPrMgCl (2.0 M in THF, 16.9 mL, 33.8 mmol), and 1a (3.93 g, 16.9 mmol) to yield an off-yellow oil (1.86 g, 44%). R$_f$=0.26 (EtOAc). $^1$H NMR (500 MHz, CDCl$_3$, mixture of rotamers) δ 9.19-9.09 (m, 1H, rotamers 1 & 2), 8.86-8.73 (m, 1H, rotamers 1 & 2), 8.23 (tt, J=7.9, 2.0 Hz, 1H, rotamers 1 & 2), 7.44 (ddd, J=17.3, 8.0, 4.9 Hz, 1H, rotamers 1 & 2), 4.63 (d, J=41.4 Hz, 2H, rotamers 1 & 2), 2.97 (d, J=14.5 Hz, 3H, rotamers 1 & 2), 1.43 (d, J=55.2 Hz, 9H, rotamers 1 & 2). $^{13}$C NMR (126 MHz, CDCl$_3$, mixture of rotamers) δ 194.4, 194.0, 153.9, 149.3, 149.1, 135.3, 135.2, 123.9, 123.7, 85.8, 85.0, 55.8, 55.3, 28.3, 28.3, 28.2. IR (thin film) 1684, 1390, 1234, 1146, 987, 879 cm$^{-1}$.

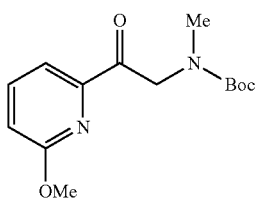

tert-Butyl (2-(6-methoxypyridin-2-yl)-2-oxoethyl) (methyl)carbamate (2l)

Prepared according to general procedure B3 from 2-bromo-6-methoxypyridine (2.35 g, 12.5 mmol), iPrMgCl (2.0 M in THF, 6.3 mL, 12.5 mmol), and 1a (3.0 g, 12.9 mmol) to yield an off-yellow oil (625 mg, 18%). R$_f$=0.38 (6:4 hexanes/EtOAc). $^1$H NMR (500 MHz, CDCl$_3$, mixture of rotamers) δ 7.74-7.64 (m, 2H, rotamers 1 &2), 6.99-6.95 (m, 1H, rotamers 1 & 2), 4.93 (s, 1.1H, rotamer 1), 4.82 (s, 0.9H, rotamer 2), 4.03-3.93 (m, 3H, rotamers 1 & 2), 2.98 (d, J=1.3 Hz, 3H, rotamers 1 & 2), 1.51 (s, 4.6H, rotamer 1), 1.39 (m, 4.4H, rotamer 2) ppm. $^{13}$C NMR (125 MHz, CDCl$_3$, mixture of rotamers) δ 192.0, 191.8, 159.4, 159.3, 152.4, 152.0, 145.8, 145.7, 135.3, 135.1, 111.9, 111.1, 111.1, 75.8, 75.7, 51.7, 51.4, 49.6, 49.5, 31.8, 31.7, 24.4, 24.3 ppm. IR (thin film) 1714, 1690, 1590, 1468, 1389, 1364, 1324, 1272, 1225, 1171, 1142, 1032 cm$^{-1}$. HRMS (ESI-TOF) m/z: [M+Na]+ Calcd for C$_{14}$H$_{20}$N$_2$O$_4$Na 303.1321; Found 303.1341.

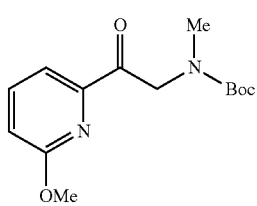

tert-Butyl (2-(3-methoxypyridin-2-yl)-2-oxoethyl) (methyl)carbamate (2m)

Prepared according to general procedure B3 from 3-bromo-3-methoxypyridine (2 g, 10.62 mmol), iPrMgCl (2.0 M in THF, 5.84 mL, 11.69 mmol), and 1a (2.54 g, 10.93 mmol) to yield an off-yellow oil (480 mg, 16%). R$_f$=0.43 (EtOAc). $^1$H NMR (500 MHz, CDCl$_3$, mixture of rotamers) δ 8.32-8.16 (m, 1.1H), 7.44-7.28 (m, 1.3H), 7.22-7.13 (m, 0.6H), 4.71 (d, J=58.9 Hz, 1.3H), 4.09 (d, J=37.8 Hz, 0.7H), 3.93-3.79 (m, 2.4H), 3.71-3.64 (m, 0.6H), 3.16 (d, J=5.7 Hz, 0.4H), 2.97-2.86 (m, 2.6H), 1.62-1.30 (m, 9H). $^{13}$C NMR (125 MHz, CDCl$_3$, mixture of rotamers) δ 191.0, 190.9, 151.6, 151.2, 150.9, 150.8, 150.5, 137.3, 137.2, 135.6, 135.6, 132.8, 123.2, 123.0, 119.0, 115.6, 115.2, 115.2, 75.0, 74.9, 74.8, 56.5, 56.5, 52.7, 52.1, 51.0, 50.7, 45.4, 44.9, 31.1, 31.0, 30.9, 23.6, 23.5.

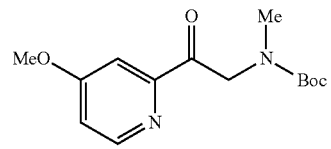

tert-Butyl (2-(4-methoxypyridin-2-yl)-2-oxoethyl) (methyl)carbamate (2n)

Prepared according to general procedure B3 from 2-bromo-4-methoxypyridine (2.5 g, 13.3 mmol), iPrMgCl (2.0 M in THF, 7.3 mL, 14.6 mmol), and 1a (3.18 g, 13.7 mmol) to yield an off-white solid (1.64 g, 44%) after purification via flash chromatography (gradient: 95:5 hexanes/EtOAc to 3:2 hexanes/EtOAc). R$_f$=0.38 (3:2 hexanes/EtOAc). $^1$H NMR (500 MHz, CDCl$_3$, mixture of rotamers) δ 8.48-8.40 (m, 1H, rotamers 1 & 2), 7.58-7.51 (m, 1H, rotamers 1 & 2), 7.02-6.93 (m, 1H, rotamers 1 & 2), 4.89 (s, 1H, rotamer 1), 4.83 (s, 1H, rotamer 2), 3.90 (s, 1.5H, rotamer 2), 3.88 (s, 1.5H, rotamer 1), 2.95 (s, 3H, rotamers 1 & 2), 1.48 (s, 4.5H, rotamer 2), 1.36 (s, 4.5H, rotamer 1). $^{13}$C NMR (125 MHz, CDCl$_3$, mixture of rotamers) δ 196.3, 196.0, 166.5, 166.4, 156.3, 155.9, 154.3, 154.2, 150.2, 150.1, 114.2, 106.9, 79.7, 79.6, 55.8, 55.5, 55.4, 35.8, 35.5, 28.4, 28.2.

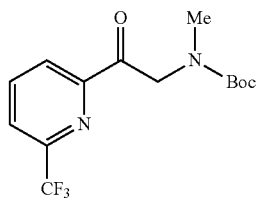

tert-Butyl methyl(2-oxo-2-(6-(trifluoromethyl)pyridin-2-yl)ethyl)carbamate (2o)

Prepared according to general procedure B2 from 2-bromo-6-trifluoromethylpyridine (2 g, 10.62 mmol), nBuLi (2.5M in hexanes, 5.7 mL, 14.2 mmol), and 1a (3.0 g, 12.9 mmol) to yield an off-yellow oil (1.60 g, 39%). R$_f$=0.66 (3:2 hexanes/EtOAc). IR (thin film): 1721, 1690, 1390, 1366, 1338, 1226, 1140, 1112, 997 cm$^{-1}$. $^1$H NMR (500 MHz, CDCl$_3$, mixture of rotamers) δ 8.23-8.18 (m, 1H, rotamer 1 & 2), 8.09-8.01 (m, 1H, rotamer 1 & 2), 7.90-7.84 (m, 1H, rotamer 1 & 2), 4.93 (s, 1.1H, rotamer 1), 4.85 (s, 0.9H, rotamer 2), 2.98 (s, 3H, rotamer 1 & 2), 1.47 (s, 5.4H, rotamer 1), 1.36 (s, 3.6H, rotamer 2) ppm. $^{13}$C NMR (125 MHz, CDCl$_3$, mixture of rotamers) δ 191.4, 191.3, 152.3, 151.8, 148.3 (2), 143.9, 143.8, 143.6, 143.5, 134.9, 134.7, 120.3, 120.2, 120.1, 120.0 (2), 118.2, 116.0, 113.8, 76.0, 75.9, 51.6, 51.5, 31.9, 31.7, 24.4, 24.2 ppm. IR (thin film): 1721, 1690, 1390, 1366, 1338, 1226, 1140, 1112, 997 cm$^{-1}$. HRMS (ESI-TOF) m/z: [M+H]+ Calcd for C$_{14}$H$_{17}$N$_2$O$_3$F$_3$Na 341.1089; Found 341.1104.

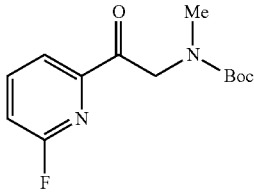

tert-Butyl (2-(6-fluoropyridin-2-yl)-2-oxoethyl)(methyl)carbamate (2p)

Prepared according to general procedure B3 from 3-bromo-6-fluoropyridine (2 g, 11.36 mmol), iPrMgCl (2.0 M in THF, 6.25 mL, 12.50 mmol), and 1a (2.64 g, 11.36 mmol) to yield an off-yellow oil (780 mg, 26%). R$_f$=0.46 (3:2 hexanes/EtOAc). $^1$H NMR (500 MHz, CDCl$_3$, mixture of rotamers) δ 8.05-7.87 (m, 2H, rotamer 1 &2), 7.24-7.08 (m, 1H, rotamer 1 & 2), 4.83 (s, 1H, rotamer 1), 4.77 (s, 1H, rotamer 2), 2.96 (d, J=2.2 Hz, 3H, rotamers 1 & 2), 1.48 (s, 5H, rotamer 1), 1.36 (s, 5H, rotamer 2) ppm. $^{13}$C NMR (125 MHz, CDCl$_3$, mixture of rotamers) δ 192.4, 192.2, 160.8, 160.8, 158.9, 158.8, 153.7, 153.2, 147.9, 147.8, 147.7, 139.6, 139.6, 139.5, 139.4, 116.8, 116.8, 116.8, 116.7, 112.9, 111.9, 111.7, 111.6, 77.3 (2), 53.1, 52.8, 33.3, 33.0, 25.8, 25.6 ppm. IR (thin film): 1718, 1691, 1577, 1449, 1389, 1365, 1267, 1225, 1172, 1146, 1017, 994 cm$^{-1}$.

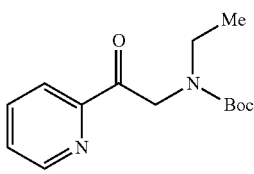

tert-Butyl ethyl(2-oxo-2-(pyridin-2-yl)ethyl)carbamate (2q)

Prepared according to general procedure B3 from 2-bromopyridine (1.3 mL, 13.6 mmol), iPrMgCl (2.0 M in THF, 7.5 mL, 15 mmol), and 1d (3.45 g, 14.0 mmol) to yield an off-yellow oil (2.59 g, 72%). R$_f$=0.48 (1:1 hexanes/EtOAc). $^1$H NMR (500 MHz, CDCl$_3$, mixture of rotamers) δ 8.63 (dd, J=12.1, 4.9 Hz, 1H, rotamer 1 & 2), 8.01 (t, J=8.6 Hz, 1H, rotamer 1 & 2), 7.83 (dt, J=19.6, 7.4 Hz, 1H, rotamer 1 & 2), 7.47 (ddd, J=18.4, 7.5, 4.9 Hz, 1H, rotamer 1 & 2), 4.90 (s, 1H, rotamer 1), 4.82 (s, 1H, rotamer 2), 3.38 (q, J=7.2 Hz, 1H, rotamer 1), 3.32 (q, J=7.2 Hz, 1H, rotamer 2), 1.47 (s, 4.5H, rotamer 1), 1.33 (s, 4.5H, rotamer 2), 1.11 (t, J=7.3 Hz, 3H, rotamer 1 & 2) ppm. $^{13}$C NMR (125 MHz, CDCl$_3$, mixture of rotamers) δ 192.4, 192.3, 151.9, 151.4, 148.5, 148.5, 145.0, 144.9, 133.1, 133.0, 132.9, 123.6, 123.5, 123.4, 117.9, 117.8, 75.7, 75.6, 49.3, 49.3, 39.5, 38.9, 24.5, 24.3, 9.8, 9.4 ppm. IR (thin film): 1715, 1686, 1421, 1391, 1365, 1282, 1251, 1224, 1167, 1142, 996 cm$^{-1}$. HRMS (ESI-TOF) m/z: [M+Na]+ Calcd for C$_{14}$H$_{20}$N$_2$O$_3$Na 287.1372; Found 287.1393.

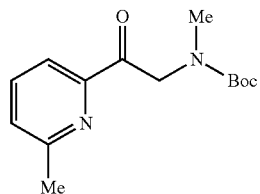

tert-Butyl methyl(2-(6-methylpyridin-2-yl)-2-oxoethyl)carbamate (2r)

Prepared according to general procedure B2 from 6-methyl-2-bromopyrididne (2.00 g, 11.62 mmol), n-BuLi (2.5 M in hexanes, 10.22 mL, 25.56 mmol), and 1a (2.70 g, 11.62 mmol) as a yellow oil (690 mg, 22%). R$_f$=0.42 (7:3 hexanes/EtOAc). $^1$H NMR (500 MHz, CDCl$_3$, mixture of rotamers) δ 7.84-7.80 (m, 1H, rotamers 1 & 2), 7.73-7.67 (m, 1H, rotamers 1 & 2), 7.34-7.30 (m, 1H, rotamers 1 & 2), 4.93 (s, 1H, rotamer 1), 4.84 (s, 1H, rotamer 2), 2.97 (s, 1.5H, rotamer 1), 2.96 (s, 1.5H, rotamer 2), 2.60 (s, 1.5H, rotamer 1), 2.57 (s, 1.5H, rotamer 2), 1.49 (s, 4.5H, rotamer 1), 1.37 (s, 4.5H, rotamer 2). $^{13}$C NMR (125 MHz, CDCl$_3$, mixture of rotamers) δ 196.7, 196.4, 158.0, 156.0, 152.0, 134.0, 136.8, 127.1, 127.0, 118.8, 118.8, 79.7, 79.6, 55.7, 55.3, 35.8, 35.6, 28.4, 28.2, 24.3, 22.3, 13.8. IR (thin film): 1712, 1690, 1591, 1479, 1451, 1388, 1365, 1292, 1221, 1171, 1021, 933 cm$^{-1}$.

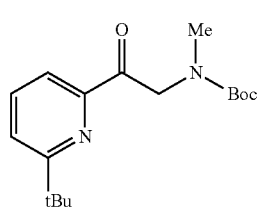

tert-Butyl (2-(6-(tert-butyl)pyridin-2-yl)-2-oxoethyl)(methyl)carbamate (2s)

Prepared according to general procedure B2 from 6-tert-butyl-2-bromopyridine (1.80 g, 8.40 mmol), n-BuLi (2.5 M in hexanes, 7.4 mL, 18.48 mmol), and 1a (1.95 g, 8.40 mmol) as a yellow oil (390 mg, 15%). R$_f$=0.50 (4:1 hexanes/EtOAc). $^1$H NMR (500 MHz, CDCl$_3$, mixture of rotamers) δ 7.82-7.73 (m, 2H, rotamers 1 & 2), 7.54-7.49 (m, 1H, rotamers 1 & 2), 4.97 (s, 1.05H, rotamer 1), 4.87 (s, 0.95H, rotamer 2), 2.97 (d, J=8.9 Hz, 3H, rotamers 1 & 2), 1.49 (s, 5H, rotamer 1), 1.43-1.34 (m, 14H, rotamers 1 & 2). $^{13}$C NMR (125 MHz, CDCl$_3$, mixture of rotamers) δ 196.8, 168.9, 168.8, 156.4, 156.0, 151.2, 151.1, 137.1, 137.0, 123.1, 123.0, 118.5, 79.7, 79.5, 55.5, 55.5, 37.6, 35.7, 35.7, 30.2, 30.1, 28.4, 28.2. IR (thin film): 1714, 1692, 1586, 1480, 1451, 1388, 1364, 1293, 1224, 1170, 1141, 1005, 993 cm$^{-1}$.

Example 5: General Procedure C (Synthesis of Deprotected α-Aminoketones)

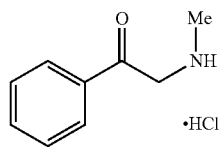

2-(Methylamino)-1-phenylethan-1-one.HCl (3a)

To a stirring solution of anhydrous MeOH (35 mL) in a 100 mL Erlenmeyer flask was added acetyl chloride (3.5 mL, 50.16 mmol) dropwise. After 10 minutes, the resulting methanolic hydrogen chloride solution was added to a 50 mL round bottom flask containing 2a (2.43 g, 10.03 mmol). After 1 h, the solvent was removed under reduced pressure yielding a fine white powder (1.69 g, 91%), which was used without further purification. $^1$H NMR (CD$_3$OD, 500 MHz): δ 8.07-8.04 (m, 1H), 7.73 (t, J=7.5 Hz, 1H), 7.59 (t, J=7.5 Hz, 2H), 4.79 (s, 2H), 2.85 (s, 3H). $^{13}$C NMR (CD$_3$OD, 125 MHz): δ 191.5, 134.5, 133.5, 128.8, 127.9, 54.0, 32.2 ppm. IR (thin film) 2945, 2911, 2808, 2756, 2434, 1690, 1597, 1574, 1472, 1449, 1424, 1373, 1242, 1013, 940, 884, 764 cm$^{-1}$. HRMS (ESI-TOF) m/z: [M+H]+ Calcd for C$_9$H$_{12}$NO 150.0919; Found 150.0919.

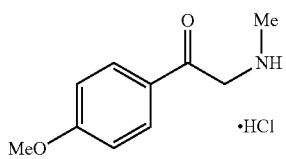

1-(4-Methoxyphenyl)-2-(methylamino)ethan-1-one.HCl (3b)

Prepared according to general procedure C with 2b (2.23 g, 8.0 mmol) as a white powder (1.59 g, 92%). $^1$H NMR (CD$_3$OD, 500 MHz): δ 8.02 (t, J=8.5 Hz, 2H), 7.09 (t, J=8.5 Hz, 2H), 4.70 (s, 2H), 3.91 (s, 3H), 2.83 (s, 3H). $^{13}$C NMR (CD$_3$OD, 125 MHz): δ 189.7, 165.1, 130.4, 126.4, 114.0, 54.9, 53.6, 32.2 ppm. IR (thin film) 2936, 2742, 2689, 1679, 1599, 1573, 1423, 1362, 1252, 1183, 1027, 1013, 944, 831 cm$^{-1}$.

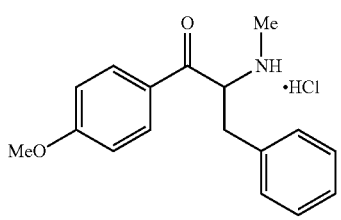

1-(4-Methoxyphenyl)-2-(methylamino)-3-phenylpropan-1-one.HCl (3c)

Prepared according to general procedure C with 2c (3.37 g, 9.12 g) as a white powder (2.48 g, 89%). $^1$H NMR (CD$_3$OD, 500 MHz): δ 7.93 (d, J=8.5 Hz, 2H), 7.27-7.21 (m, 3H), 7.16-7.12 (m, 2H), 6.99 (d, J=8.5 Hz, 2H), 5.41 (t, J=6.5 Hz, 1H), 3.88 (s, 3H), 3.77-3.27 (m, 2H), 2.71 (s, 3H). $^{13}$C NMR (CD$_3$OD, 125 MHz): δ 193.1, 165.1, 133.3, 131.3, 129.4, 128.6, 127.5, 127.0, 114.0, 63.3, 54.9, 36.9, 31.4 ppm. IR 2931, 2658, 2604, 1673, 1601, 1578, 1512, 1465, 1417, 1353, 1254, 1242, 1175, 1148, 1030, 1014, 939, 842, 767 cm$^{-1}$. HRMS (ESI-TOF) m/z: [M+H]+ Calcd for C$_{17}$H$_{20}$NO$_2$ 270.1494; Found 270.1497.

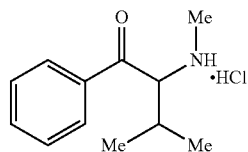

3-Methyl-2-(methylamino)-1-phenylbutan-1-one.HCl (3d)

Prepared according to general procedure C with 2d (1.25 g, 4.29 mmol) as a white powder (890 mg, 91%). $^1$H NMR (CD$_3$OD, 500 MHz): δ 8.08 (d, J=8.5 Hz, 2H), 7.76 (t, J=7.5 Hz, 1H), 7.62 (t, J=7.5 Hz, 2H), 5.20 (d, J=3 Hz, 1H), 2.74 (s, 3H), 2.45-2.35 (m, 1H), 1.16 (d, J=7 Hz, 3H), 0.92 (d, J=7 Hz, 3H). $^{13}$C NMR (CD$_3$OD, 125 MHz): δ 195.1, 134.9, 134.8, 129.0, 128.7, 68.1, 68.1, 32.2, 30.0, 17.3, 16.4 ppm. IR (thin film) 2970, 2686, 2471, 1677, 1594, 1471, 1449, 1357, 1264, 1234, 1005, 980, 941, 896, 832, 762 cm$^{-1}$. HRMS (ESI-TOF) m/z: [M+H]+ Calcd for C$_{12}$H$_{18}$NO 192.1388; Found 192.1389.

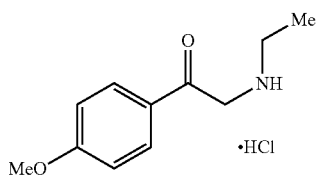

2-(Ethylamino)-1-(4-methoxyphenyl)ethan-1-one.HCl (3e)

Prepared according to general procedure C with 2e (63.90 mg, 0.21 mmol) as a pink powder (34.4 mg, 70%). $^1$H NMR (CD$_3$OD, 500 MHz): δ 7.78 (d, J=9.0 Hz, 2H), 6.78 (d, J=9.0 Hz, 2H), 3.93 (s, 2H), 3.70 (s, 3H), 2.57 (q, J=7.0 Hz, 2H), 2.26 (brs, 1H), 1.03 (t, J=7.0 Hz, 3H). $^{13}$C NMR (CD$_3$OD, 125 MHz): δ 196.2, 163.5, 129.8, 128.5, 113.7, 55.3, 55.0, 44.0, 15.2 ppm. IR (neat): 2986, 2928, 2892, 2839, 2779, 2750, 2716, 2678, 1675, 1600, 1573, 1513, 1449, 1430, 1396, 1327, 1314, 1244, 1180, 1125, 1038, 1021, 977, 907, 835, 813, 802, 612, 584 cm$^{-1}$.

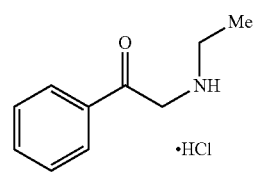

2-(Ethylamino)-1-phenylethan-1-one.HCl (3f)

Prepared according to general procedure C with 2f (0.28 g, 1.07 mmol) as a white powder (0.15 g, 70%). $^1$H NMR (CD₃OD, 500 MHz): δ 8.04 (dd, J=8.5, 1.5 Hz, 2H), 7.72 (tt, J=7.5, 1.0 Hz, 1H), 7.58 (t, J=8.0 Hz, 2H), 4.76 (s, 2H), 3.20 (q, J=7.5 Hz, 2H), 1.39 (t, J=7.5 Hz, 3H). ¹³C NMR (CD₃OD, 75 MHz): δ 191.8, 134.8, 133.8, 129.0, 128.1, 52.3, 42.8, 10.3 ppm.

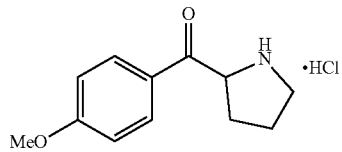

(4-Methoxyphenyl)(pyrrolidin-2-yl)methanone.HCl (3 g)

Prepared according to general procedure C with 2 g (750 mg, 2.45 mmol) as a white powder (356 mg, 60%). ¹H NMR (500 MHz, CD₃OD) δ 8.07 (d, J=9.1 Hz, 2H), 7.11 (d, J=9.1 Hz, 2H), 5.34 (dd, J=9.2, 7.1 Hz, 1H), 3.92 (s, 2H), 3.45 (td, J=7.0, 1.8 Hz, 2H), 2.70 (tdd, J=7.4, 4.7, 1.8 Hz, 1H), 2.28-2.06 (m, 1H), 2.07-1.85 (m, 2H) ppm. ¹³C NMR (125 MHz, CD₃OD) δ 191.9, 165.2, 131.3, 125.3, 114.1, 62.8, 54.9, 54.9, 46.0, 29.8, 23.8 ppm. IR (thin film) 2843, 2631, 1668, 1597, 1574, 1422, 1243, 1176, 997, 844 cm⁻¹. HRMS (ESI-TOF) m/z: [M+Na]+ Calcd for C₁₂H₁₅NO₂Na 228.1000; Found 228.1005.

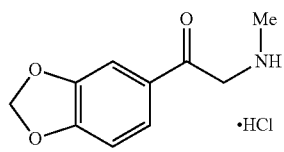

1-(Benzo[d][1,3]dioxol-5-yl)-2-(methylamino)ethan-1-one.HCl (3h)

Prepared according to general procedure C with 2h (1.21 g, 4.13 mmol) as a white powder (755 mg, 80%). ¹H NMR (500 MHz, CD₃OD) δ 7.67 (dd, J=8.2, 1.7 Hz, 1H), 7.47 (d, J=1.7 Hz, 1H), 7.00 (d, J=8.2 Hz, 1H), 6.11 (s, 2H), 4.66 (s, 2H), 2.82 (s, 3H) ppm. ¹³C NMR (125 MHz, CD₃OD) δ 189.4, 153.4, 148.7, 128.1, 125.0, 108.0, 106.9, 102.5, 53.7, 32.2 ppm. IR (thin film) 2930, 2767, 2696, 2411, 1669, 1443, 1358, 1254, 1110, 1036, 925, 827, 781 cm⁻¹. HRMS (ESI-TOF) m/z: [M+H]+ Calcd for C₁₀H₁₂NO₃ 194.0817; Found 194.0825.

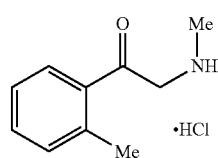

2-(Methylamino)-1-(o-tolyl)ethan-1-one.HCl (3i)

Prepared according to general procedure C with 2i (759 mg, 2.90 mmol) as a white powder (402 mg, 69%). ¹H NMR (500 MHz, CD₃OD) δ 7.89 (dd, J=7.8, 1.3 Hz, 1H), 7.57-7.46 (m, 1H), 7.44-7.34 (m, 2H), 4.69 (s, 2H), 2.84 (s, 3H), 2.59 (s, 3H) ppm. ¹³C NMR (125 MHz, CD₃OD) δ 193.7, 139.9, 133.2, 132.7, 132.2, 129.4, 126.0, 55.2, 32.1, 20.5 ppm. IR (thin film) 2922, 2689, 1684, 1570, 1455, 13346, 1233, 1002, 940, 756 cm⁻¹. HRMS (ESI-TOF) m/z: [M+H]+ Calcd for C₁₀H₁₄NO 164.1075; Found 164.1078.

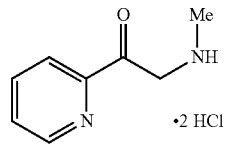

2-(Methylamino)-1-(pyridin-2-yl)ethan-1-one.2HCl (3j)

Prepared according to general procedure C with 2j (4.93 g, 19.7 mmol) as a white powder (3.97 g, 90%). ¹H NMR (500 MHz, CD₃OD) δ 8.96 (d, J=5.8 Hz, 1H), 8.89-8.70 (m, 1H), 8.27-8.17 (m, 2H), 4.91 (s, 2H), 2.78 (s, 3H) ppm. IR (thin film) 3010, 1734, 1673, 1718, 1614, 1603, 1525, 1453, 1375, 1253, 1221, 1164, 1025, 943, 855, 759 cm⁻¹. HRMS (ESI-TOF) m/z: [M+H]+ Calcd for C₈H₁₀N₂O 151.0871; Found 151.0871.

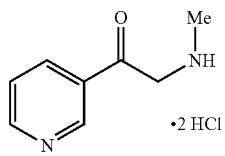

2-(Methylamino)-1-(pyridin-3-yl)ethan-1-one.2HCl (3k)

Prepared according to general procedure C with 2k (1.7 g, 6.8 mmol) as a white powder (880 mg, 58%). ¹H NMR (500 MHz, DMSO-d₆) δ 9.31 (d, J=2.0 Hz, 1H), 9.02 (dd, J=5.2, 1.7 Hz, 1H), 8.66 (dt, J=8.1, 1.9 Hz, 1H), 7.97-7.90 (m, 1H), 4.86 (t, J=5.5 Hz, 2H), 2.61 (t, J=5.2 Hz, 3H). ¹³C NMR (125 MHz, DMSO-d₆) δ 191.3, 150.8, 146.4, 140.2, 131.1, 126.3, 54.2, 33.2. IR (thin film) 2684, 2538, 2442, 1705, 1628, 1454, 1380, 1243, 1128, 944, 786 cm⁻¹. HRMS (ESI-TOF) m/z: [M+H]+ Calcd for C₈H₁N₂O 151.0871; Found 151.0870.

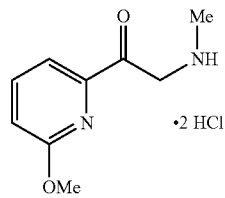

1-(6-Methoxypyridin-2-yl)-2-(methylamino)ethan-1-one.2HCl (3l)

Prepared according to general procedure C with 2l (550 mg, 1.96 mmol) as a white powder (208 mg, 42%). ¹H NMR (500 MHz, CD₃OD) δ 7.95-7.84 (m, 1H), 7.74 (d, J=7.7 Hz, 1H), 7.13 (d, J=8.5 Hz, 1H), 4.04 (s, 2H), 2.87 (s, 3H) ppm. ¹³C NMR (125 MHz, CD₃OD) δ 192.2, 163.8, 148.0, 139.7, 116.9, 115.1, 54.1, 52.9, 32.2 ppm. IR (thin film) 2929, 2747, 2687, 2444, 1705, 1592, 1470, 1419, 1367, 1335, 1278, 1236, 1152, 1043, 1019, 948, 909, 813 cm⁻¹.

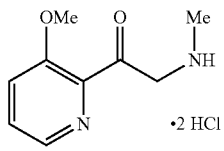

1-(3-Methoxypyridin-2-yl)-2-(methylamino)ethan-1-one.2HCl (3m)

Prepared according to general procedure C with 2m (400 mg, 1.43 mmol) as a white powder (331 mg, 91%). ¹H NMR (500 MHz, DMSO-d₆) δ 8.30 (dd, J=4.4, 1.2 Hz, 1H), 7.83-7.72 (m, 2H), 4.61 (t, J=5.9 Hz, 2H), 3.91 (s, 3H), 2.60 (t, J=5.4 Hz, 3H). ¹³C NMR (125 MHz, DMSO-d₆) δ 191.4, 156.6, 140.8, 138.8, 130.6, 122.8, 56.6, 55.3, 32.6.

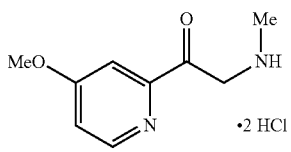

1-(4-Methoxypyridin-2-yl)-2-(methylamino)ethan-1-one.2HCl (3n)

Prepared according to general procedure C with 2n (1.8 g, 6.42 mmol) as a white powder (1.52 g, 94%). ¹H NMR (500 MHz, DMSO-d₆) δ 8.59 (d, J=5.6 Hz, 1H), 7.56 (d, J=2.5 Hz, 1H), 7.35 (dd, J=5.7, 2.6 Hz, 1H), 4.74 (t, J=5.8 Hz, 2H), 3.94 (s, 3H), 2.64 (t, J=5.3 Hz, 3H). ¹³C NMR (125 MHz, DMSO-d₆) δ 198.07, 171.75, 157.13, 156.06, 155.98, 120.04, 112.92, 61.28, 58.96, 37.82.

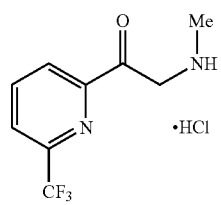

2-(Methylamino)-1-(6-(trifluoromethyl)pyridin-2-yl)ethan-1-one HCl (3o)

Prepared according to general procedure C with 2o (1.50 g, 4.71 mmol) as a white powder (490 mg, 36%). ¹H NMR (500 MHz, Methanol-d₄) δ 8.40-8.30 (m, 2H), 8.17 (dt, J=7.1, 1.3 Hz, 1H), 4.91 (s, 2H), 2.89 (s, 3H). ¹³C NMR (125 MHz, Methanol-d₄) δ 191.5, 150.7, 147.4 (q, J=35.3 Hz), 140.1, 125.2 (q, J=2.8 Hz), 124.4, 121.1 (q, J=273.4 Hz), 53.8, 32.3 ppm. IR (thin film): 3007, 2703, 2602, 1718, 1601, 1528, 1457, 1372, 1338, 1297, 1252, 1231, 1167, 1037, 777 cm⁻¹. HRMS (ESI-TOF) m/z: [M+H]+ Calcd for C₉H₁₀N₂OF₃ 219.0745; Found 219.0773.

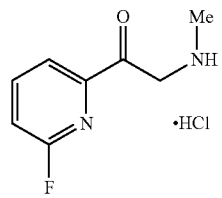

1-(6-Fluoropyridin-2-yl)-2-(methylamino)ethan-1-one.HCl (3p)

Prepared according to general procedure C with 2p (700 mg, 2.61 mmol) as a white powder (450 mg, 84%). ¹H NMR (500 MHz, Methanol-d₄) δ 8.26-8.16 (m, 1H), 8.07 (ddq, J=7.3, 1.9, 0.9 Hz, 1H), 7.45 (ddq, J=8.3, 2.7, 0.9 Hz, 1H), 4.87 (s, 2H), 2.85 (s, 3H) ppm. ¹³C NMR (125 MHz, Methanol-d₄) δ 192.5, 164.1 (d, J=243.2 Hz), 149.9, 144.5 (d, J=7.8 Hz), 141.0, 120.8 (d, J=3.8 Hz), 117.4 (d, J=230.8 Hz), 116.8 (d, J=36.5 Hz), 55.20, 33.61. IR (thin film): 3007, 2702, 2603, 1718, 1602, 1528, 1456, 1371, 1298, 1253, 1233, 1167, 1052, 1036, 777 cm⁻¹.

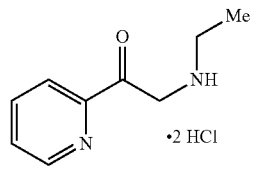

2-(Ethylamino)-1-(pyridin-2-yl)ethan-1-one.2HCl (3q)

Prepared according to general procedure C with 2q (2.40 g, 9.08 mmol) as a white powder (1.85 g, 86%). ¹H NMR (500 MHz, DMSO-d₆) δ 8.75 (d, J=4.2 Hz, 1H), 8.05 (dd, J=23.8, 7.5 Hz, 2H), 7.76 (t, J=5.7 Hz, 1H), 4.72 (t, J=5.7 Hz, 2H), 3.03 (q, J=6.4 Hz, 2H), 1.25 (t, J=7.0 Hz, 3H). ¹³C NMR (125 MHz, DMSO-d₆) δ 198.2, 155.5, 154.7 (d, J=22.4 Hz), 143.4, 134.3, 127.0, 56.8, 47.2, 16.2. IR (thin film): 3007, 2606, 1718, 1602, 1528, 1457, 1442, 1390, 1372, 1356, 1333, 1257, 1251, 1231, 1220, 1167, 1052, 1037, 776 cm⁻¹. HRMS (ESI-TOF) m/z: [M+H]+ Calcd for C₉H₁₃N₂O 165.1028; Found 165.1031.

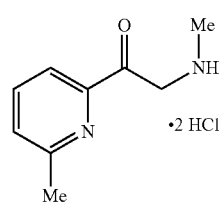

2-(Methylamino)-1-(6-methylpyridin-2-yl)ethan-1-one.2HCl (3r)

Prepared according to general procedure C with 2r (690 mg, 2.61 mmol) as a brown solid (504 mg, 81%). ¹H NMR (500 MHz, DMSO-d$_6$) δ 7.96 (t, J=7.6 Hz, 1H), 7.85 (d, J=7.4 Hz, 1H), 7.63 (d, J=7.5 Hz, 1H), 4.70 (s, 2H), 2.65-2.59 (m, 3H), 2.56 (s, 3H). $^{13}$C NMR (125 MHz, DMSO-d$_6$) δ 193.5, 158.7, 150.4, 138.6, 129.1, 119.6, 53.9, 33.1, 24.3.

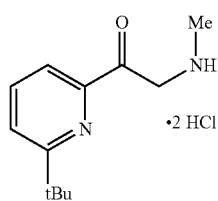

3s 1-(6-(tert-Butyl)pyridin-2-yl)-2-(methylamino)ethan-1-one.2HCl (3s)

Prepared according to general procedure C with 2s (390 mg, 1.27 mmol) as a brown solid (308 mg, 87%). $^1$H NMR (500 MHz, DMSO-d$_6$) δ 8.00 (s, 1H), 7.83 (dd, J=18.4, 5.8 Hz, 2H), 4.74 (s, 2H), 2.64 (s, 3H), 1.36 (s, 9H). $^{13}$C NMR (125 MHz, DMSO-d$_6$) δ 197.8, 162.4, 154.5, 130.4, 127.6, 113.3, 55.3, 30.7, 27.9, 14.3.

Example 6: General Procedure D (Synthesis of Cyanobenzamides)

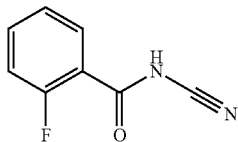

4a

N-Cyano-2-fluorobenzamide (4a)

A one-necked 500 mL round bottom flask open to the atmosphere, equipped with a magnetic stirring bar is charged with cyanamide (6.3 g, 0.15 mol) and distilled water (200 mL). Sodium hydroxide pellets (12.3 g, 0.308 mol) are then added in portions (~3×4 g) over a 15 minute period. The mixture is then stirred for 30 min. at room temperature and then cooled to 0° C. The flask is fitted with a 1000 mL addition funnel and the addition funnel charged with 2-fluorobenzoyl chloride (23.5 g, 0.15 mol). The 2-fluorobenzoyl chloride is then added dropwise over a span of 20 min. After addition of the benzoyl chloride the reaction is stirred for an additional 3 hours at room temperature. The mixture is transferred to a 500 mL separatory funnel and washed with diethyl ether (1×50 mL). The aqueous layer is then transferred to a 1-L Erlenmeyer flask equipped with a magnetic stirring bar and acidified to pH=2 with conc. HCl (approx. 15 mL). Dichloromethane (200 mL) is then added to dissolve the solids and the mixture transferred to a 500 mL separatory funnel. After separation of the layers, the aqueous fraction is extracted with dichlormethane (2×100 mL) and the combined organics dried over anhydrous Na$_2$SO$_4$. The organics were filtered through a sintered glass funnel and the resultant sodium sulfate was washed with dichloromethane (2×50 mL). The solvent was removed on a rotary evaporator and then the flask transferred to a high-vac line for 3 hours. The resulting white solid (18.7 g, 76%) was then used without further purification. R$_f$=0.16 (100% EtOAc). $^1$H NMR (500 MHz, DMSO-d$_6$) δ 7.74 (td, J=7.5, 1.8 Hz, 1H), 7.71-7.63 (m, 1H), 7.41-7.32 (m, 2H). $^{13}$C NMR (125 MHz, DMSO-d$_6$) δ 164.9, 159.9 (d, J=253.7 Hz), 135.6 (d, J=8.9 Hz), 130.9 (d, J=1.7 Hz), 125.3 (d, J=3.6 Hz), 120.3 (d, J=12.6 Hz), 117.1 (d, J=21.4 Hz), 108.7. IR (thin film) 3269, 2260, 1701, 1610, 1435, 1279, 1220, 890, 787 cm$^{-1}$.

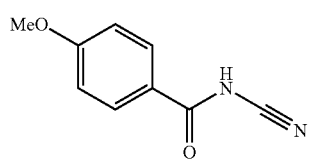

4b

N-Cyano-4-methoxybenzamide (4b)

Prepared according to general procedure D with 4-methoxybenzoyl chloride (10.03 g, 59.5 mmol) and cyanamide as a white solid (9.09 g, 87%). R$_f$=0.10 (100% EtOAc). $^1$H NMR (500 MHz, DMSO-d$_6$) δ 7.98-7.83 (m, 2H), 7.05-6.79 (m, 2H), 3.81 (s, 3H). $^{13}$C NMR (125 MHz, DMSO-d$_6$) δ 172.2, 168.0, 136.5, 128.2, 119.0, 114.4, 60.6. IR (thin film) 3233, 2256, 1670, 1601, 1450, 1257, 1180, 1022, 840, 755 cm$^{-1}$.

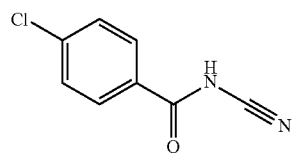

4c

4-Chloro-N-cyanobenzamide (4c)

Prepared according to general procedure D with 4-chlorobenzoyl chloride (10.52 g, 57.5 mmol) and cyanamide as a white solid (9.24 g, 86%). R$_f$=0.13 (100% EtOAc). $^1$H NMR (500 MHz, CD$_3$OD) δ 7.88 (d, J=8.6 Hz, 2H), 7.55 (d, J=8.6 Hz, 2H). $^{13}$C NMR (125 MHz, CD$_3$OD) δ 166.5, 139.8, 129.5, 129.1, 128.9, 108.1 ppm. IR (thin film) 3220, 2260, 1672, 1592, 1447, 1098, 1010, 841, 747 cm$^{-1}$.

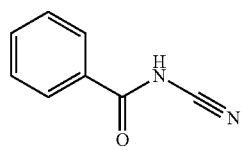

4d

N-Cyanobenzamide (4d)

Prepared according to general procedure D with benzoyl chloride (8.36 g, 59.5 mmol) and cyanamide as a white solid (6.41 g, 74%). R$_f$=0.16 (100% EtOAc). $^1$H NMR (500 MHz, CD$_3$OD) δ 7.90 (d, J=7.9 Hz, 1H), 7.75-7.63 (m, 1H), 7.54 (d, J=1.6 Hz, 1H) ppm. $^{13}$C NMR (125 MHz, CD$_3$OD) δ

167.5, 133.5, 130.5, 128.6, 127.9, 108.3 ppm. IR (thin film) 3234, 2254, 1673, 1601, 1502, 1460, 1265, 1001, 795 cm$^{-1}$.

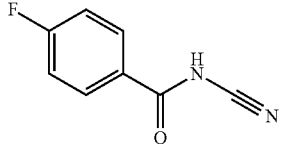

N-Cyano-4-fluorobenzamide (4e)

Prepared according to general procedure D with 4-fluorobenzoyl chloride(13.4 g, 84.5 mmol) and cyanamide as a white solid (9.85 g, 71%). $R_f$=0.18 (EtOAc). $^1$H NMR (500 MHz, CD$_3$OD) δ 8.05-7.86 (m, 2H), 7.28 (t, J=8.7 Hz, 2H) ppm. $^{13}$C NMR (125 MHz, CD$_3$OD) δ 167.1, 165.6 (d, $J_{CF}$=143.9 Hz), 130.8 (d, $J_{CF}$=9.5 Hz), 126.8 (d, $J_{CF}$=3.2 Hz), 115.7 (d, $J_{CF}$=22.5 Hz), 108.0 ppm. IR (thin film) 3252, 2254, 1678, 1593, 1455, 1236, 1166, 851, 753 cm$^{-1}$.

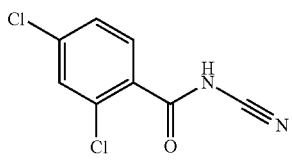

2,4-Dichloro-N-cyanobenzamide (4f)

Prepared according to general procedure D with 2-4-dicholorobenzoyl chloride (11.8 g, 84.5 mmol) and cyanamide as a white solid (12.17 g, 67%). $^1$H NMR (500 MHz, CD$_3$OD) δ 7.65 (s, 1H), 7.60 (d, J=8.3 Hz, 1H), 7.49 (d, J=8.3 Hz, 1H) ppm. $^{13}$C NMR (125 MHz, CD$_3$OD) δ 166.2, 137.9, 132.2, 130.9, 130.3, 130.0, 127.4, 107.0 ppm. IR (thin film) 3129, 2280, 1693, 1449, 1372, 1289, 1240, 1111, 904, 829, 803, 760 cm$^{-1}$.

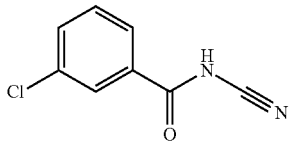

3-Chloro-N-cyanobenzamide (4 g)

Prepared according to general procedure D with 3-chlorobenzoyl chloride (10.9 g, 62.4 mmol) and cyanamide as a white solid (9.2 g, 81%). $^1$H NMR (500 MHz, CD$_3$OD) δ 7.89 (s, 1H), 7.80 (d, J=8.0 Hz, 1H), 7.67 (dd, J=1.5, 8.0 Hz, 1H), 7.52 (t, J=8.0 Hz, 1H). $^{13}$C NMR (125 MHz, CD$_3$OD) δ 165.9, 134.7, 133.3, 132.3, 130.3, 127.9, 126.2, 107.6 ppm.

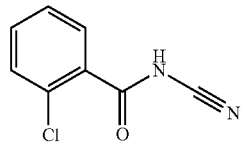

2-Chloro-N-cyanobenzamide (4h)

Prepared according to general procedure D with 2-chlorobenzoyl chloride (11.0 g, 63.0 mmol) and cyanamide as a white solid (10.2 g, 89%). $^1$H NMR (500 MHz, CD$_3$OD) δ 7.57 (d, J=7.5 Hz, 1H), 7.54 (d, J=3.5 Hz, 2H), 7.44 (sep, J=4.0 Hz, 1H). $^{13}$C NMR (125 MHz, CD$_3$OD) δ 167.12, 132.58, 132.29, 130.93, 130.14, 128.95, 127.00, 107.14 ppm.

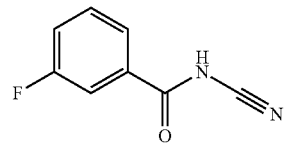

N-Cyano-3-fluorobenzamide (4i)

Prepared according to general procedure D with 3-fluorobenzoyl chloride and cyanamide as a white solid. $^1$H NMR (500 MHz, DMSO-d$_6$) δ 7.77-7.71 (m, 1H), 7.70-7.65 (m, 1H), 7.60 (td, J=8.0, 5.7 Hz, 1H), 7.53 (td, J=8.5, 2.6 Hz, 1H). $^{13}$C NMR (126 MHz, DMSO-d$_6$) δ 166.5 (d, J=2.7 Hz), 162.3 (d, J=245.5 Hz), 133.1 (d, J=7.3 Hz), 131.6 (d, J=8.1 Hz), 124.9 (d, J=2.9 Hz), 121.0 (d, J=21.0 Hz), 115.5 (d, J=23.6 Hz), 109.4. IR (thin film) 3151, 1703, 1588, 1460, 1285, 1262, 1181, 920, 902 cm$^{-1}$.

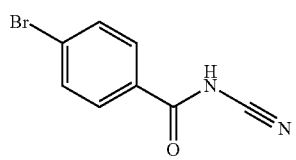

4-Bromo-N-cyanobenzamide (4j)

Prepared according to general procedure D with 4-bromobenzoyl chloride (12 g, 55 mmol) and cyanamide (4.6 g, 109 mmol) as a white solid (4.62 g, 37%). $R_f$=0.11 (100% EtOAc). $^1$H NMR (500 MHz, DMSO-d$_6$) δ 8.65-8.60 (m, 2H), 8.57 (dd, J=8.6, 2.8 Hz, 2H). $^{13}$C NMR (126 MHz, DMSO-d$_6$) δ 166.7, 132.4, 130.7, 129.8, 128.3, 109.2. IR (thin film) 3221, 2260, 2672, 1586, 1445, 1267, 1075, 838, 742 cm$^{-1}$.

Example 7: General Procedure E (Synthesis of 4-Aryl-2-N-acyl-2-aminoimidzoles)

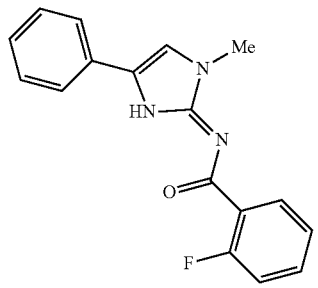

5a

2-Fluoro-N-(1-methyl-4-phenyl-1,3-dihydro-2H-imidazol-2-ylidene)benzamide (5a)

To a flame dried 50 mL round-bottom flask equipped with a magnetic stir bar under and $N_2$ atmosphere was added 4a (146 mg, 0.89 mmol) and $iPr_2NEt$ (0.42 mL, 2.42 mmol). Chlorotrimethylsilane (0.12 mL, 0.93 mmol) was then added, and the reaction was allowed to proceed at room temperature for 15 minutes. 3a (150 mg, 0.81 mmol) was then added in a single portion, and the reaction was allowed to proceed for 1.5 h. Saturated $NaHCO_3$ (10 mL) was added to quench the reaction, the reaction was partitioned and extracted with $CH_2Cl_2$ (15 mL). The organics were dried over $Na_2SO_4$, filtered, and concentrated under reduced pressure. The resulting crude material was then taken up in $CH_2Cl_2$ (10 mL) and transferred to a 25 mL round-bottom flask equipped with a magnetic stir bard under a $N_2$ atmosphere. Trifluoroacetic acid (0.1 mL) was then added to the flask, and the reaction was monitored by thin layer chromatography. After 4 hours, the reaction was quenched upon the addition of saturated $NaHCO_3$ (15 mL), and the suspension was extracted with $CH_2Cl_2$ (2×15 mL). The combined organics were collected and dried over $Na_2SO_4$, filtered, and concentrated under reduced pressure. The resulting crude material was then purified by column chromatography, eluting 6:4 hexanes/EtOAc to yield a white solid (213.3 mg, 89%). $R_f$=0.16 (6:4 hexanes/EtOAc); $^1$H NMR (CDCl$_3$, 500 MHz): δ 8.09 (dt, J=7.5 Hz, 1.5 Hz, 1H), 7.52 (d, J=8 Hz, 2H), 7.47-7.35 (m, 1H), 7.36 (t, J=7 Hz, 2H), 7.26 (t, J=7 Hz, 1H), 7.19 (t, J=8 Hz, 1H), 7.11 (dd, J=8.5 Hz, 3.5 Hz, 1H), 6.90 (s, 1H), 3.59 (s, 3H). $^{13}$C NMR (125 MHz, CDCl$_3$,) δ 169.4, 161.3 (d, $J_{CF}$=252.8 Hz), 146.1, 132.8 (d, $J_{CF}$=9.0 Hz), 131.8 (d, $J_{CF}$=1.8 Hz), 130.1, 128.9, 127.7, 124.2, 124.1 (d, $J_{CF}$=3.6 Hz), 116.5 (d, $J_{CF}$=23.5 Hz), 112.8, 32.3 ppm. IR (thin film) 1168, 1619, 1561, 1540, 1481, 1463, 1362, 1287, 1218, 903, 723 cm$^{-1}$. HRMS (ESI-TOF) m/z: [M+H]+ Calcd for $C_{17}H_{15}N_3OF$ 296.1199; Found 296.1205.

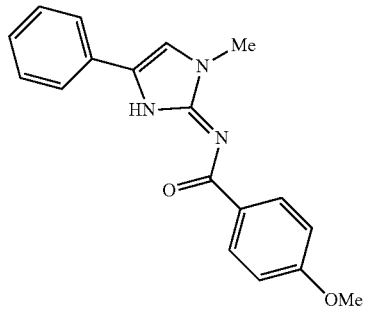

5b

4-Methoxy-N-(1-methyl-4-phenyl-1,3-dihydro-2H-imidazol-2-ylidene)benzamide (5b)

Prepared according to general procedure E from 4b (157 mg, 0.89 mmol), $iPr_2NEt$ (0.42 mL, 2.42 mmol), chlorotrimethylsilane (0.12 mL, 0.93 mmol), and 3a (150 mg, 0.81 mmol) to yield a white solid (191.4, 77%). $R_f$=0.19 (6:4 hexanes/EtOAc); $^1$H NMR (CDCl$_3$, 500 MHz): δ 8.19 (d, J=8.5 Hz, 2H), 7.47 (d, J=8 Hz, 2H), 7.32 (t, J=7.5 Hz, 2H), 7.23 (t, J=7.5 Hz, 1H), 6.87 (d, J=8.5 Hz, 2H), 6.80 (s, 1H), 3.78 (s, 3H), 3.54 (s, 3H). $^{13}$C NMR (CDCl$_3$, 125 MHz): δ 171.8, 162.1, 147.5, 130.3, 129.9, 129.4, 128.9, 128.8, 127.5, 124.0, 113.2, 112.4, 55.3, 32.1 ppm. IR (thin film) 2937, 2828, 1670, 1605, 1563, 1516, 1456, 1400, 1355, 1282, 1250, 1175, 1162, 1101, 1083, 1028, 956, 906, 846, 779 cm$^{-1}$.

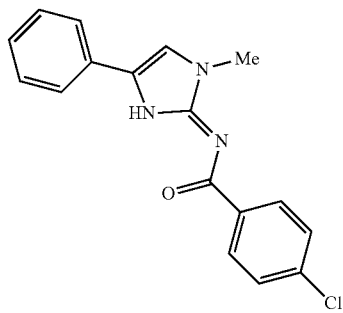

5c

4-Chloro-N-(1-methyl-4-phenyl-1,3-dihydro-2H-imidazol-2-ylidene)benzamide (5c)

Prepared according to general procedure E from 4c (161 mg, 0.89 mmol), $iPr_2NEt$ (0.42 mL, 2.42 mmol), chlorotrimethylsilane (0.12 mL, 0.93 mmol), and 3a (150 mg, 0.81 mmol) to yield a white solid (205 mg, 81%). $R_f$=0.19 (6:4 hexanes/EtOAc); $^1$H NMR (500 MHz, CDCl$_3$) δ 8.28 (d, J=6.8 Hz, 1H), 7.51-7.34 (m, 7H), 7.31-7.27 (m, 1H), 6.80 (s, 1H), 3.61 (s, 3H) ppm. $^{13}$C NMR (125 MHz, CDCl$_3$) δ 173.7, 149.6, 137.3, 131.1, 129.0, 128.9, 128.7, 128.0, 128.0, 124.1, 124.1, 111.5, 31.9 ppm. IR (thin film) 1684, 1614, 1561, 1462, 1403, 1358, 1286, 1261, 1217, 906, 753, 724 cm 1. HRMS (ESI-TOF) m/z: [M+H]+ Calcd for $C_{17}H_{15}N_3OC_1$ 312.0904; Found 312.0916.

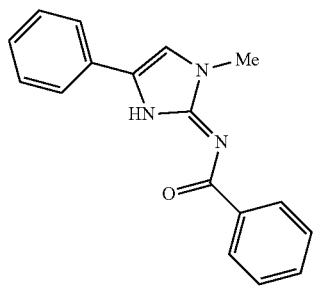

5d

N-(1-Methyl-4-phenyl-1,3-dihydro-2H-imidazol-2-ylidene)benzamide (5d)

Prepared according to general procedure E from 4d (130 mg, 0.89 mmol), iPr$_2$NEt (0.42 mL, 2.42 mmol), chlorotrimethylsilane (0.12 mL, 0.93 mmol), and 3a (150 mg, 0.81 mmol) to yield a white solid (173.8 mg, 77%). R$_f$=0.31 (6:4 hexanes/EtOAc); $^1$H NMR (CDCl$_3$, 500 MHz): δ 8.28 (dd, J=6.5 Hz, 1.5 Hz, 2H), 7.51-7.45 (m, 3H), 7.43 (t, J=7.5 Hz, 2H), 7.38 (t, J=7.5 Hz, 2H), 7.31-7.27 (m, 1H), 6.80 (s, 1H), 3.61 (s, 3H) ppm. $^{13}$C NMR (CDCl$_3$, 125 MHz): δ 173.7, 149.6, 137.3, 131.1, 129.2, 129.1, 128.9, 128.7, 128.1, 128.0, 124.4, 111.5, 31.9 ppm. IR (thin film) 1676, 1622, 1596, 1564, 1534, 1475, 1354, 1300, 1280, 1201, 1025, 905, 725 cm$^{-1}$. HRMS (ESI-TOF) m/z: [M+H]+ Calcd for C$_{17}$H$_{16}$N$_3$O 278.1293; Found 278.1305.

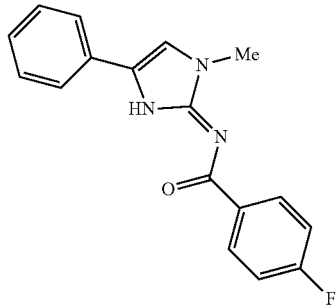

5e

4-Fluoro-N-(1-methyl-4-phenyl-1,3-dihydro-2H-imidazol-2-ylidene)benzamide (5e)

Prepared according to general procedure E from 4e (97 mg, 0.59 mmol), iPr$_2$NEt (0.38 mL, 2.16 mmol), chlorotrimethylsilane (0.08 mL, 0.62 mmol), and 3a (100 mg, 0.54 mmol) to yield a white solid (82 mg, 56%). R$_f$=0.21 (4:1 hexanes/EtOAc); $^1$H NMR (CDCl$_3$, 500 MHz): δ 8.28 (t, J=7.0 Hz, 2H), 7.46 (d, J=8.4 Hz, 2H), 7.38 (d, J=8.0 Hz, 2H), 7.30 (t, J=7.9 Hz, 1H), 7.07 (t, J=8.6 Hz, 2H), 6.77 (s, 1H), 3.62 (s, 3H) ppm. $^{13}$C NMR (CDCl$_3$, 125 MHz): δ 173.4, 164.7 (d, J$_{CF}$=248.8 Hz), 150.6, 134.1, 130.9 (d, J$_{CF}$=8.9 Hz), 129.1, 128.2, 128.2, 125.9, 124.0, 114.8 (d, J$_{CF}$=21.4 Hz), 110.9, 31.7 ppm. IR (thin film): 2945, 1678, 1622, 1596, 1563, 1476, 1404, 1355, 1273, 1221, 1145, 1084, 1054, 1013, 955, 893 cm$^{-1}$. HRMS (ESI-TOF) m/z: [M+H]+ Calcd for C$_{17}$H$_{15}$N$_3$OF 296.1199; Found 296.1217.

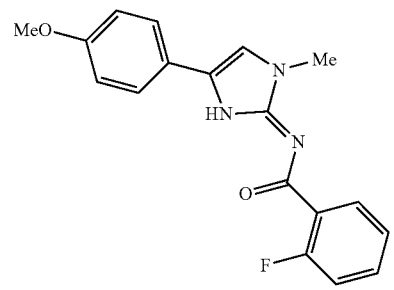

5f

2-Fluoro-N-(4-(4-methoxyphenyl)-1-methyl-1,3-dihydro-2H-imidazol-2-ylidene)benzamide (5f)

Prepared according to general procedure E from 4a (126 mg, 0.77 mmol), iPr$_2$NEt (0.37 mL, 2.1 mmol), chlorotrimethylsilane (0.10 mL, 0.81 mmol), and 3b (150 mg, 0.70 mmol) to yield a white solid (166.3 mg, 73%). R$_f$=0.16 (6:4 hexanes/EtOAc); $^1$H NMR (CDCl$_3$, 500 MHz): δ 8.11 (dt, J=8 Hz, 1 Hz, 1H), 7.47-7.38 (m, 3H), 7.19 (t, J=7.5 Hz, 1H), 7.12 (dd, J=8 Hz, 3 Hz, 1H), 6.90 (d, J=8 Hz, 2H), 6.77 (s, 1H), 3.81 (s, 3H), 3.60 (s, 3H). $^{13}$C NMR (126 MHz, Chloroform-d) δ 165.7, 156.78 (d, J=253.3 Hz), 154.70, 142.6, 127.80 (d, J=9.0 Hz), 127.16 (d, J=1.9 Hz), 120.94, 120.30, 119.25 (d, J=3.5 Hz), 117.59, 111.85 (d, J=23.7 Hz), 109.73, 106.32, 50.67, 27.45. IR (thin film) 2950, 2836, 1684, 1614, 1560, 1511, 1480, 1461, 1363, 1328, 1290, 1245, 1217, 1179, 1155, 1090, 1031, 957, 909, 897, 832, 754, 729 cm$^{-1}$. HRMS (ESI-TOF) m/z: [M+H]+ Calcd for C$_{18}$H$_{17}$N$_3$O$_2$F 326.1305; Found 326.1309.

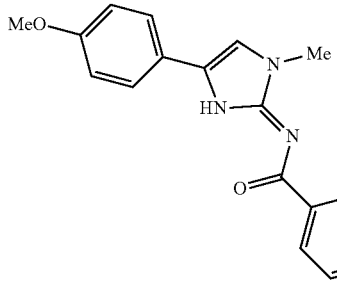

5g

4-Methoxy-N-(4-(4-methoxyphenyl)-1-methyl-1,3-dihydro-2H-imidazol-2-ylidene)benzamide (5 g)

Prepared according to general procedure E from 4b (135 mg, 0.77 mmol), iPr$_2$NEt (0.37 mL, 2.1 mmol), chlorotrimethylsilane (0.10 mL, 0.81 mmol), and 3b (150 mg, 0.70 mmol) to yield a white solid (171 mg, 73%). R$_f$=0.09 (6:4 hexanes/EtOAc); $^1$H NMR (CDCl$_3$, 500 MHz): δ 8.24 (d J=8.5 Hz, 2H), 7.43 (d, J=8.5 Hz, 2H), 6.93 (dd, J=9 Hz, 2 Hz, 4H), 6.70 (s, 1H), 3.87 (s, 3H), 3.84 (s, 3H), 3.64 (s, 3H). $^{13}$C NMR (CDCl$_3$, 125 MHz): δ 173.6, 162.0, 159.5, 149.9, 130.5, 130.2, 128.6, 125.6, 121.3, 114.5, 113.2, 109.9, 55.4, 55.3, 31.8 ppm. IR (thin film) 2937, 2837, 1670, 1603, 1562, 1513, 1458, 1363, 1308, 1245, 1175, 1163, 1105, 1029, 957, 908, 893, 883 cm$^{-1}$.

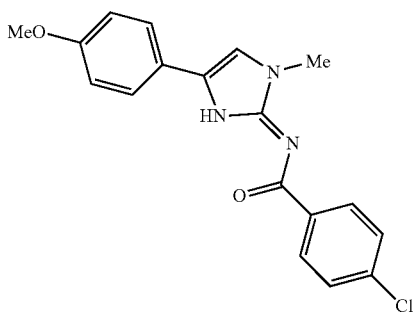

5ga

4-Chloro-N-(4-(4-methoxyphenyl)-1-methyl-1,3-dihydro-2H-imidazol-2-ylidene)benzamide (5ga)

Prepared according to general procedure E from 4c (138 mg, 0.77 mmol), iPr$_2$NEt (0.37 mL, 2.1 mmol), chlorotrimethylsilane (0.10 mL, 0.81 mmol), and 5b (150 mg, 0.70 mmol) to yield a white solid (184.8 mg, 77%). R$_f$=0.24 (6:4 hexanes/EtOAc); $^1$H NMR (CDCl$_3$, 500 MHz): δ 12.62 (br s, 1H), 8.24 (dd, J=8.5 Hz, 1.5 Hz, 2H), 7.44-7.37 (m, 4H), 6.95 (dd, J=8.5 Hz, 1.5 Hz, 2H), 6.69 (s, 1H), 3.85 (s, 3H), 3.67 (s, 3H). $^{13}$C NMR (CDCl$_3$, 125 MHz): δ 173.7, 159.7, 151.0, 136.8, 136.8, 130.2, 128.1, 125.6, 125.3, 120.6, 114.6, 109.5, 55.4, 31.6 ppm. IR (thin film) 2937, 2836, 1625, 1564, 1513, 1478, 1361, 1292, 1252, 1180, 1087, 1036, 1014, 892, 830, 769 cm$^{-1}$. HRMS (ESI-TOF) m/z: [M+H]+ Calcd for C$_{18}$H$_{17}$N$_3$O$_2$Cl 342.1009; Found 342.1017.

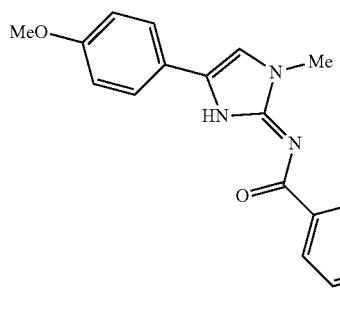

5i

4-Fluoro-N-(4-(4-methoxyphenyl)-1-methyl-1,3-dihydro-2H-imidazol-2-ylidene)benzamide (5i)

Prepared according to general procedure E from 4e (84 mg, 0.51 mmol), iPr$_2$NEt (0.33 mL, 1.84 mmol), chlorotrimethylsilane (0.07 mL, 0.53 mmol), and 3b (100 mg, 0.46 mmol) to yield a white solid (87 mg, 58%). R$_f$=0.52 (EtOAc); $^1$H NMR (CDCl$_3$, 500 MHz): δ 8.26 (t, J=7.2 Hz, 2H), 7.35 (d, J=7.7 Hz, 2H), 7.05 (t, J=8.3 Hz, 2H), 6.88 (d, J=7.8 Hz, 2H), 6.61 (s, 1H), 3.78 (s, 3H), 3.7 (s, 3H). $^{13}$C NMR (CDCl$_3$, 125 MHz): δ 173.2, 164.7 (d, J$_{CF}$=248.8 Hz), 159.6, 150.4, 134.2, 130.9 (d, J$_{CF}$=8.7 Hz), 125.8, 125.5, 120.8, 114.7 (d, J$_{CF}$=22.1 Hz), 114.5, 109.7, 55.3, 31.7 ppm. IR (thin film): 1626, 1600, 1567, 1540, 1513, 1478, 1365, 1253, 1189, 1147, 1078, 903 cm$^{-1}$.

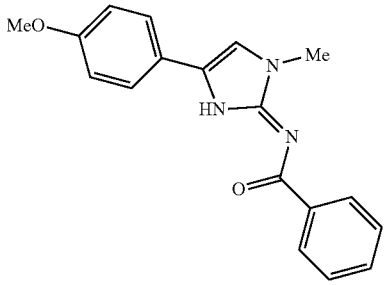

5h

N-(4-(4-Methoxyphenyl)-1-methyl-1,3-dihydro-2H-imidazol-2-ylidene)benzamide (5h)

Prepared according to general procedure E from 4d (113 mg, 0.77 mmol), iPr$_2$NEt (0.37 mL, 2.1 mmol), chlorotrimethylsilane (0.10 mL, 0.81 mmol), and 3b (150 mg, 0.70 mmol) to yield a white solid (168 mg, 78%). $^1$H NMR (CDCl$_3$, 500 MHz): δ 8.27 (d, J=6.5 Hz, 2H), 7.46-7.38 (m, 3H), 7.35 (d, J=9 Hz, 2H), 6.86 (d, J=9 Hz, 2H), 6.62 (s, 1H), 3.76 (s, 3H), 3.55 (s, 3H). $^{13}$C NMR (CDCl$_3$, 125 MHz): δ 173.9, 159.5, 149.8, 137.7, 130.9, 128.7, 128.0, 125.5, 121.3, 114.5, 110.1, 55.3, 31.7 ppm. IR (thin film) 1623, 1566, 1539, 1513, 1478, 1365, 1299, 1251, 1180, 1036, 904, 831, 722 cm$^{-1}$. HRMS (ESI-TOF) m/z: [M+H]+ Calcd for C$_{18}$H$_{18}$N$_3$O$_2$ 308.1399; Found 308.1412.

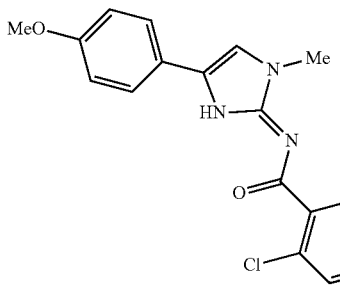

5j

2,4-Dichloro-N-(4-(4-methoxyphenyl)-1-methyl-1,3-dihydro-2H-imidazol-2-ylidene)benzamide (5j)

Prepared according to general procedure E from 4f (165 mg, 0.77 mmol), iPr$_2$NEt (0.50 mL, 2.80 mmol), chlorotrimethylsilane (0.10 mL, 0.81 mmol), and 3b (150 mg, 0.70 mmol) to yield a white solid (218 mg, 83%). R$_f$=0.41 (EtOAc); $^1$H NMR (CDCl$_3$, 500 MHz): δ 7.82 (d, J=8.5, 1H), 7.40-7.31 (m, 2H), 7.20 (d, J=8.2 Hz, 1H), 6.88 (d, J=9.1 Hz, 2H), 6.67 (s, 1H), 3.78 (s, 3H), 3.55 (s, 3H), ppm. $^{13}$C NMR (CDCl$_3$, 125 MHz): δ 173.1, 159.6, 136.6, 136.5, 135.3, 133.1, 131.8, 130.2, 126.6, 125.7, 121.0, 120.9, 114.5, 110.2, 55.3, 31.9 ppm. IR (thin film): 2936, 2826, 1688, 1625, 1555, 1511, 1464, 1357, 1326, 1291, 1246, 1197, 1178, 1139, 1110, 1032, 957, 895 cm$^{-1}$.

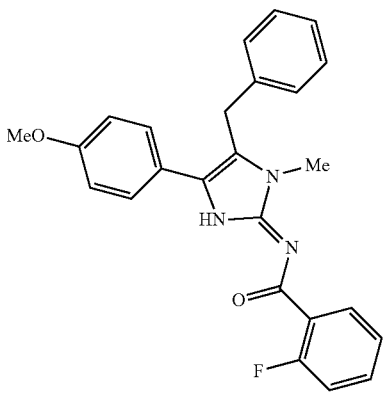

N-(5-Benzyl-4-(4-methoxyphenyl)-1-methyl-1,3-dihydro-2H-imidazol-2-ylidene)-2-fluorobenzamide (5k)

Prepared according to general procedure E from 4a (67 mg, 0.41 mmol), iPr$_2$NEt (0.26 mL, 1.5 mmol), chlorotrimethylsilane (0.06 mL, 0.43 mmol), and 3c (150 mg, 0.37 mmol) to yield a white solid (136 mg, 89%). R$_f$=0.19 (6:4 hexanes/EtOAc); $^1$H NMR (CDCl$_3$, 500 MHz): δ 8.11 (s, 1H), 7.44-7.30 (m, 5H), 7.30-7.23 (m, 1H), 7.21-7.13 (m, 3H), 7.13-7.07 (m, 1H), 6.96-6.89 (m, 2H), 4.12 (s, 2H), 3.81 (s, 3H), 3.38 (s, 3H). $^{13}$C NMR (125 MHz, CDCl$_3$) δ 171.8, 161.6 (d, J=254.1 Hz), 159.6, 148.7, 137.0, 132.0 (d, J=8.8 Hz), 131.7 (d, J=1.9 Hz), 129.1, 128.1, 127.7, 127.1, 126.3, 124.3, 123.7 (d, J=3.8 Hz), 121.9, 120.3, 116.6 (d, J=23.4 Hz), 114.5, 55.3, 29.3, 29.2 ppm. IR (thin film) 2936, 2837, 1684, 1567, 1513, 1494, 1480, 1452, 1355, 1290, 1248, 1177, 1031, 994, 906, 833, 758 cm$^{-1}$. HRMS (ESI-TOF) m/z: [M+H]+ Calcd for C$_{25}$H$_{23}$N$_3$O$_2$F 416.1774; Found 416.1776.

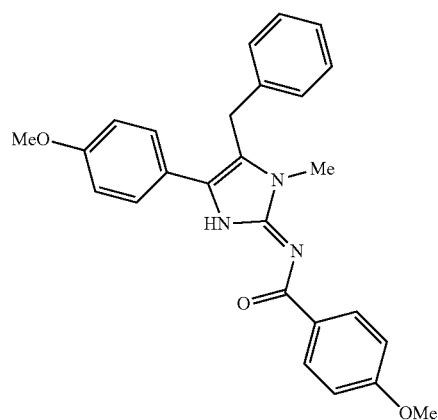

N-(5-Benzyl-4-(4-methoxyphenyl)-1-methyl-1,3-dihydro-2H-imidazol-2-ylidene)-4-methoxybenzamide (5l)

Prepared according to general procedure E from 4b (73 mg, 0.41 mmol), iPr$_2$NEt (0.26 mL, 1.5 mmol), chlorotrimethylsilane (0.06 mL, 0.43 mmol), and 3c (150 mg, 0.37 mmol) to yield a white solid (113 mg, 72%). R$_f$=0.16 (6:4 hexanes/EtOAc); $^1$H NMR (CDCl$_3$, 500 MHz): δ 8.26 (d, J=9 Hz, 2H), 7.40-7.36 (m, 2H), 7.36-7.32 (m, 2H), 7.29-7.24 (m, 1H), 7.17 (d, J=7 Hz, 2H), 6.92 (dd, J=8.5 Hz, 2 Hz, 4H), 4.10 (s, 2H), 3.84 (s, 3H), 3.81 (s, 3H), 3.40 (s, 3H). $^{13}$C NMR (CDCl$_3$, 125 MHz): δ 174.2, 161.8, 159.6, 150.4, 137.0, 130.9, 130.5, 129.1, 128.1, 127.7, 127.1, 122.8, 121.7, 119.6, 114.6, 113.1, 55.4, 55.3, 29.3, 29.0 ppm. IR (thin film) 2935, 2837, 1670, 1568, 1514, 1454, 1351, 1291, 1246, 1165, 1113, 1029, 992, 906, 893, 833, 778 cm$^{-1}$. HRMS (ESI-TOF) m/z: [M+H]+ Calcd for C$_{26}$H$_{26}$N$_3$O$_3$ 428.1974; Found 428.1981.

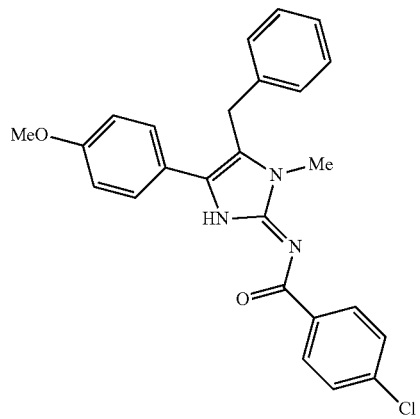

N-(5-Benzyl-4-(4-methoxyphenyl)-1-methyl-1,3-dihydro-2H-imidazol-2-ylidene)-4-chlorobenzamide (5m)

Prepared according to general procedure E from 4c (74 mg, 0.41 mmol), iPr$_2$NEt (0.26 mL, 1.5 mmol), chlorotrimethylsilane (0.06 mL, 0.43 mmol), and 3c (150 mg, 0.37 mmol) to yield a white solid (130 mg, 81%). R$_f$=0.34 (6:4 hexanes/EtOAc); $^1$H NMR (CDCl$_3$, 500 MHz): δ 8.23 (d, J=8 Hz, 2H), 7.40-7.35 (m, 4H), 7.35-7.32 (m, 2H), 7.30-7.26 (m, 1H), 7.17 (d, J=7.5 Hz, 2H), 6.93 (d, J=9 Hz, 2H), 4.10 (s, 2H), 3.82 (s, 3H), 3.40 (s, 3H). $^{13}$C NMR (CDCl$_3$, 125 MHz): δ 173.6, 159.7, 150.6, 137.0, 136.8, 136.7, 130.2, 129.1, 128.1, 128.0, 127.6, 127.2, 122.5, 121.2, 119.8, 114.6, 55.4, 29.3, 29.0 ppm. IR (thin film) 2934, 2836, 1634, 1566, 1512, 1476, 1349, 1291, 1249, 1178, 1086, 1031, 1012, 992, 907, 891, 832, 768 cm$^{-1}$. HRMS (ESI-TOF) m/z: [M+H]+ Calcd for C$_{25}$H$_{23}$N$_3$O$_2$C; 432.1479; Found 432.1483.

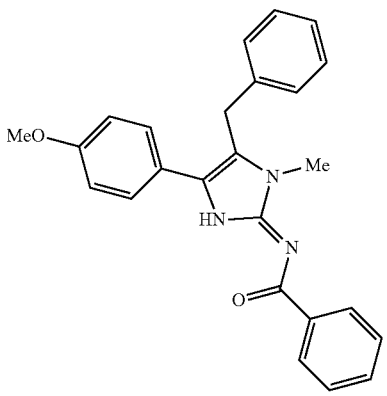

N-(5-Benzyl-4-(4-methoxyphenyl)-1-methyl-1,3-dihydro-2H-imidazol-2-ylidene)benzamide (5n)

Prepared according to general procedure E from 4d (60 mg, 0.41 mmol), iPr$_2$NEt (0.26 mL, 1.5 mmol), chlorotrimethylsilane (0.06 mL, 0.43 mmol), and 3c (150 mg, 0.37 mmol) to yield a white solid (125 mg, 85%). R$_f$=0.25 (6:4 hexanes/EtOAc); $^1$H NMR (CDCl$_3$, 500 MHz): δ 8.32 (d, J=7.5 Hz, 2H), 7.46-7.40 (m, 3H), 7-40-7.37 (m, 2H), 7.37-7.32 (m, 2H), 7.30-7.25 (m, 1H), 7.17 (d, J=7.5 Hz, 2H), 6.93 (d, J=8.5 Hz, 2H), 4.10 (s, 2H), 3.81 (s, 3H), 3.41 (s, 3H). $^{13}$C NMR (CDCl$_3$, 125 MHz): δ 174.6, 159.6, 150.5, 138.3, 137.0, 130.7, 129.1, 128.7, 128.7, 128.1, 127.9, 127.7, 127.1, 122.7, 121.5, 119.8, 114.6, 55.4, 29.3, 29.0 ppm. IR (thin film) 3061, 2934, 2836, 1676, 1635, 1568, 1541, 1513, 1453, 1350, 1291, 1248, 1177, 1066, 1028, 993, 907, 891, 832 cm$^{-1}$. HRMS (ESI-TOF) m/z: [M+H]+ Calcd for C$_{25}$H$_{43}$N$_3$O$_2$ 398.1869; Found 398.1876.

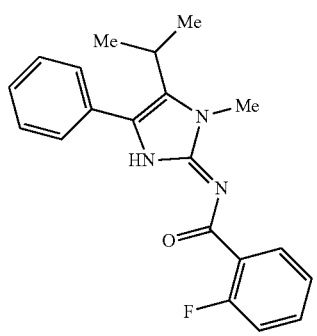

2-Fluoro-N-(5-isopropyl-1-methyl-4-phenyl-1,3-dihydro-2H-imidazol-2-ylidene)benzamide (5o)

Prepared according to general procedure E from 4a (118 mg, 0.72 mmol), iPr$_2$NEt (0.34 mL, 1.98 mmol), chlorotrimethylsilane (0.1 mL, 0.76 mmol), and 3d (150 mg, 0.66 mmol) to yield a white solid (152 mg, 66%). R$_f$=0.29 (6:4 hexanes/EtOAc); $^1$H NMR (CDCl$_3$, 500 MHz): δ 8.09 (dt, J=7.5 Hz, 1.5 Hz, 1H), 7.43-7.33 (m, 6H), 7.16 (t, J=8 Hz, 1H), 7.08 (dd, J=8.5 Hz, 2.5 Hz, 1H), 3.67 (s, 3H), 3.29-3.22 (m, 1H), 1.31 (d, J=7.5 Hz, 6H). $^{13}$C NMR (125 MHz, CDCl$_3$) δ 172.1, 161.5 (d, J$_{CF}$=254.1 Hz), 149.0, 131.8, 131.7 (d, J$_{CF}$=2.4 Hz), 130.2, 128.7 (d, J$_{CF}$=7.2 Hz), 128.3, 128.2, 126.7 (d, J$_{CF}$=9.7 Hz), 123.6 (d, J$_{CF}$=3.6 Hz), 121.6, 116.5 (d, J$_{CF}$=23.3 Hz), 30.2, 24.5, 21.3 ppm. IR (thin film) 2969, 1685, 1565, 1481, 1447, 1357, 1260, 1219, 1154, 1093, 1047, 1033, 987, 907, 897, 757 cm$^{-1}$.

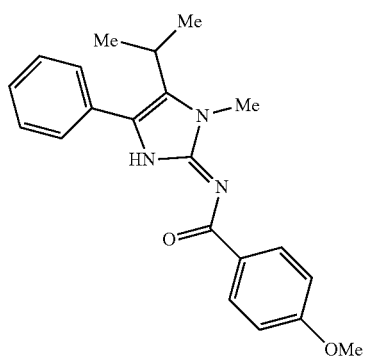

N-(5-Isopropyl-1-methyl-4-phenyl-1,3-dihydro-2H-imidazol-2-ylidene)-4-methoxybenzamide (5p)

Prepared according to general procedure E from 4b (127 mg, 0.72 mmol), iPr$_2$NEt (0.34 mL, 1.98 mmol), chlorotrimethylsilane (0.1 mL, 0.76 mmol), and 3d (150 mg, 0.66 mmol) to yield a white solid (158.8 mg, 66%). R$_f$=0.26 (6:4 hexanes/EtOAc); $^1$H NMR (CDCl$_3$, 500 MHz): δ 8.24 (d, J=8.5 Hz, 2H), 7.43-7.36 (m, 4H), 7.36-7.32 (m, 1H), 6.90 (d, J=8.5 Hz, 2H), 3.81 (s, 3H), 3.68 (s, 3H), 3.28-3.21 (m, 1H), 1.29 (d, J=7.5 Hz, 6H). $^{13}$C NMR (CDCl$_3$, 125 MHz): δ 174.0, 161.8, 150.2, 131.0, 130.5, 130.2, 128.7, 128.6, 128.3, 127.7, 120.8, 113.1, 55.3, 30.0, 24.5, 21.3 ppm. IR (thin film) 2968, 1669, 1567, 1538, 1464, 1354, 1307, 1248, 1178, 1162, 1030, 987, 906, 779, 766 cm$^{-1}$. HRMS (ESI-TOF) m/z: [M+H]+ Calcd for C$_{21}$H$_{24}$N$_3$O$_2$ 350.1869; Found 250.1870.

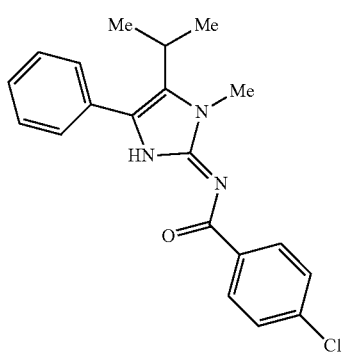

4-Chloro-N-(5-isopropyl-1-methyl-4-phenyl-1,3-dihydro-2H-imidazol-2-ylidene)benzamide (5q)

Prepared according to general procedure E from 4c (130 mg, 0.72 mmol), iPr$_2$NEt (0.34 mL, 1.98 mmol), chlorotrimethylsilane (0.1 mL, 0.76 mmol), and 4d (150 mg, 0.66 mmol) to yield a white solid (150 mg, 64%). R$_f$=0.42 (6:4 hexanes/EtOAc); $^1$H NMR (CDCl$_3$, 500 MHz): δ 8.26-8.20

(m, 2H), 7.45-7.41 (m, 2H), 7.40-7.33 (m, 5H), 3.72 (s, 3H), 3.30-3.22 (m, 1H), 1.32 (d, J=7 Hz, 6H). $^{13}$C NMR (CDCl$_3$, 125 MHz): δ 173.6, 150.6, 137.2, 136.5, 130.2, 129.6, 128.8, 128.6, 128.5, 128.0, 127.7, 120.1, 30.0, 24.5, 21.3 ppm. IR (thin film) 2969, 1623, 1565, 1536, 1473, 1395, 1339, 1163, 1087, 1046, 1013, 987, 906, 892, 851, 767 cm$^{-1}$. HRMS (ESI-TOF) m/z: [M+H]+ Calcd for C$_{20}$H$_{21}$N$_3$OC$_1$ 354.1373; Found 354.1377.

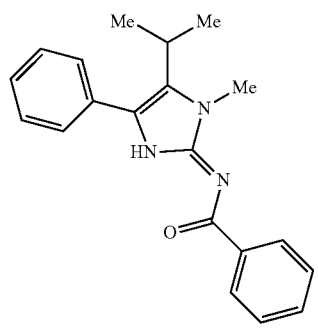

N-(5-Isopropyl-1-methyl-4-phenyl-1,3-dihydro-2H-imidazol-2-ylidene)benzamide (5r)

Prepared according to general procedure E from 4d (105 mg, 0.72 mmol), iPr$_2$NEt (0.34 mL, 1.98 mmol), chlorotrimethylsilane (0.1 mL, 0.76 mmol), and 3d (150 mg, 0.66 mmol) to yield a white solid (153 mg, 73%). R$_f$=0.39 (6:4 hexanes/EtOAc); $^1$H NMR (CDCl$_3$, 500 MHz): δ 8.34-8.29 (m, 2H), 7.47-7.35 (m, 8H), 3.71 (s, 3H), 3.29-3.22 (m, 1H), 1.31 (d, J=7 Hz, 6H). $^{13}$C NMR (CDCl$_3$, 125 MHz): δ 174.5, 150.5, 138.5, 130.6, 129.9, 128.8, 128.7, 128.6, 128.4, 127.9, 127.7, 120.4, 30.0, 24.5, 21.3 ppm. IR (thin film) 3061, 2968, 1676, 1622, 1592, 1567, 1540, 1466, 1353, 1300, 1168, 1066, 1046, 1024, 987, 907, 892, 766 cm$^{-1}$. HRMS (ESI-TOF) m/z: [M+H]+ Calcd for C$_{20}$H$_{22}$N$_3$O 320.1763; Found 320.1769.

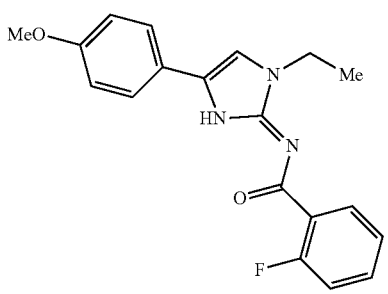

N-(1-Ethyl-4-(4-methoxyphenyl)-1,3-dihydro-2H-imidazol-2-ylidene)-2-fluorobenz-amide (5s)

Prepared according to general procedure E using 4a (34.40 mg, 0.15 mmol), iPr$_2$NEt (0.09 mL, 0.53 mmol), chlorotrimethylsilane (0.02 mL, 0.18 mmol), and 3e (29.50 mg, 0.18 mmol) to yield a white solid (40.20 mg, 79%). R$_f$=0.4 (3:2 hexanes/EtOAc); $^1$H NMR (CDCl$_3$, 500 MHz): δ 8.10 (td, J=7.5, 2.0 Hz, 1H), 7.45 (d, J=8.5 Hz, 2H), 7.42-7.37 (m, 1H), 7.18 (t, J=7.5 Hz, 1H), 7.10 (dd, J=8.5, 11.5 Hz, 1H), 6.91 (d, J=8.5 Hz. 2H), 6.78 (s, 1H), 4.03 (q, J=7.5 Hz, 2H), 3.81 (s, 3H), 1.44 (t, J=7.5 Hz, 3H). $^{13}$C NMR (CDCl$_3$, 125 MHz): δ 162.6, 160.6, 159.4, 132.2 (d, J$_{CF}$=37.0 Hz), 131.8 (d, J$_{CF}$=8.0 Hz), 125.6, 123.7 (d, J$_{CF}$=15.0 Hz), 122.0, 116.6, 116.2, 114.4, 108.8, 55.3, 40.1, 14.9.

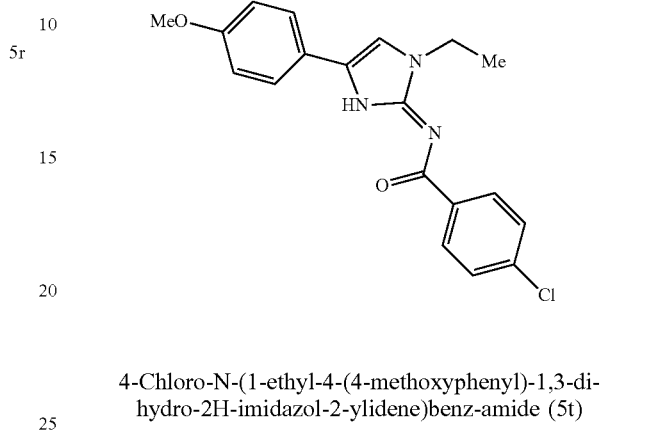

4-Chloro-N-(1-ethyl-4-(4-methoxyphenyl)-1,3-dihydro-2H-imidazol-2-ylidene)benz-amide (5t)

Prepared according to general procedure E using 4c (0.10 g, 0.43 mmol), iPr$_2$NEt (0.27 mL, 1.56 mmol), chlorotrimethylsilane (0.07 mL, 0.54 mmol), and 3e (94.27 mg, 0.52 mmol) to yield a white solid (76.0 mg, 52%). R$_f$=0.3 (3:1 hexanes/EtOAc); $^1$H NMR (CDCl$_3$, 500 MHz): δ 12.60 (brs, 1H), 8.22 (d, J=9.0 Hz, 2H), 7.38 (dd, J=8.5, 12.5 Hz, 4H), 6.92 (d, J=8.5 Hz, 2H), 6.69 (s, 1H), 4.07 (q, J=7.5 Hz, 2H), 3.81 (s, 3H), 1.45 (t, J=7.5 Hz, 3H). $^{13}$C NMR (CDCl$_3$, 125 MHz): δ 173.6, 159.6, 150.4, 136.9, 136.6, 130.2, 128.0, 125.5, 125.3, 120.7, 114.6, 107.8, 55.4, 39.8, 14.8 ppm.

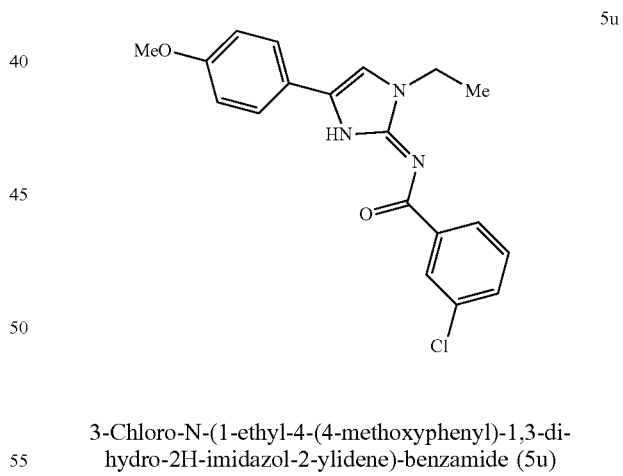

3-Chloro-N-(1-ethyl-4-(4-methoxyphenyl)-1,3-dihydro-2H-imidazol-2-ylidene)-benzamide (5u)

Prepared according to general procedure E using 4 g (0.15 g, 0.65 mmol), iPr$_2$NEt (0.41 mL, 2.35 mmol), chlorotrimethylsilane (0.10 mL, 0.81 mmol), and 3e (0.14 g, 0.78 mmol) to yield a white solid (0.22 g, quant). R$_f$=0.3 (2:1 hexanes/EtOAc); $^1$H NMR (CDCl$_3$, 500 MHz): δ 12.53 (brs, 1H), 8.26 (s, 1H), 8.14 (d, J=7.5 Hz, 1H), 7.37 (d, J=9.0 Hz, 1H), 7.31 (dd, J=9.0, 15.0 Hz, 3H), 6.85 (d, J=8.5 Hz, 2H), 6.64 (s, 1H), 4.00 (q, t=7.5 Hz, 2H), 3.74 (s, 3H), 1.38 (t, J=7.5 Hz, 3H). $^{13}$C NMR (CDCl$_3$, 125 MHz): δ 173.0, 159.5, 150.2, 140.4, 133.8, 130.5, 129.1, 128.9, 126.9, 125.4, 125.2, 120.5, 114.5, 107.9, 55.3, 39.8, 14.8 ppm.

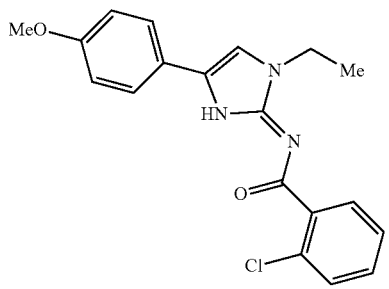

2-Chloro-N-(1-ethyl-4-(4-methoxyphenyl)-1,3-dihydro-2H-imidazol-2-ylidene)-benzamide (5v)

Prepared according to general procedure E using 4h (0.15 g, 0.65 mmol), iPr$_2$NEt (0.41 mL, 2.35 mmol), chlorotrimethylsilane (0.10 mL, 0.81 mmol), and 3e (0.14 g, 0.78 mmol) to yield a white solid (0.22 g, quant). R$_f$=0.5 (2:1 hexanes/EtOAc); $^1$H NMR (CDCl$_3$, 500 MHz): δ (12.50 (brs, 1H), 7.90-7.86 (m 1H), 7.44-7.38 (m, 3H), 7.31-7.26 (m, 2H), 6.93 (d, J=9.0 Hz, 2H), 6.74 (s, 1H), 4.05 (q, J=7.5 Hz, 2H), 3.83 (s, 3H), 1.44 (t, J=7.5 Hz, 3H). $^{13}$C NMR (CDCl$_3$, 125 MHz): δ 173.5, 159.4, 147.6, 147.5, 147.5, 138.0, 131.9, 130.5, 130.4, 130.3, 130.2, 128.0, 126.4, 125.6, 121.8, 114.4, 109.0, 55.3, 40.2, 14.9 ppm.

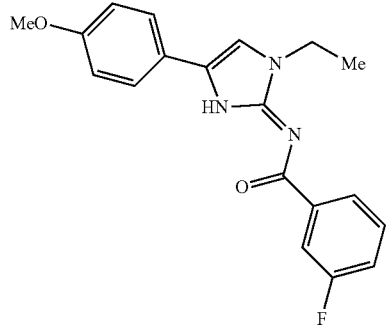

N-(1-Ethyl-4-(4-methoxyphenyl)-1,3-dihydro-2H-imidazol-2-ylidene)-3-fluoro-benzamide (5x)

Prepared according to general procedure E using 4i (0.10 g, 0.43 mmol), iPr$_2$NEt (0.27 mL, 1.56 mmol), chlorotrimethylsilane (0.07 mL, 0.54 mmol), and 3e (85.7 mg, 0.52 mmol) to yield a white solid (0.14 g, 98%). R$_f$=0.4 (5:2 hexanes/EtOAc); $^1$H NMR (CDCl$_3$, 500 MHz): δ 12.61 (brs, 1H), 8.06 (d, J=8.0 Hz, 1H), 7.99 (ddd, J=10.0, 2.5, 1.5 Hz, 1H), 7.41 (d, J=9.0 Hz, 2H), 7.40-7.35 (m, 1H), 7.14 (td, J=8.5, 2.0 Hz, 1H), 6.94 (d, J=8.0 Hz, 2H), 6.71 (s, 1H), 4.11 (q, J=7.5 Hz, 2H), 3.83 (s, 3H), 1.47 (t, J=7.5 Hz, 3H).

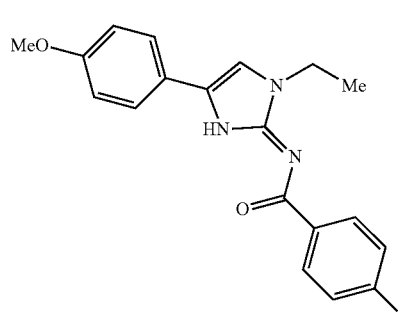

N-(1-Ethyl-4-(4-methoxyphenyl)-1,3-dihydro-2H-imidazol-2-ylidene)-4-fluoro-benzamide (5w)

Prepared according to general procedure E using 4e (0.10 g, 0.43 mmol), iPr$_2$NEt (0.27 mL, 1.56 mmol), chlorotrimethylsilane (0.07 mL, 0.54 mmol), and 3e (85.7 mg, 0.52 mmol) to yield a white solid (0.14 g, 96%). R$_f$=0.7 (1:1 hexanes/EtOAc); $^1$H NMR (CDCl$_3$, 500 MHz): δ 12.56 (brs, 1H), 8.28 (t, J=9.0 Hz, 2H), 7.34 (d, J=8.5 Hz, 2H), 7.05 (t, J=8.5 Hz, 2H), 6.86 (d, J=8.5 Hz, 2H), 6.64 (s, 1H), 4.00 (q, J=7.0 Hz, 2H), 3.75 (s, 3H), 1.38 (t, J=7.0 Hz, 3H). $^{13}$C NMR (CDCl$_3$, 125 MHz): δ 173.4, 165.6, 163.6, 159.5, 150.2, 134.6, 135.6, 131.0 (d, J$_{CF}$=34.5 Hz), 125.4 (d, J$_{CF}$=20.0 Hz), 120.8, 114.7, 114.5 (d, J$_{CF}$=8.5 Hz), 107.8, 55.3, 39.8, 14.7.

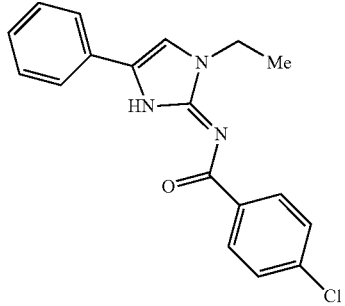

4-Chloro-N-(1-ethyl-4-phenyl-1,3-dihydro-2H-imidazol-2-ylidene)benzamide (5y)

Prepared according to general procedure E using 4c (0.07 g, 0.35 mmol), iPr$_2$NEt (0.22 mL, 1.26 mmol), chlorotrimethylsilane (0.05 mL, 0.44 mmol), and 3f (75.85 mg, 0.42 mmol) to yield a white solid (102.8 mg, 90%). R$_f$=0.2 (5:1 hexanes/EtOAc); $^1$H NMR (CDCl$_3$, 500 MHz): δ 12.72 (brs, 1H), 8.23 (d, J=8.5 Hz, 2H), 7.49 (d, J=8.0 Hz, 2H), 7.45-7.35 (m, 4H), 7.32 (t, J=7.5 Hz, 1H), 6.83 (s, 1H), 4.11 (q, J=7.5 Hz, 2H), 1.48 (t, J=7.5 Hz, 3H). $^{13}$C NMR (CDCl$_3$, 125 MHz): δ 173.8, 150.8, 136.8, 136.8, 130.2, 129.2, 128.2, 128.0, 125.0, 124.2, 109.0, 39.9, 14.8 ppm.

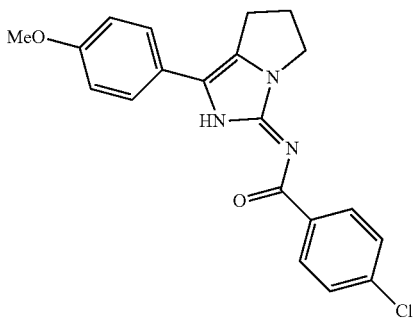

5z

4-Chloro-N-(1-(4-methoxyphenyl)-2,5,6,7-tetrahydro-3H-pyrrolo[1,2-c]imidazol-3-ylidene)benzamide (5z)

Prepared according to general procedure E from 4c (122 mg, 0.68 mmol), iPr$_2$NEt (0.33 mL, 1.86 mmol), chlorotrimethylsilane (0.09 mL, 0.71 mmol), and 3g (150 mg, 0.62 mmol) to yield a white solid (134 mg, 59%). $^1$H NMR (CDCl$_3$, 500 MHz): δ 8.18 (d, J=9.0 Hz, 2H), 7.35 (d, J=9.0 Hz, 2H), 7.33 (d, J=9.0 Hz, 2H), 6.93 (d, J=9.0 Hz, 2H), 4.03 (t, J=7.5 Hz, 2H), 3.04 (t, J=7.5 Hz, 2H), 2.68-2.59 (m, 2H). $^{13}$C NMR (CDCl$_3$, 125 MHz): δ 168.8, 154.0, 142.0, 132.1, 131.9, 125.3, 123.3, 120.6, 120.3, 111.8, 116.9, 109.8, 50.6, 38.6, 23.3, 18.7 ppm. IR (thin film) 1572, 1513, 1338, 1249, 1011, 891, 822, 764 cm$^{-1}$. HRMS (ESI-TOF) m/z: [M+H]+ Calcd for C$_{20}$H$_{19}$N$_3$O$_2$Cl 368.1166; Found 368.1174.

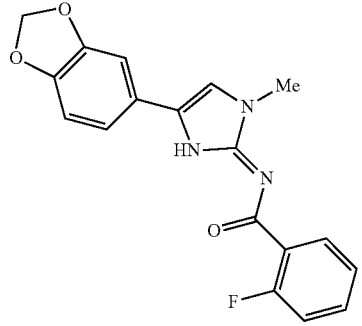

5ab

N-(4-(Benzo[d][1,3]dioxol-5-yl)-1-methyl-1,3-dihydro-2H-imidazol-2-ylidene)-2-fluorobenzamide (5ab)

Prepared according to general procedure E from 4a (79 mg, 0.48 mmol), iPr$_2$NEt (0.32 mL, 1.76 mmol), chlorotrimethylsilane (0.07 mL, 0.51 mmol), and 3h (100 mg, 0.44 mmol) to yield a white solid (98 mg, 66%). $^1$H NMR (CDCl$_3$, 500 MHz): δ 8.10 (t, J=8.0 Hz, 1H), 7.44 (q, J=6.0 Hz, 1H), 7.21 (t, J=7.5 Hz, 1H), 7.12-7.10 (m, 1H), 7.04-7.01 (m, 2H), 6.81-6.79 (m, 2H), 5.96 (s, 2H), 3.61 (s, 3H). LCMS [M+H]+ 340.1. $^{13}$C NMR (125 MHz, CDCl$_3$) δ 164.1, 156.6 (d, J=252.6 Hz), 143.5, 142.5, 128.1, 127.1 (d, J=1.9 Hz), 119.9, 119.3 (d, J=3.5 Hz), 113.3, 111.7 (d, J=23.7 Hz), 107.3, 103.9, 100.3, 96.5, 27.6 ppm. IR (thin film) 2970, 1738, 1558, 1473, 1356, 1230, 1034, 932, 753 cm$^{-1}$. HRMS (ESI-TOF) m/z: [M+H]+ Calcd for C$_{18}$H$_{15}$N$_3$O$_3$F 340.1097; Found 340.1114.

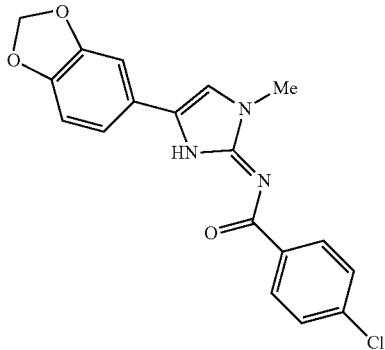

5aa

N-(4-(Benzo[d][1,3]dioxol-5-yl)-1-methyl-1,3-dihydro-2H-imidazol-2-ylidene)-4-chlorobenzamide (5aa)

Prepared according to general procedure E from 4c (87 mg, 0.48 mmol), iPr$_2$NEt (0.32 mL, 1.76 mmol), chlorotrimethylsilane (0.07 mL, 0.51 mmol), and 3h (100 mg, 0.44 mmol) to yield a white solid (108 mg, 69%). $^1$H NMR (CDCl$_3$, 500 MHz): δ 8.19 (d, J=9.0 Hz, 2H), 7.36 (d, J=8.5 Hz, 2H), 6.96 (d, J=8.0 Hz, 2H), 6.92 (s, 2H), 6.83 (d, J=8.0 Hz, 2H), 6.67 (s, 1H), 5.99 (s, 2H), 3.64 (s, 3H). LCMS [M+H]+ 356.1. IR (thin film) 2969, 1738, 1558, 1528, 1345, 1232, 1036, 1012, 938, 900, 806, 756 cm$^{-1}$. HRMS (ESI-TOF) m/z: [M+H]+ Calcd for C$_{18}$H$_{15}$N$_3$O$_3$Cl 356.0802; Found 356.0805.

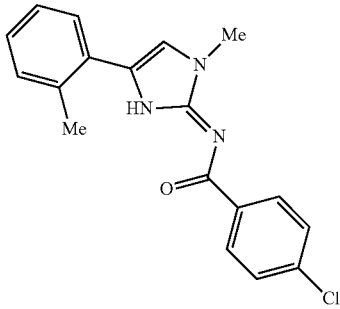

5ac

4-Chloro-N-(1-methyl-4-(o-tolyl)-1,3-dihydro-2H-imidazol-2-ylidene)benzamide (5ac)

Prepared according to general procedure E from 4c (150 mg, 0.83 mmol), iPr$_2$NEt (0.53 mL, 3.0 mmol), chlorotrimethylsilane (0.11 mL, 0.86 mmol), and 3i (150 mg, 0.75 mmol) to yield a white solid (163 mg, 67%). R$_f$=0.46 (EtOAc); $^1$H NMR (CDCl$_3$, 500 MHz): δ 8.27-8.15 (m, 2H), 7.47-7.33 (m, 3H), 7.27-7.19 (m, 3H), 6.61 (s, 1H), 3.65 (s, 3H), 2.44 (s, 3H). $^{13}$C NMR (125 MHz, CDCl$_3$) δ 173.7, 150.6, 136.8, 136.7, 135.2, 131.3, 130.2, 130.2, 128.5, 128.0, 127.9, 127.4, 126.4, 124.4, 113.1, 31.6, 21.3 ppm. IR (thin film): 2948, 1680, 1615, 1589, 1559, 1531, 1481, 1396, 1355, 1291, 1192, 1161, 1085, 1055, 1013, 955, 907, 891 cm$^{-1}$. HRMS (ESI-TOF) m/z: [M+H]+ Calcd for C$_{18}$H$_{17}$N$_3$OC$_1$ 326.1060; Found 326.1076.

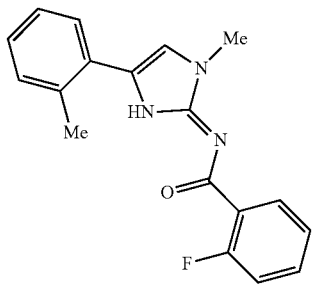

5ad

2-Fluoro-N-(1-methyl-4-(o-tolyl)-1,3-dihydro-2H-imidazol-2-ylidene)benzamide (5ad)

Prepared according to general procedure E from 4a (136 mg, 0.83 mmol), iPr$_2$NEt (0.53 mL, 3.0 mmol), chlorotrimethylsilane (0.11 mL, 0.86 mmol), and 3i (150 mg, 0.75 mmol) to yield a white solid (195 mg, 84%). R$_f$=0.32 (EtOAc). $^1$H NMR (CDCl$_3$, 500 MHz): δ 8.09 (td, J=7.8, 1.8 Hz, 1H), 7.48-7.42 (m, 1H), 7.42-7.30 (m, 1H), 7.25-7.18 (m, 3H), 7.20-7.12 (m, 1H), 7.09 (ddd, J=11.4, 8.3, 1.2 Hz, 1H), 6.69 (s, 1H), 3.61 (s, 3H), 2.43 (s, 3H). IR (thin film): 2951, 1684, 1592, 1540, 1481, 1449, 1358, 1286, 1262, 1217, 1190, 1155, 1124, 1091, 955, 897 cm$^{-1}$.

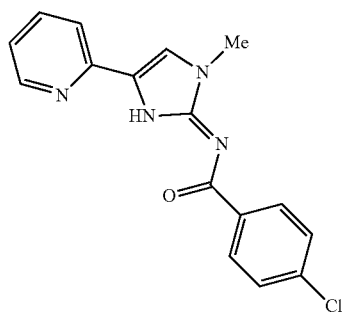

5ae

4-Chloro-N-(1-methyl-4-(pyridin-2-yl)-1,3-dihydro-2H-imidazol-2-ylidene)benzamide (5ae)

Prepared according to general procedure E from 4c (132 mg, 0.72 mmol), iPr$_2$NEt (0.60 mL, 3.6 mmol), chlorotrimethylsilane (0.1 mL, 0.77 mmol), and 3j (150 mg, 0.67 mmol) to yield a brown solid (143.2 mg, 57%). $^1$H NMR (CDCl$_3$, 500 MHz): δ 8.57 (d, J=4.8 Hz, 1H), 8.24 (d, J=8.5 Hz, 2H), 7.68 (td, J=7.7, 1.8 Hz, 1H), 7.43 (t, J=7.9 Hz, 1H), 7.38 (d, J=8.6 Hz, 2H), 7.17 (dd, J=7.5, 4.9 Hz, 1H), 7.07 (s, 1H), 3.67 (s, 3H). $^{13}$C NMR (CDCl$_3$, 125 MHz): δ 173.6, 150.9, 149.8, 146.8, 136.8, 136.7, 136.6, 130.3, 128.1, 125.5, 122.4, 118.2, 113.0, 31.9 ppm. IR (thin film): 1618, 1586, 1571, 1530, 1458, 1360, 1333, 1281, 1253, 1206, 1163, 1087, 1015, 891 cm$^{-1}$. HRMS (ESI-TOF) m/z: [M+H]+ Calcd for C$_{16}$H$_{14}$N$_4$OCl 313.0856; Found 313.0868.

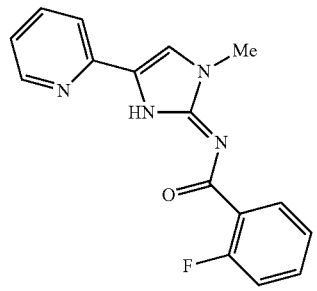

5af

2-Fluoro-N-(1-methyl-4-(pyridin-2-yl)-1,3-dihydro-2H-imidazol-2-ylidene)benzamide (5af)

Prepared according to general procedure E from 4a (120 mg, 0.72 mmol), iPr$_2$NEt (0.60 mL, 3.6 mmol), chlorotrimethylsilane (0.1 mL, 0.77 mmol), and 3j (150 mg, 0.67 mmol) to yield a brown solid (170 mg, 86%). $^1$H NMR (CDCl$_3$, 500 MHz): δ 8.50 (d, J=5.0 Hz, 1H), 8.10 (t, J=8.0 Hz, 1H), 7.65 (t, J=8.0 Hz, 1H), 7.59 (d, J=8.0 Hz, 1H), 7.45 (q, J=6.0 Hz, 1H), 7.28 (s, 1H), 7.21 (t, J=7.5 Hz, 1H), 7.15-7.09 (m, 1H), 3.64 (s, 3H). LCMS [M+H]+ 297.1. $^{13}$C NMR (125 MHz, CDCl$_3$) δ 168.0, 161.2 (d, J$_{CF}$=250.8 Hz) 149.4 (d, J$_{CF}$=7.3 Hz), 136.6 (d, J$_{CF}$=2.8 Hz), 133.1, 132.0, 131.9, 124.2, 123.5, 123.2 122.0, 121.9, 118.5, 116.6, 116.4, 116.0, 32.7 ppm. IR (thin film) 1684, 1593, 1542, 1459, 1357, 1216, 895 cm$^{-1}$. HRMS (ESI-TOF) m/z: [M+H]+ Calcd for C$_{16}$H$_{14}$N$_4$OF 297.1152; Found 297.1156.

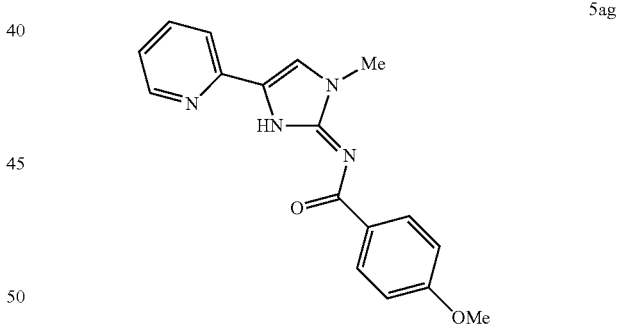

5ag

4-Methoxy-N-(1-methyl-4-(pyridin-2-yl)-1,3-dihydro-2H-imidazol-2-ylidene)benzamide (5ag)

Prepared according to general procedure E from 4b (129 mg, 0.73 mmol), iPr$_2$NEt (0.41 mL, 2.35 mmol), chlorotrimethylsilane (0.1 mL, 0.77 mmol), and 3j (150 mg, 0.67 mmol) to yield a brown solid (147 mg, 71%). $^1$H NMR (CDCl$_3$, 500 MHz): δ 8.47 (d, J=8.5 Hz, 1H), 8.16 (d, J=7.5 Hz, 2H), 7.59 (d, J=7.5 Hz, 1H), 7.43 (d, J=7.5 Hz, 1H), 7.10-7.06 (m, 2H), 6.89 (d, J=8.5 Hz, 1H), 3.83 (s, 3H), 3.60 (s, 3H) ppm. LCMS [M+H]$^+$ 309.2.

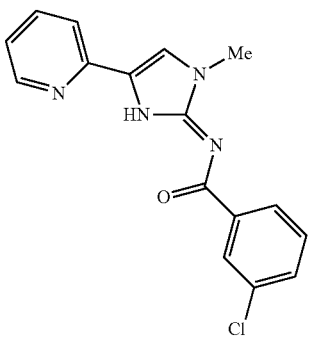

5ah

3-Chloro-N-(1-methyl-4-(pyridin-2-yl)-1,3-dihydro-2H-imidazol-2-ylidene)benzamide (5ah)

Prepared according to general procedure E from 4 g (131 mg, 0.73 mmol), iPr$_2$NEt (0.41 mL, 2.35 mmol), chlorotrimethylsilane (0.1 mL, 0.77 mmol), and 3j (150 mg, 0.67 mmol) to yield a brown solid (204 mg, 95%). $^1$H NMR (CDCl$_3$, 500 MHz): δ 8.53 (d, J=5.0 Hz, 1H), 8.26 (s, 1H), 8.14 (d, J=8.0 Hz, 1H), 7.65 (t, J=7.5 Hz, 1H), 7.40 (d, J=8.5 Hz, 1H), 7.33 (t, J=7.5 Hz, 1H), 7.14 (t, J=6.0 Hz, 1H), 7.04 (s, 1H), 3.66 (s, 3H). LCMS [M+H]$^+$ 313.1.

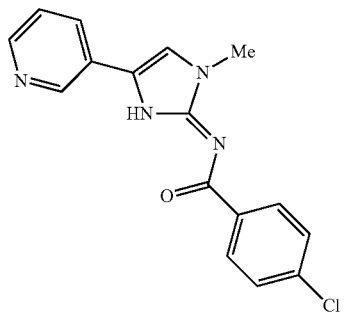

5ai

4-Chloro-N-(1-methyl-4-(pyridin-3-yl)-1,3-dihydro-2H-imidazol-2-ylidene)benzamide (5ai)

Prepared according to general procedure E from 4c (133 mg, 0.73 mmol), iPr$_2$NEt (0.60 mL, 3.35 mmol), chlorotrimethylsilane (0.1 mL, 0.77 mmol), and 3k (150 mg, 0.67 mmol) to yield a brown solid (154 mg, 73%). $^1$H NMR (CDCl$_3$, 500 MHz): δ 8.82 (d, J=2.3 Hz, 1H), 8.58-8.52 (m, 1H), 8.18 (d, J=8.2 Hz, 2H), 7.79 (d, J=8.0 Hz, 1H), 7.39 (d, J=8.5 Hz, 2H), 7.40-7.27 (m, 2H), 6.94 (s, 1H), 3.69 (s, 3H) ppm. LCMS [M+H]$^+$313.2.

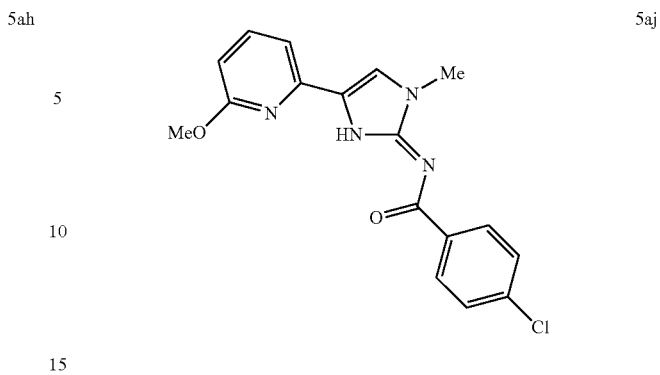

5aj

4-Chloro-N-(4-(6-methoxypyridin-2-yl)-1-methyl-1,3-dihydro-2H-imidazol-2-ylidene)benzamide (5aj)

Prepared according to general procedure E from 4d (59 mg, 0.33 mmol), iPr$_2$NEt (0.18 mL, 1.04 mmol), chlorotrimethylsilane (0.04 mL, 0.34 mmol), and 31 (75 mg, 0.30 mmol) to yield a brown solid (55 mg, 54%). $^1$H NMR (CDCl$_3$, 500 MHz): δ 8.24 (d, J=9.0 Hz, 2H), 7.58 (t, J=7.5 Hz, 1H), 7.37 (d, J=9.0 Hz, 2H), 7.05-7.03 (m, 2H), 6.65 (d, J=8.0 Hz, 1H), 4.05 (s, 3H), 3.69 (s, 3H). LCMS [M+H]$^+$ 343.1.

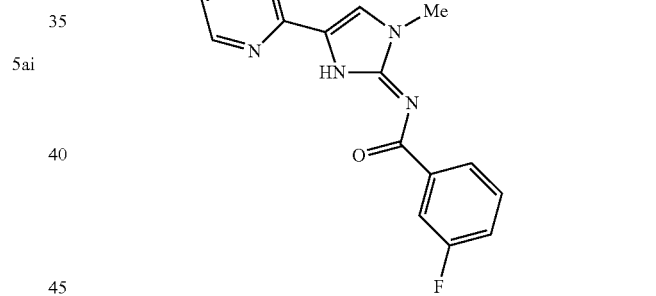

5agx

3-Fluoro-N-(1-methyl-4-(pyridin-2-yl)-1,3-dihydro-2H-imidazol-2-ylidene)benzamide (5agx)

Prepared according to general procedure E from 4i (120 mg, 0.72 mmol), iPr$_2$NEt (0.60 mL, 3.6 mmol), chlorotrimethylsilane (0.1 mL, 0.77 mmol), and 3j (150 mg, 0.67 mmol) to yield a brown solid (122 mg, 62%). $^1$H NMR (500 MHz, CDCl$_3$) δ 8.56 (dd, J=4.8, 1.4 Hz, 1H), 8.34-8.28 (m, 2H), 7.67 (td, J=7.8, 1.6 Hz, 1H), 7.43 (dd, J=8.0, 1.2 Hz, 1H), 7.16 (ddd, J=7.7, 4.9, 1.2 Hz, 1H), 7.12-7.05 (m, 3H), 3.66 (d, J=1.0 Hz, 3H). $^{13}$C NMR (125 MHz, CDCl$_3$) δ 173.4, 164.7 (d, J=249.9 Hz), 150.8, 149.7, 147.0, 136.6, 134.3, 131.0 (d, J=8.9 Hz), 125.6, 122.3, 118.2, 114.8, 113.1, 31.9. IR (thin film) 1559, 1537, 1455, 1361, 1255, 1214, 1200, 1148, 1025, 929, 864 cm$^{-1}$. HRMS (ESI-TOF) m/z: [M+H]+ Calcd for C$_{16}$H$_{14}$N$_4$OF 297.1152; Found 297.1153.

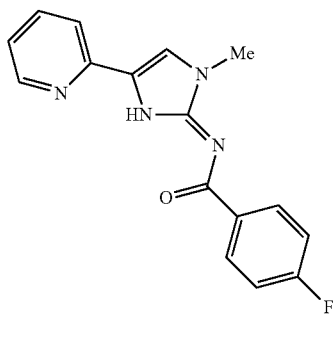

5ahx

4-Fluoro-N-(1-methyl-4-(pyridin-2-yl)-1,3-dihydro-2H-imidazol-2-ylidene)benzamide (5ahx)

Prepared according to general procedure E from 4e (120 mg, 0.72 mmol), iPr$_2$NEt (0.60 mL, 3.6 mmol), chlorotrimethylsilane (0.1 mL, 0.77 mmol), and 3j (150 mg, 0.67 mmol) to yield a brown solid (134 mg, 68%). $^1$H NMR (500 MHz, CDCl$_3$) δ 8.58-8.52 (m, 1H), 8.08 (d, J=7.7 Hz, 1H), 8.02-7.95 (m, 1H), 7.65 (td, J=7.8, 1.8 Hz, 1H), 7.43-7.34 (m, 2H), 7.15 (dt, J=9.0, 4.7 Hz, 2H), 7.04 (s, 1H), 3.65 (s, 3H). $^{13}$C NMR (125 MHz, CDCl$_3$) δ 173.2, 162.7 (d, J=244.4 Hz), 149.7, 146.7, 140.8, 136.6, 129.3 (d, J=7.7 Hz), 124.4 (d, J=2.7 Hz), 122.4, 118.2, 117.5 (d, J=21.4 Hz), 115.6 (d, J=22.3 Hz), 113.0, 31.9. IR (thin film): 1618, 1593, 1580, 1534, 1504, 1360, 1229, 1208, 1146 cm$^{-1}$. HRMS (ESI-TOF) m/z: [M+H]+ Calcd for C$_{16}$H$_{14}$N$_4$OF 297.1152; Found 297.1160.

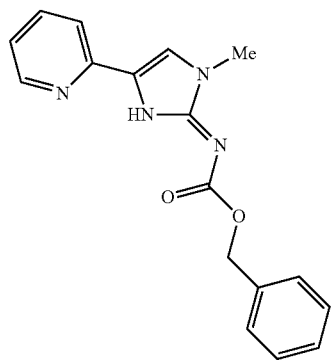

5ajx

Benzyl (1-methyl-4-(pyridin-2-yl)-1,3-dihydro-2H-imidazol-2-ylidene)carbamate (5ajx)

Prepared according to general procedure E from potassium benzyloxycarbonylcyanamide (528 mg, 2.46 mmol), iPr$_2$NEt (1.20 mL, 6.72 mmol), chlorotrimethylsilane (330 μL, 2.58 mmol), and 3j (500 mg, 2.24 mmol) to yield a white solid (265 mg, 38%). $^1$H NMR (500 MHz, CDCl$_3$) δ 8.50 (dd, J=4.7, 1.7 Hz, 1H), 7.60-7.52 (m, 2H), 7.42 (d, J=7.9 Hz, 2H), 7.35-7.27 (m, 3H), 7.14-7.06 (m, 2H), 5.21 (s, 2H), 3.51 (s, 3H). $^{13}$C NMR (126 MHz, CDCl$_3$) δ 149.4, 136.9, 136.5, 128.4, 128.1, 127.9, 122.0, 118.4, 114.9, 67.1, 32.4. IR (thin film) 1726, 1622, 1573, 1456, 1380, 1295, 1221, 1085, 1062, 1028, 992, 909 cm$^{-1}$. HRMS (ESI-TOF) m/z: [M+H]+ Calcd for C$_{17}$H$_{17}$N$_4$O$_2$ 309.1352; Found 309.1369.

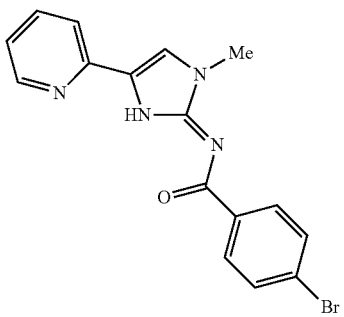

5aix

4-Bromo-N-(1-methyl-4-(pyridin-2-yl)-1,3-dihydro-2H-imidazol-2-ylidene)benzamide (5aix)

Prepared according to general procedure E from 4j (164 mg, 0.72 mmol), iPr$_2$NEt (0.60 mL, 3.6 mmol), chlorotrimethylsilane (0.1 mL, 0.77 mmol), and 3j (150 mg, 0.67 mmol) to yield a white solid (154 mg, 64%). R$_f$=0.33 (EtOAc). $^1$H NMR (500 MHz, CDCl$_3$) δ 8.57 (d, J=4.8 Hz, 1H), 8.21-8.15 (m, 2H), 7.72-7.65 (m, 1H), 7.58-7.52 (m, 2H), 7.43 (d, J=7.9 Hz, 1H), 7.21-7.16 (m, 1H), 7.06 (s, 1H), 3.67 (s, 3H). $^{13}$C NMR (125 MHz, CDCl$_3$) δ 173.6, 150.9, 149.8, 146.8, 137.2, 136.6, 131.0, 130.5, 125.5, 122.4, 118.2, 113.0, 110.8, 31.9. IR (thin film): 1617, 1597, 1567, 1527, 1458, 1362, 1332, 1205 cm$^{-1}$. HRMS (ESI-TOF) m/z: [M+H]+ Calcd for C$_{16}$H$_{14}$N$_4$OBr 357.0351; Found 357.0367.

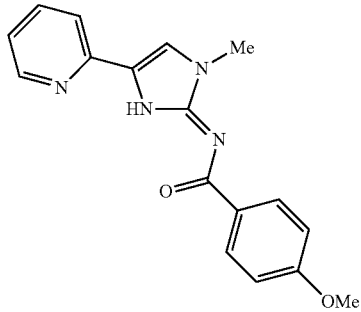

5akx

4-Methoxy-N-(1-methyl-4-(pyridin-2-yl)-1,3-dihydro-2H-imidazol-2-ylidene)benzamide (5akx)

Prepared according to general procedure E from 4b (129 mg, 0.73 mmol), iPr$_2$NEt (0.41 mL, 2.35 mmol), chlorotrimethylsilane (0.1 mL, 0.77 mmol), and 3j (150 mg, 0.67 mmol) to yield a brown solid (147 mg, 71%). $^1$H NMR (CDCl$_3$, 500 MHz): δ 8.47 (d, J=8.5 Hz, 1H), 8.16 (d, J=7.5 Hz, 2H), 7.59 (d, J=7.5 Hz, 1H), 7.43 (d, J=7.5 Hz, 1H), 7.10-7.06 (m, 2H), 6.89 (d, J=8.5 Hz, 1H), 3.83 (s, 3H), 3.60 (s, 3H) ppm. $^{13}$C NMR (125 MHz, CDCl$_3$) δ 171.9, 162.2, 149.5, 148.6, 136.5, 130.8, 130.4, 130.2, 121.9, 118.3, 114.7, 113.3, 112.9, 112.9, 55.3, 32.3 ppm. IR (thin film) 1557, 1524, 1458, 1336, 1325, 1246, 1251, 1158, 1025, 891 cm$^{-1}$. HRMS (ESI-TOF) m/z: [M+H]+ Calcd for C$_{17}$H$_{17}$N$_4$O$_2$ 309.1352; Found 309.1357.

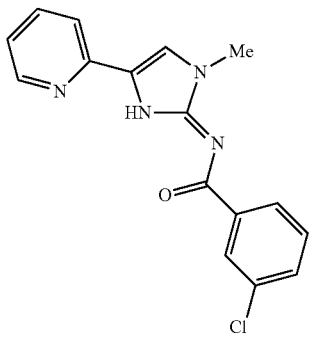

3-Chloro-N-(1-methyl-4-(pyridin-2-yl)-1,3-dihydro-2H-imidazol-2-ylidene)benzamide (5al)

Prepared according to general procedure E from 4 g (131 mg, 0.73 mmol), iPr$_2$NEt (0.41 mL, 2.35 mmol), chlorotrimethylsilane (0.1 mL, 0.77 mmol), and 3j (150 mg, 0.67 mmol) to yield a brown solid (204 mg, 95%). R$_f$=0.24 (EtOAc). $^1$H NMR (CDCl$_3$, 500 MHz): δ 8.53 (d, J=5.0 Hz, 1H), 8.26 (s, 1H), 8.14 (d, J=8.0 Hz, 1H), 7.65 (t, J=7.5 Hz, 1H), 7.40 (d, J=8.5 Hz, 1H), 7.33 (t, J=7.5 Hz, 1H), 7.14 (t, J=6.0 Hz, 1H), 7.04 (s, 1H), 3.66 (s, 3H). $^{13}$C NMR (125 MHz, CDCl$_3$) δ 172.9, 149.8, 146.9, 140.0, 136.6, 133.9, 130.7, 129.2, 129.0, 126.9, 122.4, 118.2, 113.1, 32.0 ppm. IR (thin film) 1560, 1539, 1456, 1364, 1326, 1243, 1205, 1149, 1053, 1024, 902 cm$^{-1}$. HRMS (ESI-TOF) m/z: [M+H]+ Calcd for C$_{16}$H$_{14}$N$_4$OC$_1$ 313.0856; Found 313.0864.

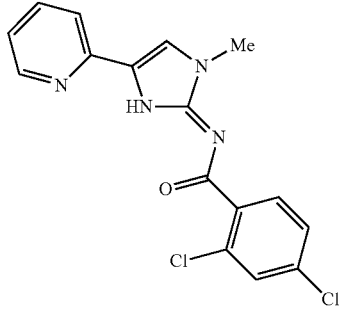

2,4-Dichloro-N-(1-methyl-4-(pyridin-2-yl)-1,3-dihydro-2H-imidazol-2-ylidene)benzamide (5an)

Prepared according to general procedure E from 4f (157 mg, 0.73 mmol), iPr$_2$NEt (0.41 mL, 2.35 mmol), chlorotrimethylsilane (0.1 mL, 0.77 mmol), and 3j (150 mg, 0.67 mmol) to yield a brown solid (183 mg, 79%). $^1$H NMR (500 MHz, CDCl$_3$) δ 8.52 (d, J=4.9 Hz, 1H), 7.88-7.82 (m, 1H), 7.64 (t, J=7.7 Hz, 1H), 7.46-7.37 (m, 2H), 7.22 (dd, J=8.4, 2.1 Hz, 1H), 7.17-7.08 (m, 2H), 3.60 (s, 3H). $^{13}$C NMR (125 MHz, CDCl$_3$) δ 168.9, 145.7, 145.0, 143.3, 132.6, 132.5, 131.5, 129.2, 127.9, 126.2, 122.7, 118.4, 114.4, 109.8, 28.3. IR (thin film): 1690, 1618, 1548, 1458, 1352, 1209, 1140, 1100, 1046, 992, 894 cm$^{-1}$. HRMS (ESI-TOF) m/z: [M+H]+ Calcd for C$_{16}$H$_{13}$N$_4$OCl$_2$ 347.0466; Found 347.0471.

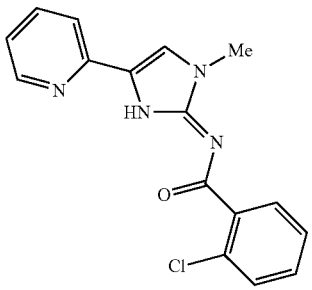

2-Chloro-N-(1-methyl-4-(pyridin-2-yl)-1,3-dihydro-2H-imidazol-2-ylidene)benzamide (5am)

Prepared according to general procedure E from 4h (131 mg, 0.73 mmol), iPr$_2$NEt (0.41 mL, 2.35 mmol), chlorotrimethylsilane (0.1 mL, 0.77 mmol), and 3j (150 mg, 0.67 mmol) to yield a brown solid (172 mg, 85%). R$_f$=0.23 (EtOAc). R$_f$=0.23 (EtOAc). $^1$H NMR (500 MHz, CDCl$_3$) δ 8.58 (s, 1H), 8.31 (s, 1H), 8.18 (d, J=7.5 Hz, 1H), 7.70 (t, J=7.5 Hz, 1H), 7.49-7.41 (m, 2kH), 7.41-7.34 (m, 1H), 7.19 (d, J=6.4 Hz, 1H), 7.09 (s, 1H), 3.70 (s, 3H). $^{13}$C NMR (125 MHz, CDCl$_3$) δ 173.3, 151.0, 149.8, 148.2, 146.7, 140.2, 136.6, 133.9, 130.6, 129.2, 129.0, 126.9, 122.4, 118.2, 112.9, 32.0. IR (thin film) 1560, 1523, 1501, 1452, 1369, 1330, 1240, 1207, 1149, 1066, 984, 901 cm$^{-1}$. HRMS (ESI-TOF) m/z: [M+H]+ Calcd for C$_{16}$H$_{14}$N$_4$OC$_1$ 313.0856; Found 313.0859.

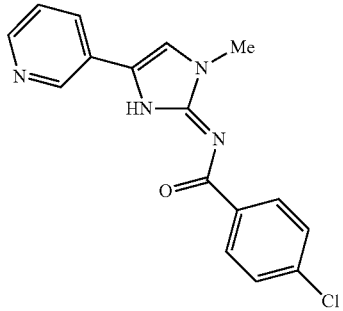

4-Chloro-N-(1-methyl-4-(pyridin-3-yl)-1,3-dihydro-2H-imidazol-2-ylidene)benzamide (5ao)

Prepared according to general procedure E from 4c (133 mg, 0.73 mmol), iPr$_2$NEt (0.60 mL, 3.35 mmol), chlorotrimethylsilane (0.1 mL, 0.77 mmol), and 3k (150 mg, 0.67 mmol) to yield a brown solid (154 mg, 73%). $^1$H NMR (CDCl$_3$, 500 MHz): δ 8.82 (d, J=2.3 Hz, 1H), 8.58-8.52 (m, 1H), 8.18 (d, J=8.2 Hz, 2H), 7.79 (d, J=8.0, 1H), 7.39 (d, J=8.5 Hz, 2H), 7.40-7.27 (m, 2H), 6.94 (s, 1H), 3.69 (s, 3H) ppm. IR (thin film) 1675, 1566, 1456, 1272, 1194, 1088, 947, 849, 819 cm$^{-1}$. HRMS (ESI-TOF) m/z: [M+H]+ Calcd for C$_{16}$H$_{14}$N$_4$OC$_1$ 313.0856; Found 313.0862.

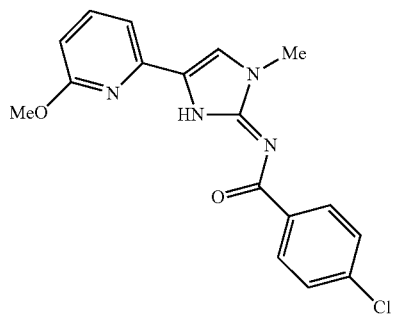

5ap

4-Chloro-N-(4-(6-methoxypyridin-2-yl)-1-methyl-1,3-dihydro-2H-imidazol-2-ylidene)benzamide (5ap)

Prepared according to general procedure E from 4d (59 mg, 0.33 mmol), iPr$_2$NEt (0.18 mL, 1.04 mmol), chlorotrimethylsilane (0.04 mL, 0.34 mmol), and 31 (75 mg, 0.30 mmol) to yield a brown solid (55 mg, 54%). R$_f$=0.46 (6:4 hexanes/EtOAc). $^1$H NMR (CDCl$_3$, 500 MHz): δ 8.24 (d, J=9.0 Hz, 2H), 7.58 (t, J=7.5 Hz, 1H), 7.37 (d, J=9.0 Hz, 2H), 7.05-7.03 (m, 2H), 6.65 (d, J=8.0 Hz, 1H), 4.05 (s, 3H), 3.69 (s, 3H). $^{13}$C NMR (125 MHz, CDCl$_3$) δ 173.8, 163.9, 150.7, 144.2, 139.1, 136.8, 130.3, 128.1, 125.2, 112.7, 110.9, 110.0, 53.6, 31.9 ppm. IR (thin film) 1589, 1558, 1467, 1353, 1325, 1290, 1086, 1013 cm$^{-1}$. HRMS (ESI-TOF) m/z: [M+H]+ Calcd for C$_{17}$H$_{16}$N$_4$O$_2$Cl 343.0962; Found 343.0971.

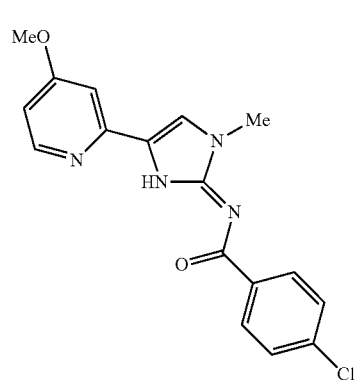

5aq

4-Chloro-N-(4-(4-methoxypyridin-2-yl)-1-methyl-1,3-dihydro-2H-imidazol-2-ylidene)benzamide (5aq)

Prepared according to general procedure E from 4c (118 mg, 0.65 mmol), iPr$_2$NEt (362 μL, 2.10 mmol), chlorotrimethylsilane (86 μL, 0.68 mmol), and 3m (150 mg, 0.59 mmol) to yield a brown solid (152 mg, 75%). R$_f$=0.38 (EtOAc). $^1$H NMR (500 MHz, CDCl$_3$) δ 10.16 (s, 1H), 8.37 (d, J=5.7 Hz, 1H), 7.84-7.74 (m, 2H), 7.64 (s, 1H), 7.30-7.20 (m, 3H), 6.65 (dd, J=5.7, 2.5 Hz, 1H), 4.12 (s, 3H), 3.79 (s, 3H). $^{13}$C NMR (125 MHz, CDCl$_3$) δ 163.2, 161.2, 148.7, 147.0, 138.3, 135.3, 134.5, 129.7, 126.3, 126.0, 110.4, 107.3, 104.8, 52.5, 33.6. IR (thin film): 1663, 1594, 1562, 1487, 1454, 1410, 1307, 1272, 1033 cm$^{-1}$.

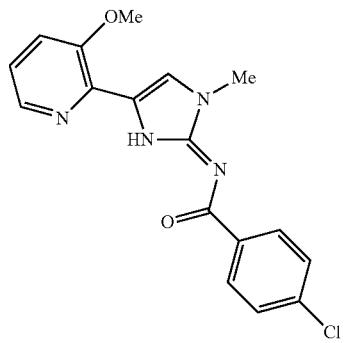

5ar

4-Chloro-N-(4-(3-methoxypyridin-2-yl)-1-methyl-1,3-dihydro-2H-imidazol-2-ylidene)benzamide (5ar)

Prepared according to general procedure E from 4c (118 mg, 0.65 mmol), iPr$_2$NEt (362 μL, 2.10 mmol), chlorotrimethylsilane (86 μL, 0.68 mmol), and 3n (150 mg, 0.59 mmol) to yield a brown solid (115 mg, 57%). R$_f$=0.29 (EtOAc). $^1$H NMR (500 MHz, CDCl$_3$) δ 8.26 (dd, J=8.5, 1.0 Hz, 2H), 8.20 (d, J=4.5 Hz, 1H), 7.37 (d, J=8.5 Hz, 2H), 7.23-7.19 (m, 2H), 7.18-7.13 (m, 1H), 3.97 (s, 3H), 3.65 (s, 3H). $^{13}$C NMR (125 MHz, CDCl$_3$) δ 171.0, 149.6, 147.6, 138.6, 134.6, 134.0, 133.6, 127.7, 127.6, 125.4, 119.9, 119.7, 114.9, 113.4, 52.9, 29.2. IR (thin film): 1612, 1590, 1565, 1534, 1468, 1369, 1354, 1278, 1222, 1013 cm$^{-1}$.

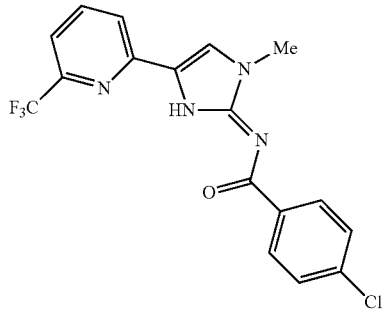

5as

4-Chloro-N-(1-methyl-4-(6-(trifluoromethyl)pyridin-2-yl)-1,3-dihydro-2H-imidazol-2-ylidene)benzamide (5as)

Prepared according to general procedure E from 4c (68 mg, 0.38 mmol), iPr$_2$NEt (211 μL, 1.20 mmol), chlorotrimethylsilane (50 μL, 0.39 mmol), and 3o (100 mg, 0.34 mmol) to yield a white solid (87 mg, 67%). R$_f$=0.62 (EtOAc). $^1$H NMR (500 MHz, CDCl$_3$) δ 8.21 (d, J=8.0 Hz, 2H), 7.85 (t, J=8.0 Hz, 1H), 7.62 (d, J=7.9 Hz, 1H), 7.53 (d, J=7.7 Hz, 1H), 7.39 (d, J=8.1 Hz, 2H), 7.23 (s, 1H), 3.68 (s, 2H). $^{13}$C NMR (125 MHz, CDCl$_3$) δ 172.9, 148.3 (q, J=35.0 Hz), 148.0, 138.1, 137.3, 135.7, 130.2, 128.2, 121.2 (q, J=274.3 Hz) 120.7, 118.6, 118.5, 115.4, 32.2. IR (thin film) 1561, 1532, 1368, 1332, 1159, 1130, 1110, 1087, 1041, 1013, 806, 767 cm$^{-1}$. HRMS (ESI-TOF) m/z: [M+H]+ Calcd for C$_{17}$H$_{13}$N$_4$OF$_3$Cl 381.0730; Found 381.0741.

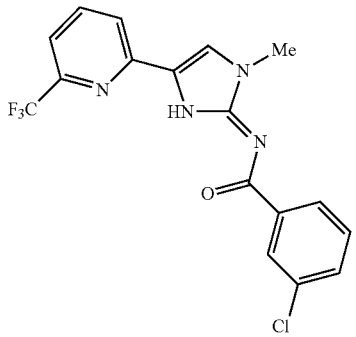

3-Chloro-N-(1-methyl-4-(6-(trifluoromethyl)pyridin-2-yl)-1,3-dihydro-2H-imidazol-2-ylidene)benzamide (5at)

Prepared according to general procedure E from 4 g (68 mg, 0.37 mmol), iPr$_2$NEt (0.18 mL, 1.03 mmol), chlorotrimethylsilane (0.05 mL, 0.40 mmol), and 3o (100 mg, 0.34 mmol) to yield a white solid (77 mg, 59%). R$_f$=0.23 (6:4 hexanes/EtOAc). $^1$H NMR (500 MHz, CDCl$_3$) δ 8.22 (t, J=2.1 Hz, 1H), 8.12 (d, J=7.7 Hz, 1H), 7.80 (t, J=7.7 Hz, 1H), 7.54 (d, J=8.1 Hz, 1H), 7.50 (dd, J=7.7, 2.1 Hz, 1H), 7.41 (d, J=7.3 Hz, 1H), 7.38-7.31 (m, 1H), 7.14 (s, 1H), 3.64 (s, 2H). $^{13}$C NMR (126 MHz, CDCl$_3$) δ 172.7, 148.2 (q, J=35.1 Hz), 147.8, 139.4, 138.0, 134.0, 130.9, 129.3, 129.0, 126.8, 121.2 (q, J=274.3 Hz), 120.8, 118.6 (d, J=2.9 Hz), 115.2, 32.1. IR (thin film) 1541, 1359, 1333, 1128, 1110, 778 cm$^{-1}$. HRMS (ESI-TOF) m/z: [M+H]+ Calcd for C$_{17}$H$_{13}$N$_4$OF$_3$Cl 381.0730; Found 381.0739.

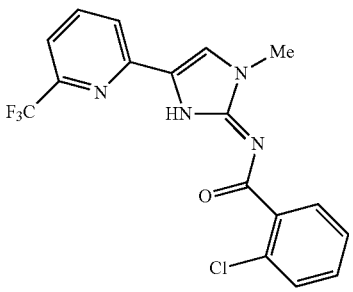

2-Chloro-N-(1-methyl-4-(6-(trifluoromethyl)pyridin-2-yl)-1,3-dihydro-2H-imidazol-2-ylidene)benzamide (5au)

Prepared according to general procedure E from 4c (68 mg, 0.37 mmol), iPr$_2$NEt (0.18 mL, 1.03 mmol), chlorotrimethylsilane (0.05 mL, 0.40 mmol), and 3o (100 mg, 0.34 mmol) to yield a white solid (19 mg, 14%). R$_f$=0.60 (EtOAc). $^1$H NMR (500 MHz, CDCl$_3$) δ 7.83-7.80 (m, 2H), 7.69-7.68 (m, 1H), 7.52-7.41 (m, 3H), 7.38-7.29 (m, 2H), 3.71 (s, 3H). $^{13}$C NMR (126 MHz, CDCl$_3$) δ 165.1, 145.9, 143.3 (q, J=34.6 Hz), 133.2, 131.0, 126.7, 126.5, 125.6, 125.5, 122.1, 116.6 (q, J=274.3 Hz), 116.1, 113.4, 28.5. IR (thin film) 1692, 1602, 1561, 1471, 1341, 1306, 1257, 1185, 1137, 1115 cm$^{-1}$.

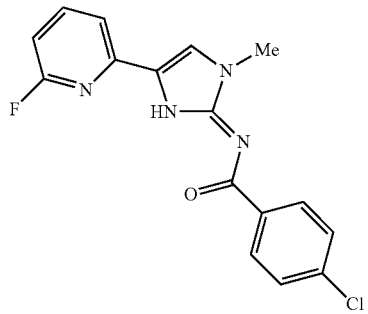

4-Chloro-N-(4-(6-fluoropyridin-2-yl)-1-methyl-1,3-dihydro-2H-imidazol-2-ylidene)benzamide (5av)

Prepared according to general procedure E from 4c (370 mg, 2.05 mmol), iPr$_2$NEt (1.07 mL, 5.98 mmol), chlorotrimethylsilane (270 µL, 2.14 mmol), and 3p (350 mg, 1.71 mmol) to yield a white solid (372 mg, 66%). R$_f$=0.60 (EtOAc). $^1$H NMR (500 MHz, CDCl$_3$) δ 8.23 (d, J=8.1 Hz, 2H), 7.81 (q, J=7.8 Hz, 1H), 7.41 (d, J=8.4 Hz, 2H), 7.38-7.33 (m, 1H), 7.19 (s, 1H), 6.82 (dd, J=8.1, 2.7 Hz, 1H), 3.70 (s, 3H). $^{13}$C NMR (125 MHz, CDCl$_3$) δ 166.2, 163.1 (d, J=235.0 Hz), 152.2 (d, J=14.1 Hz), 143.1, 140.1, 137.8, 136.7, 131.8, 130.3, 129.2, 121.0, 115.9, 106.9 (d, J=37.3 Hz), 33.2.

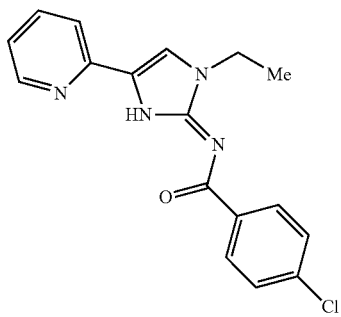

4-Chloro-N-(1-ethyl-4-(pyridin-2-yl)-1,3-dihydro-2H-imidazol-2-ylidene)benzamide (5aw)

Prepared according to general procedure E from 4c (126 mg, 0.70 mmol), iPr$_2$NEt (392 µL, 2.20 mmol), chlorotrimethylsilane (92 µL, 0.72 mmol), and 3q (150 mg, 0.63 mmol) to yield a white solid (159 mg, 77%). $^1$H NMR (500 MHz, CDCl$_3$) δ 8.61-8.57 (m, 1H), 8.25 (d, J=8.5 Hz, 2H), 7.70 (td, J=7.7, 1.8 Hz, 1H), 7.49-7.45 (m, 1H), 7.42-7.37 (m, 2H), 7.19 (ddd, J=7.5, 4.8, 1.0 Hz, 1H), 7.13 (s, 1H), 4.14 (q, J=7.3 Hz, 2H), 1.50 (t, J=7.3 Hz, 3H). $^{13}$C NMR (125 MHz, CDCl$_3$) δ 171.1, 147.3, 144.3, 134.3, 134.2, 134.1, 127.7, 126.3, 125.5, 122.8, 119.8, 115.6, 108.7, 37.5, 12.2. IR (thin film): 1615, 1591, 1567, 1560, 1459, 1397, 1378, 1338, 1088 cm$^{-1}$.

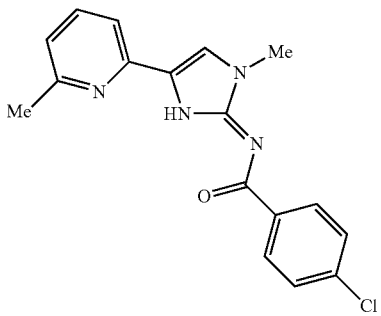

5ax

4-Chloro-N-(1-methyl-4-(6-methylpyridin-2-yl)-1,3-dihydro-2H-imidazol-2-ylidene)benzamide (5ax)

Prepared according to general procedure E from 4c (108 mg, 0.60 mmol), iPr$_2$NEt (311 µL, 1.75 mmol), chlorotrimethylsilane (79 µL, 0.63 mmol), and 3r (100 mg, 0.50 mmol) to yield a white solid (47 mg, 27%). $^1$H NMR (500 MHz, CDCl$_3$) δ 8.24 (d, J=8.1 Hz, 2H), 7.52 (t, J=7.5 Hz, 1H), 7.38 (d, J=8.1 Hz, 2H), 7.17 (d, J=7.5 Hz, 1H), 7.00 (d, J=7.5 Hz, 1H), 6.94 (s, 1H), 3.61 (s, 3H), 2.54 (s, 3H). $^{13}$C NMR (125 MHz, CDCl$_3$) δ 168.6, 154.0, 141.3, 132.0, 132.0, 125.5, 125.4, 123.3, 123.2, 120.6, 117.2, 110.6, 107.9, 27.1, 19.7.

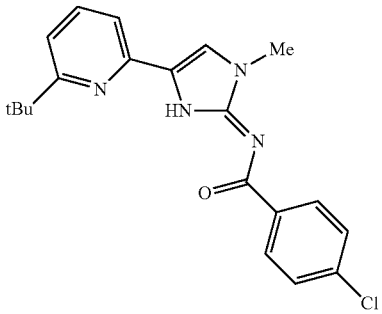

5ay

N-(4-(6-(tert-Butyl)pyridin-2-yl)-1-methyl-1,3-dihydro-2H-imidazol-2-ylidene)-4-chlorobenzamide (5ay)

Prepared according to general procedure E from 4c (90 mg, 0.50 mmol), iPr$_2$NEt (255 µL, 1.42 mmol), chlorotrimethylsilane (65 µL, 0.51 mmol), and 3s (100 mg, 0.41 mmol) to yield a white solid (43 mg, 27%). $^1$H NMR (500 MHz, CDCl$_3$) δ 8.26 (d, J=8.2 Hz, 2H), 7.62 (t, J=7.8 Hz, 1H), 7.38 (d, J=8.3 Hz, 2H), 7.24 (d, J=7.8 Hz, 2H), 7.02 (s, 1H), 3.67 (s, 3H), 1.42 (s, 9H). $^{13}$C NMR (125 MHz, CDCl$_3$) δ 168.9, 164.8, 146.0, 140.4, 132.1, 132.0, 126.0, 125.6, 123.3, 121.0, 113.2, 110.4, 107.7, 32.9, 27.2, 25.4.

All publications, including patents and patent applications, in this application are incorporated herein by reference in their entirety, except insofar as they expressly contradict the present application (e.g., two contradictory definitions of the same term). This includes U.S. application Ser. No. 15/268,410 (filed Sep. 16, 2016), International Application No. PCT/US2015/021602 (filed Mar. 19, 2015), and U.S. Provisional Application Nos. 61/955,761 (filed Mar. 19, 2014) and 62/051,863 (filed Sep. 17, 2014).

What is claimed is:

1. A composition for therapeutic use, the composition comprising a 2-(acylamino)imidazole compound of structure I:

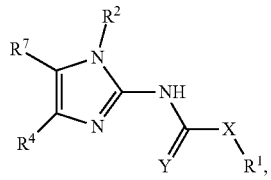

I or a salt, or a tautomer thereof;
wherein:
R$^1$ is haloaryl;
X is a bond;
Y is O;
R$^2$ is a member independently selected from the group consisting of alkyl, alkenyl, alkynyl, and arylalkyl; or, alternatively, R$^2$ and R$^7$ join to form an additional heterocyclyl fused ring;
R$^4$ is selected from the group consisting of:

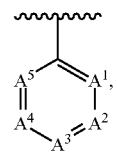

wherein A$^1$, A$^2$, A$^3$, A$^4$, and A$^5$ are each independently selected CH or CR$^{6n}$; and one, two, or three of A$^1$, A$^2$, A$^3$, A$^4$, and A$^5$ are optionally N;

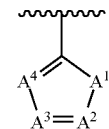

wherein A$^1$ is NH; A$^2$, A$^3$, and A$^4$ are each independently selected CH or CR$^{6n}$; and one, two, or three of A$^2$, A$^3$, and A$^4$ are optionally N;

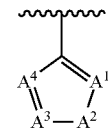

wherein A$^2$ is NH; A$^1$, A$^3$, and A$^4$ are each independently selected CH or CR$^{6n}$; and one, two, or three of A$^1$, A$^3$, and A$^4$ are optionally N;

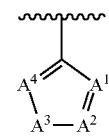

wherein A$^3$ is NH; A$^1$, A$^2$, and A$^4$ are each independently selected CH or CR$^{6n}$; and one, two, or three of A$^1$, A$^2$, and A$^4$ are optionally N;

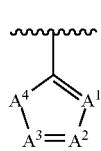

wherein $A^4$ is NH; $A^1$, $A^2$, and $A^3$ are each independently selected CH or $CR^{6n}$; and one, two, or three of $A^1$, $A^2$, and $A^3$ are optionally N;

each of the $R^{6n}$ members is independently selected from the group consisting of alkyl, hydroxy, alkoxy, aminoalkoxy, alkylamino, alkylaminoalkoxy, alkenyl, alkynyl, aryl, aryloxy, arylamino, cycloalkyl, cycloalkylalkyl, cycloalkoxy, cycloalkylalkoxy, cycloalkylamino, cycloalkylalkylamino, heterocyclyl, heterocycyloxy, heterocycylalkyloxy, heterocycylamino, heterocycylalkylamino, halo, haloalkyl, fluoroalkyloxy, arylalkyl, arylalkyloxy, arylalkylamino, heteroaryl, heteroaryloxy, heteroarylamino, heteroarylalkyl, heteroarylalkyloxy, and heteroarylalkylamino; or, alternatively, a pair of adjacent $R^{6n}$ members join to form an additional fused ring that is selected from the group consisting of cycloalkyl, aryl, heterocyclyl, and heterocycloaryl; and $R^7$ is a member independently selected from the group consisting of hydrogen, halo, methyl, trifluoromethyl, ethyl, and isopropyl; or, alternatively, $R^2$ and $R^7$ join to form an additional heterocyclyl fused ring;

wherein the composition has <2% (w/w) of $N^2,N^2$-diacylation; and wherein the composition has <2% (w/w) of acyl regioisomers.

2. The composition of claim 1, wherein the 2-aminoimidazole compound has <1% (w/w) of an impurity selected from the group consisting of

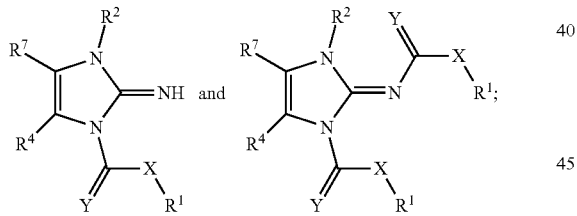

or a salt thereof.

3. The composition of claim 1, wherein $R^1$ is a member selected from the group consisting of 2-chlorophenyl, 3-chlorophenyl, 4-chlorophenyl, 2,4-dichlorophenyl, 2-fluorophenyl, 3-fluorophenyl, and 4-fluorophenyl.

4. The composition of claim 1, wherein $R^1$ is 4-chlorophenyl.

5. The composition of claim 1, wherein $R^2$ is a member selected from the group consisting of alkyl, alkenyl, and arylalkyl.

6. The composition of claim 1, wherein $R^2$ is methyl or ethyl.

7. The composition of claim 1, wherein each of the $R^{6n}$ members is independently selected from the group consisting of alkyl, hydroxy, alkoxy, cycloalkylalkoxy, halo, fluoroalkyl, fluoroalkyloxy, and arylalkyloxy.

8. The composition of claim 1, wherein each of the $R^{6n}$ members is independently selected from the group consisting of alkyl, hydroxy, and alkoxy.

9. The composition of claim 1, wherein $R^7$ is methyl, isopropyl, or hydrogen.

10. The composition of claim 1, wherein $R^7$ is hydrogen.

11. The composition of claim 1, the composition comprising a compound that is selected from the group consisting of

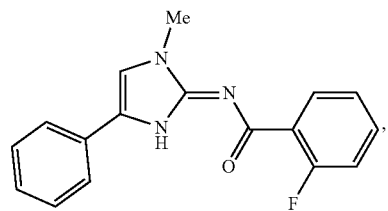

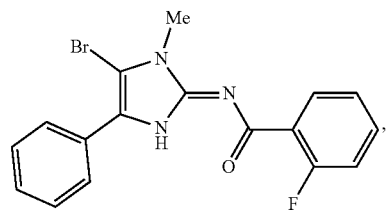

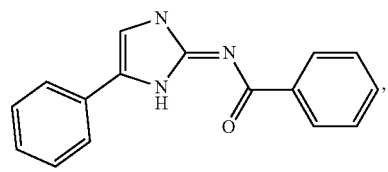

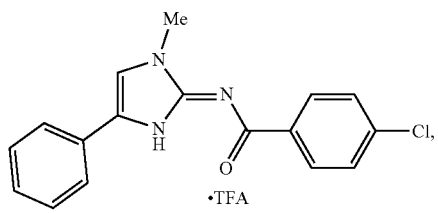

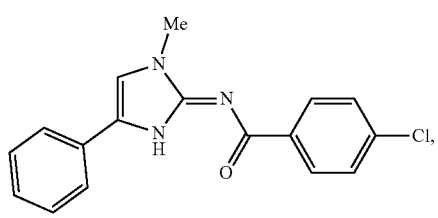

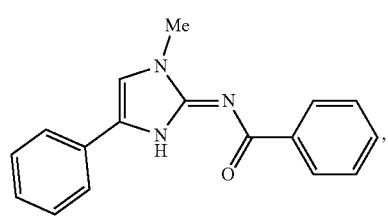

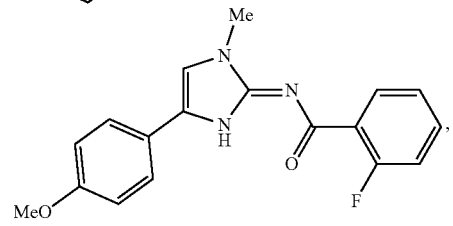

-continued
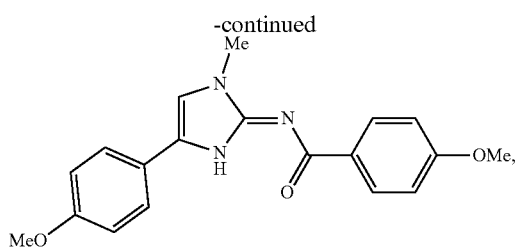
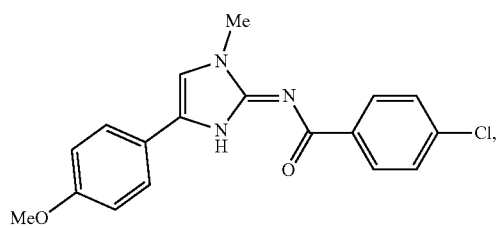
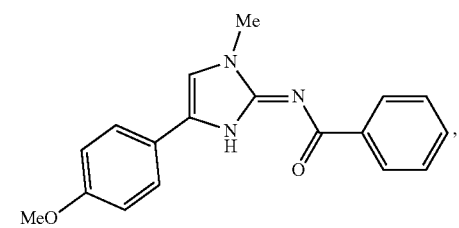
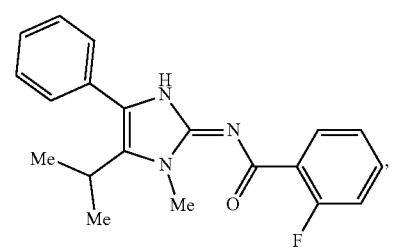
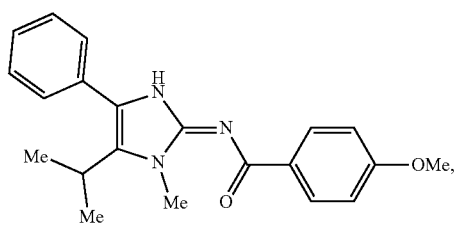
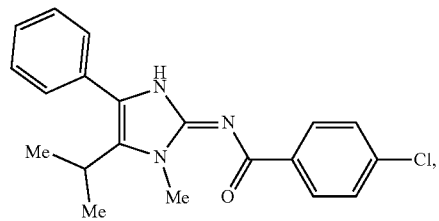
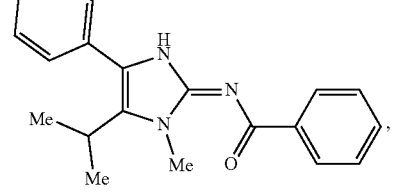
-continued
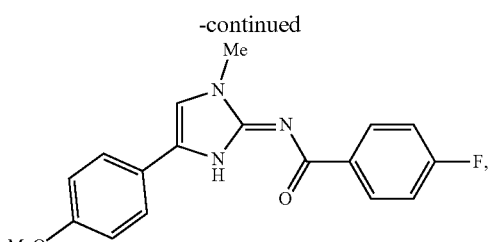
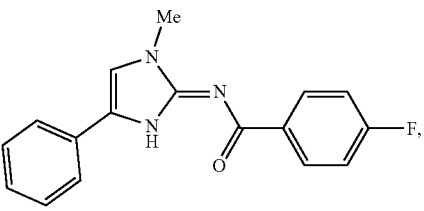
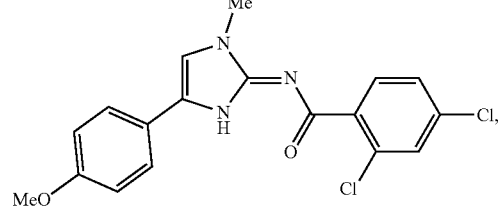
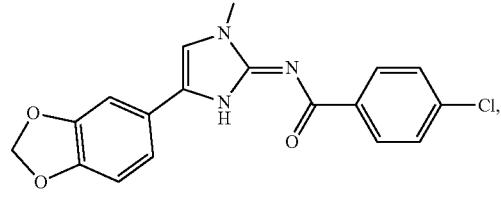
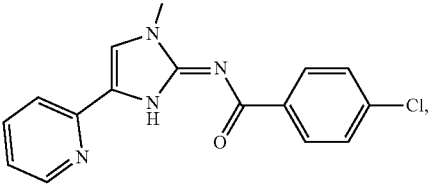
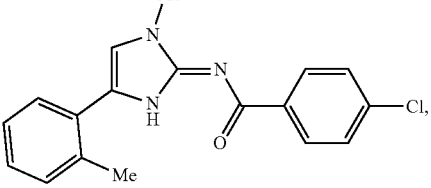
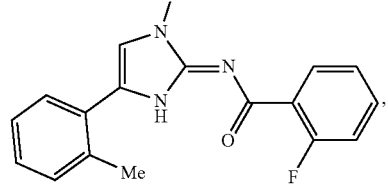

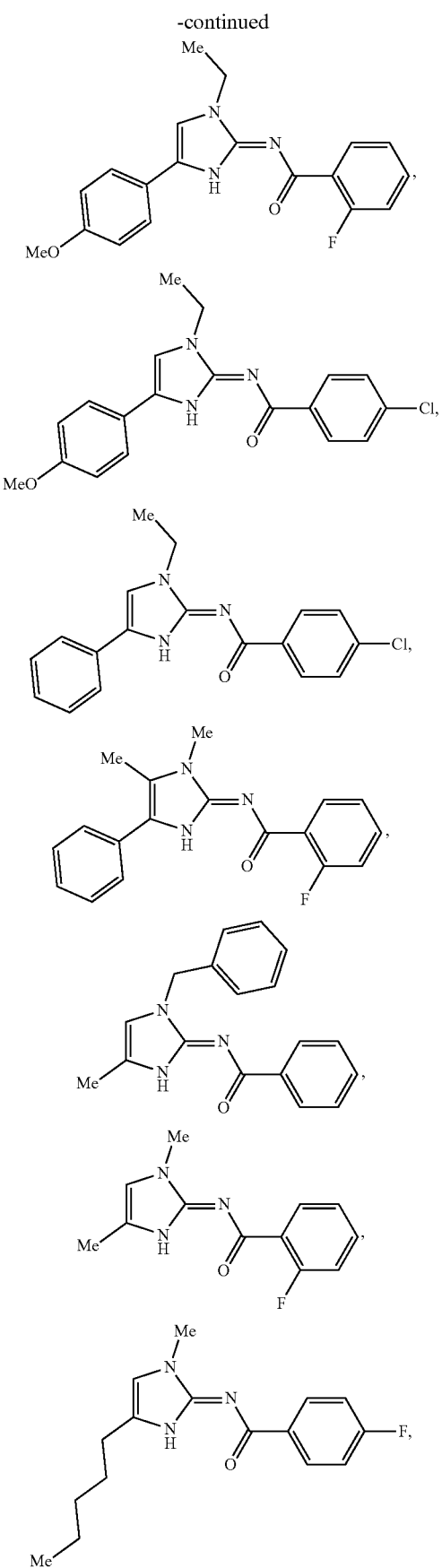
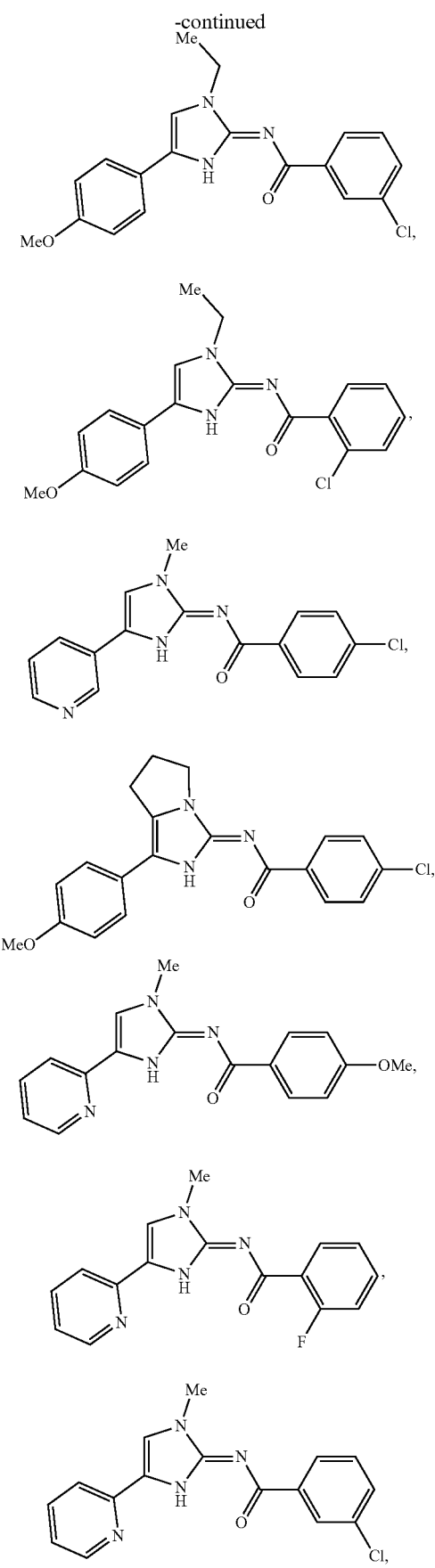

and a salt thereof.

12. The composition of claim 1, wherein the composition comprises the compound or a salt thereof.

13. A method of treating breast cancer, the method comprising administering the composition of claim 1 to a patient with breast cancer, thereby treating the patient.

14. The method of claim 13, wherein the composition comprises the compound or a salt thereof.

* * * * *